(12) United States Patent
Margel et al.

(10) Patent No.: US 10,300,024 B2
(45) Date of Patent: May 28, 2019

(54) PROTEINOID COMPOUNDS, PROCESS OF PREPARING SAME AND USES THEREOF

(71) Applicant: Bar-Ilan University, Ramat Gan (IL)

(72) Inventors: Shlomo Margel, Rehovot (IL); Michal Kolitz Domb, Petah Tikva (IL); Stella Kiel, Ramat Gan (IL); Elisheva Sason, Petah Tikva (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 262 days.

(21) Appl. No.: 15/233,134

(22) Filed: Aug. 10, 2016

(65) Prior Publication Data

US 2017/0042827 A1    Feb. 16, 2017

Related U.S. Application Data

(60) Provisional application No. 62/202,938, filed on Aug. 10, 2015.

(51) Int. Cl.
| | | |
|---|---|---|
| *A61K 38/02* | (2006.01) | |
| *A61K 9/51* | (2006.01) | |
| *A61K 49/00* | (2006.01) | |
| *C08G 63/685* | (2006.01) | |
| *A61K 38/00* | (2006.01) | |

(52) U.S. Cl.
CPC ............ *A61K 9/5169* (2013.01); *A61K 38/00* (2013.01); *A61K 49/0032* (2013.01); *A61K 49/0034* (2013.01); *A61K 49/0043* (2013.01); *A61K 49/0056* (2013.01); *A61K 49/0058* (2013.01); *A61K 49/0093* (2013.01); *C08G 63/685* (2013.01); *C08G 63/6852* (2013.01)

(58) Field of Classification Search
None
See application file for complete search history.

(56) References Cited

U.S. PATENT DOCUMENTS

2002/0161171 A1* 10/2002 Sikes .................. A61K 8/88
528/363

FOREIGN PATENT DOCUMENTS

WO    9428878 A1    12/1994

OTHER PUBLICATIONS

Kolitz-Domb, Michal et al, "Engineering of near infrared fluorescent proteinoid poly(l-lactic acid) particles for in vivo colon cancer detection." J. Nanobiotechnology 2014 12(30).*
Kolitz-Domb, Michal et al, "Synthesis and characterization of bioactive conjugated near infrared fluroescent proteinoid-poly(l-lactic acid) hollow nanoparticles for optical detection of colon cancer." Int. J. Nanomed. 2014 9 p. 5041-5053.*
Landesman-Milo, D., et al., "Hyaluronan grafted lipid-based nanoparticles as RNAi carriers for cancer cells", Cancer Letters, Jul. 1, 2013, pp. 221-227, vol. 334, Issue 2.
Ward, T.C., Molecular weight and molecular weight distributions in synthetic polymers , Journal of Chemical Education, Nov. 1981, pp. 867-879, vol. 58, Issue 11.
Odian, G., "Principles of Polymerization" 3rd Edition, 1991, pp. 108, John Wiley & Sons: New York, USA.

* cited by examiner

*Primary Examiner* — Fred H Reynolds
(74) *Attorney, Agent, or Firm* — The Roy Gross Law Firm, LLC; Roy Gross

(57) ABSTRACT

Proteinoid compounds characterized by a molecular weight (Mw) of at least 15,000 Da, processes of preparing such compounds and methods of use thereof, are provided. A method of monitoring the presence and metastases of cancer in a body of an individual is further disclosed.

19 Claims, 36 Drawing Sheets

(4 of 36 Drawing Sheet(s) Filed in Color)

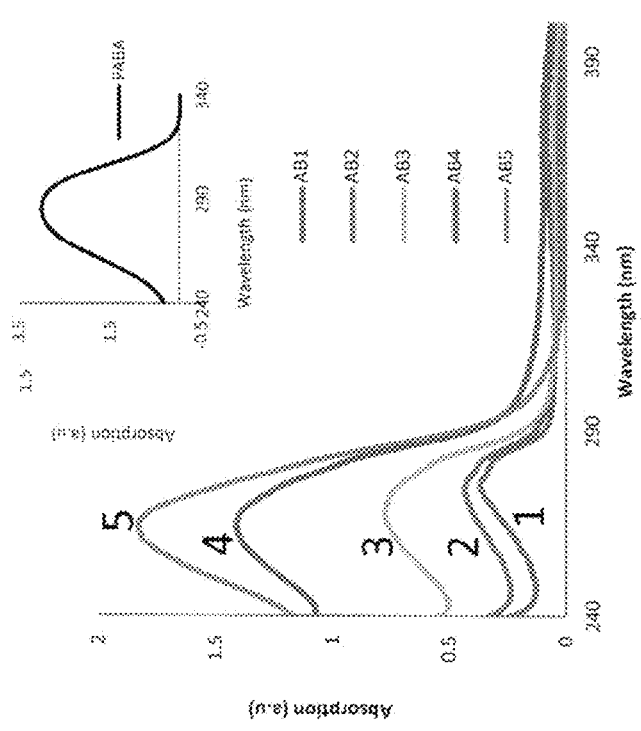
Figure 16A
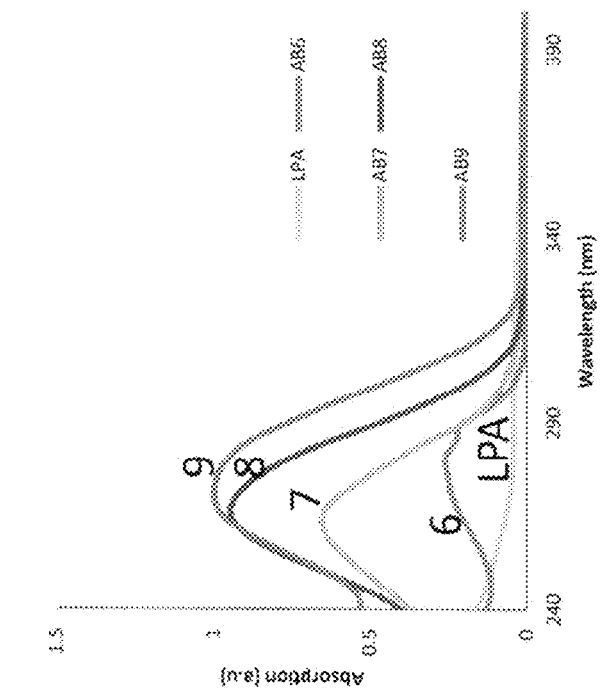
Figure 16B
Figure 16C

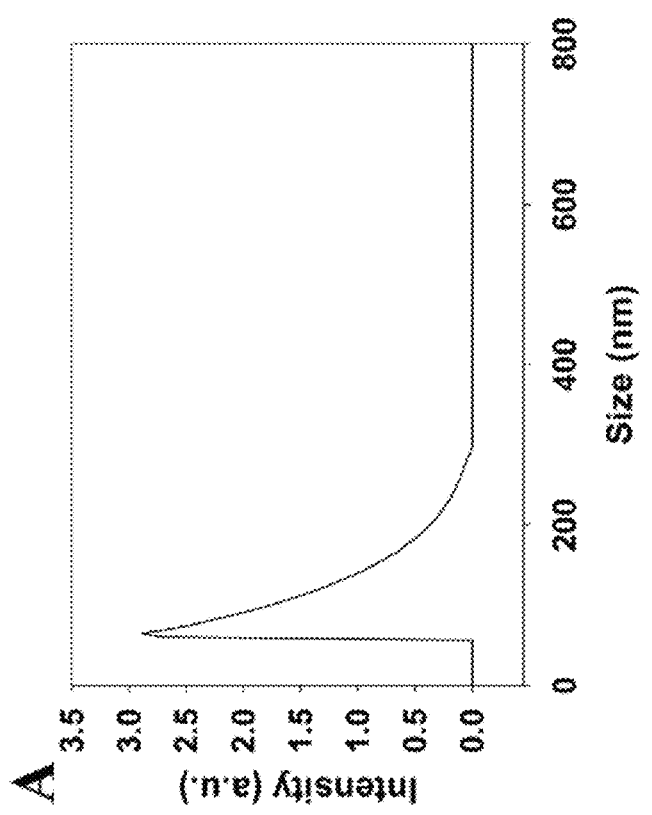
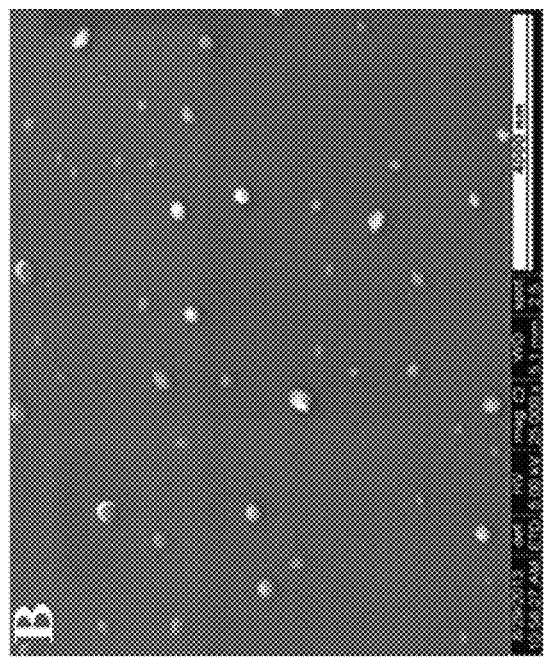
Figure 24B
Figure 24A

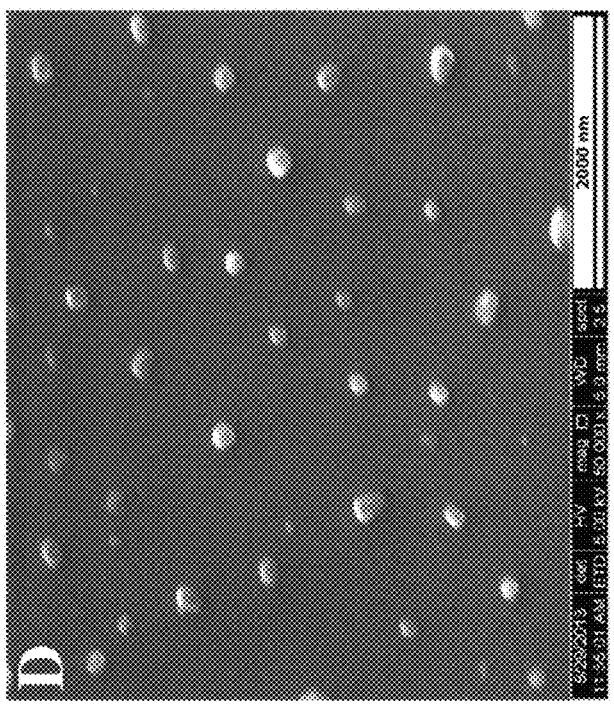
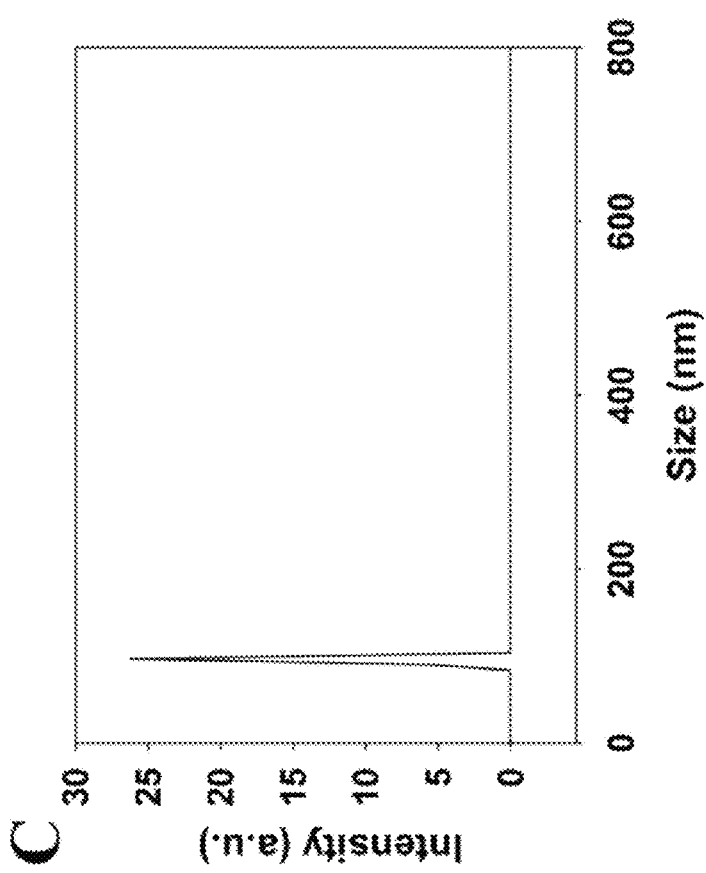
Figure 24C
Figure 24D

PROTEINOID COMPOUNDS, PROCESS OF PREPARING SAME AND USES THEREOF

This application claims the benefit of priority from U.S. Provisional Patent Application No. 62/202,938, filed on Aug. 10, 2015. The content of the above document is incorporated by reference in its entirety as if fully set forth herein.

FIELD OF INVENTION

The present invention relates to proteinoid compounds, processes of preparing such compounds and uses thereof.

BACKGROUND OF THE INVENTION

Proteinoids comprise small poly(amino acid) polymers prepared by thermal random condensation polymerization of various α-amino acids.

It is well known that polymers obtained by condensation polymerization mechanism possess a very broad molecular weight distribution (polydispersity index, Mw/Mn), commonly between 1.5-2.0 (T. C. Ward, J. of Chemical Education 58 (11), 867-879), and typically with mean molecular weight that falls within the lower end of the molecular weight range of typical biogenic proteins (4000-10,000 Da).

A well-designed polymeric drug delivery system, whether it is targeting the tumor site passively or actively, improves the therapeutic index of the drugs, their selective tumor accumulation, their time of exposure to the tumor vasculature (i.e. to the tumor endothelial cells), while reducing their toxicity.

International patent application publication no. WO 1994/028878 discloses proteinoid carriers and methods for their preparation and use as oral delivery systems for pharmaceutical agents are described, wherein the proteinoid carriers are soluble within selected pH ranges within the gastrointestinal tract and display enhanced stability towards at least one of photolysis or decomposition over time. WO 1994/028878 discloses the preparation of the proteinoid carriers from proteinoids having between 2 and 20 amino acids and having a molecular weight of between about 250 and 2400 daltons.

SUMMARY OF THE INVENTION

The present invention provides proteinoid compounds characterized by a molecular weight (Mw) of at least 15,000 Da, processes of preparing such compounds and uses thereof.

The present inventors have surprisingly uncovered that proteinoid compounds characterized by a high molecular weight (Mw) and low dispersity can be readily prepared.

According to an aspect of some embodiments of the present invention, there is provided a proteinoid compound comprising a polymeric backbone, wherein the polymeric backbone comprises monomeric units, each of the monomeric units being derived from an amino acid, and wherein the polymeric backbone is characterized by a molecular weight (Mw) of at least 15,000 Da.

In some embodiments, the amino acid, in each instance, is selected from the group consisting of: Glu, Lys, Asp, Arg, Tyr, His, Ala, Phe, Cys, Ile, and p-amino benzoic acid.

In some embodiments, the polymeric backbone further comprises polyester.

In some embodiments, the polyester is selected from the group consisting of polylactide, polyglycolide, and polycaprolactone, polyhydroxyalkanoate.

In some embodiments, the polymeric backbone is represented by the following formula

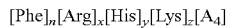
$[Phe]_n[Arg]_x[His]_y[Lys]_z[A_4]$ wherein:

$A_4$ represents a polyester or is absent;

n, x, y, and z are integers, independently, representing the total numbers of Phe, Arg, His, and Lys, respectively, in the polymeric backbone, such that n+x+y+z has a value of at least 100.

In some embodiments, the polymeric backbone is represented by the following formula:

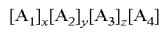
$[A_1]_x[A_2]_y[A_3]_z[A_4]$ wherein:

a) $A_1$, in each instance, is selected from Glu and Lys;

b) $A_2$, and $A_3$ are each, independently, a monomeric unit derived from an amino acid or are each, independently, absent;

c) $A_4$ represents the polyester or is absent;

d) x, y, and z are integers, independently, representing the total numbers of $A_1$, $A_2$, and $A_3$, respectively, in the polymeric backbone, such that x+y+z has a value of at least 100.

In some embodiments, the amino acid is selected from the group consisting of: Asp, Lys, Arg, and Phe.

In some embodiments, the polyester is at least 1%, by weight, of the polymeric backbone.

In some embodiments, wherein A1 is Glu, A2 is Phe and A3 is absent.

In some embodiments, A1 is Glu, A2 is Asp, and A3 is selected from the group consisting of Lys, Phe, or is absent.

In some embodiments, A1 is Glu, A2 is Lys, and A3 is Phe or is absent.

In some embodiments, x, y, and z have a value such that at least one of: x/y, x/z, and y/z ranges from about 1:3 to about 3:1.

In some embodiments, A4 is absent.

In some embodiments, A4 is polylactide.

In some embodiments, the polyester is at least 1%, by weight, of the polymeric backbone.

According to another aspect of some embodiments of the present invention, there is provided a composition-of-matter comprising a plurality of the proteinoid compounds.

In some embodiments, at least 80% of the plurality of the proteinoid compounds is characterized by a dispersity index (Ð) value of less than 1.1.

In some embodiments, the composition-of-matter further comprises one or more agents selected from: labeling compound, UV blocker, an antibacterial compound, a magnetite, an antioxidant, a filler, biologically active agent, the one or more agents being attached to and/or encapsulated within the hollowsphere.

According to another aspect of some embodiments of the present invention, there is provided a method of monitoring the presence and metastases of cancer in a body of an individual, the method comprising administering to the individual the composition-of-matter and employing an imaging technique for monitoring a distribution of the composition-of-matter within the body or within a portion thereof.

According to another aspect of some embodiments of the present invention, there is provided a process of synthesizing a proteinoid compound characterized by molecular weight (Mw) of at least 15,000 Da, the process comprising:

heating one or more types of amino acid to a temperature that ranges from 100° C. to 200° C., under an inert gas, thereby forming a molten content or a mixture of the one or more amino acids;

stirring the molten content or a mixture at a temperature that ranges from 100° C. to 200° C., for at least 30 min, thereby polymerizing a plurality of monomeric units derived from the one or more amino acids in the content or mixture;

bringing the content or mixture to room temperature;

adding water to the content or a mixture, thereby obtaining a proteinoid compound solution; and cleaning (e.g., dialyzing) the solution to thereby obtain the proteinoid compound.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 shows the thermal polycondensation kinetics of (L)glutamic acid and (L) phenylalanine to yield Prot3 at 180, 190 and 200° C. by two tests: ninhydrin test (A) and Biuret test (B).

Figure 2:
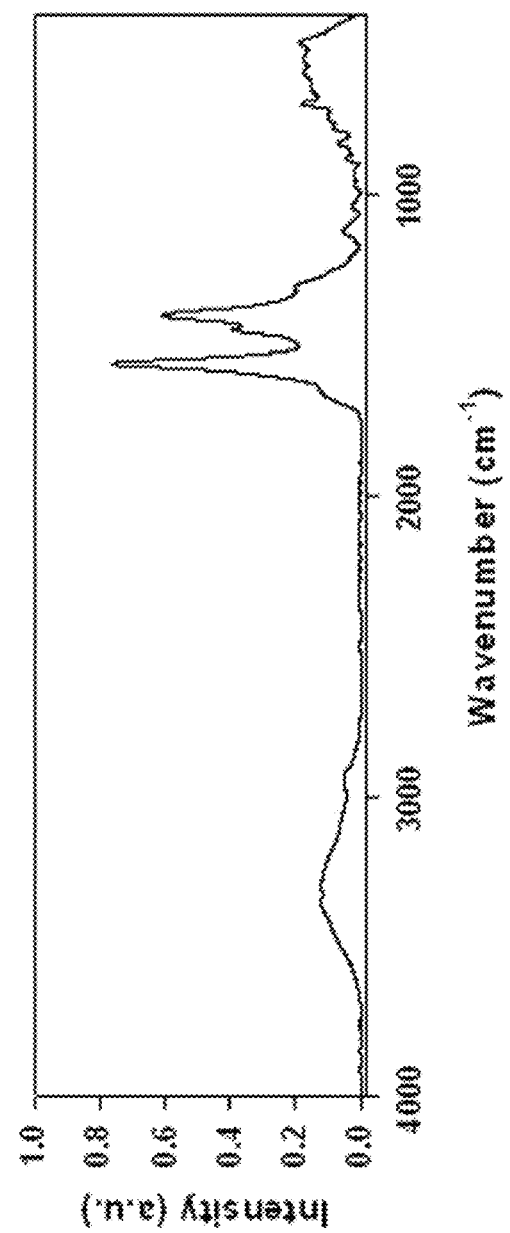

FIG. 2 presents fourier transform infrared spectroscopy (FTIR) spectrum of Prot3. Characteristic peaks of NH stretching at 3360 and 2990 $cm^{-1}$, amide CO stretching at 1565 $cm^{-1}$, an amide NH bending band at 1450 $cm^{-1}$ and CO bending at 500-700 $cm^{-1}$ are shown.

Figure 3A:
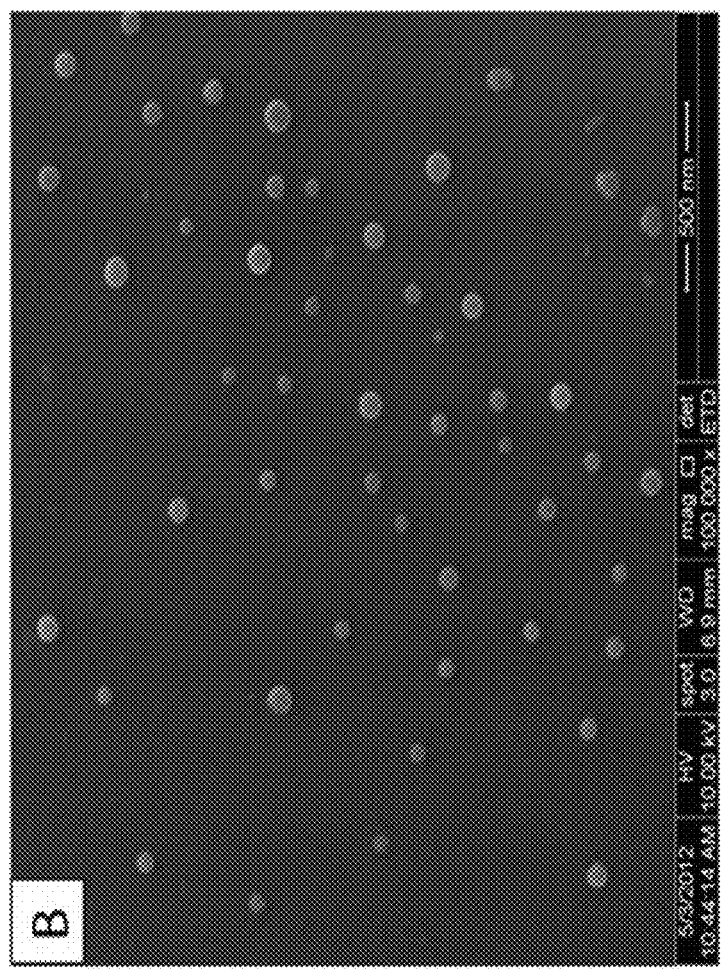
Figure 3B:
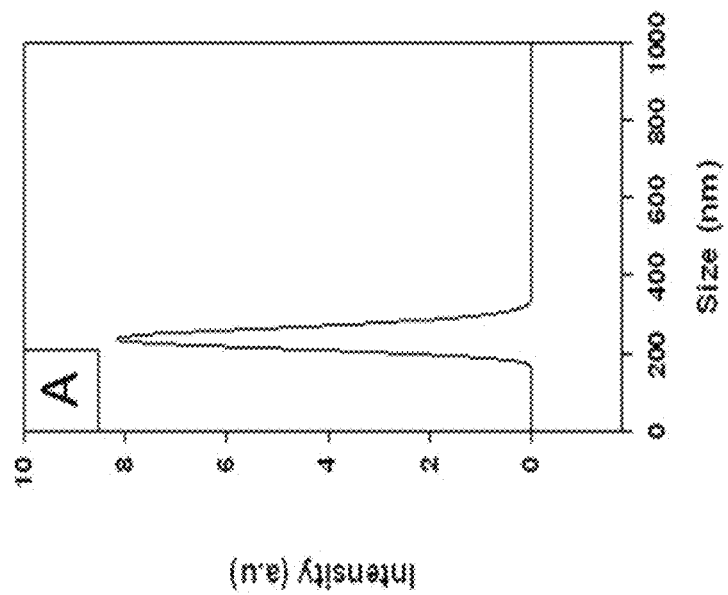

FIGS. 3A-B present hydrodynamic size histogram (FIG. 3A) and scanning electron microscope (SEM) image (FIG. 3B) of Prot8 particles.

Figure 4:
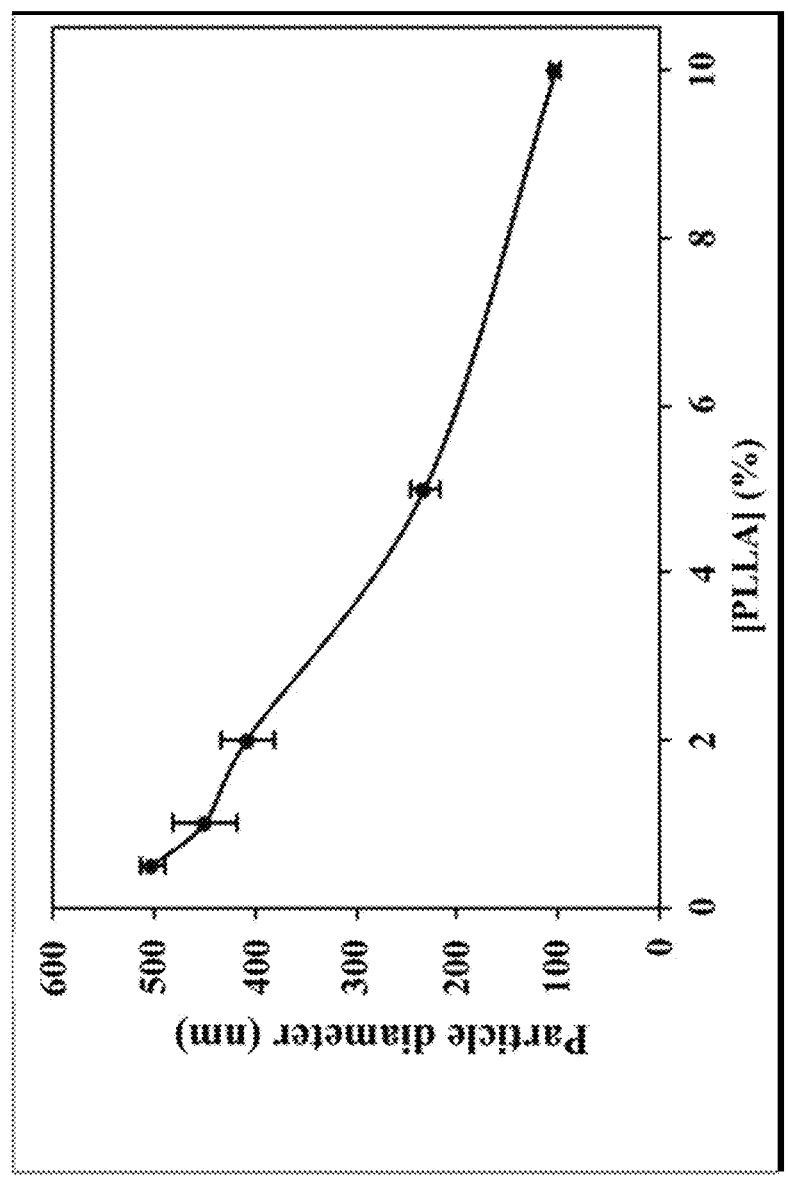

FIG. 4 presents the effect of the poly(L-lactic acid) (PLLA) weight % of the total monomer weight in synthesized P(EF-PLLA) on the hydrodynamic particle diameter.

Figure 5:
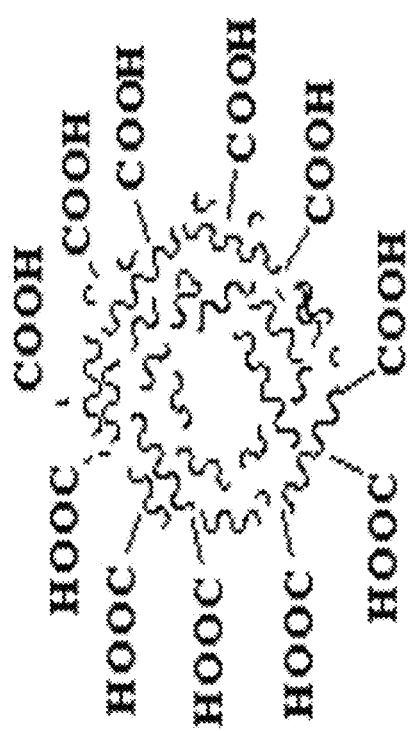

FIG. 5 presents schematic representation of the self-assembled proteinoid particles; hydrophobic moieties are represented by scribbled lines. When lysine is also a part of the proteinoid, as in Prot5-7 as described below, some carboxyl groups are exchanged with amine groups.

Figure 6:
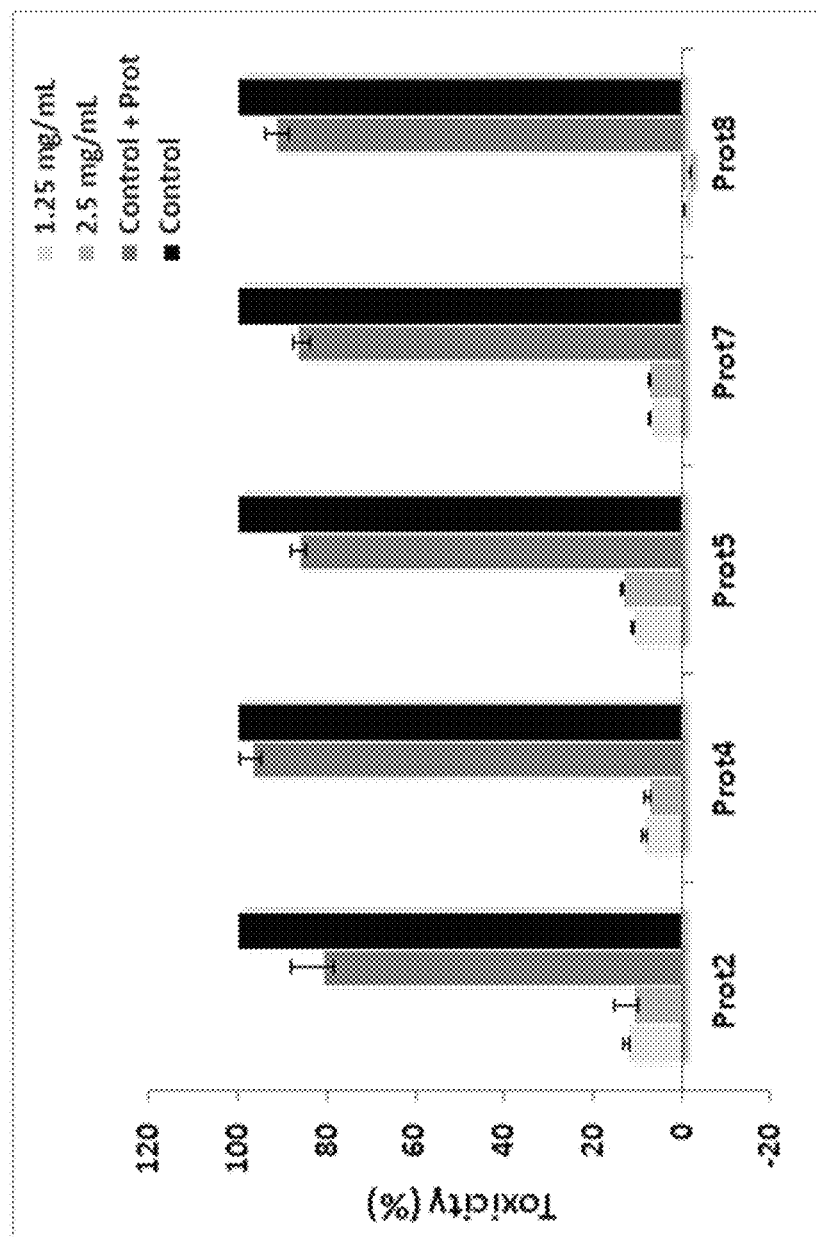

FIG. 6 presents the cytotoxic effect of the proteinoid particles on colon adenocarcinoma L5174T cells measured by the lactate dehydrogenase (LDH) assay. Cells ($3\times10^5$) were incubated with the proteinoid particles dispersed in PBS (1.25 mg/mL and 2.5 mg/mL from left to right) according to the experimental section. Cells were incubated with Triton-x-100 1% as positive control (100% toxicity). In addition, cells were incubated with Triton-x-100 1% and each one of the proteinoids to revoke any interaction. Untreated cells (negative control; right bar) were similarly incubated. Each bar represents mean±standard deviations of 4 separate samples.

Figure 7:
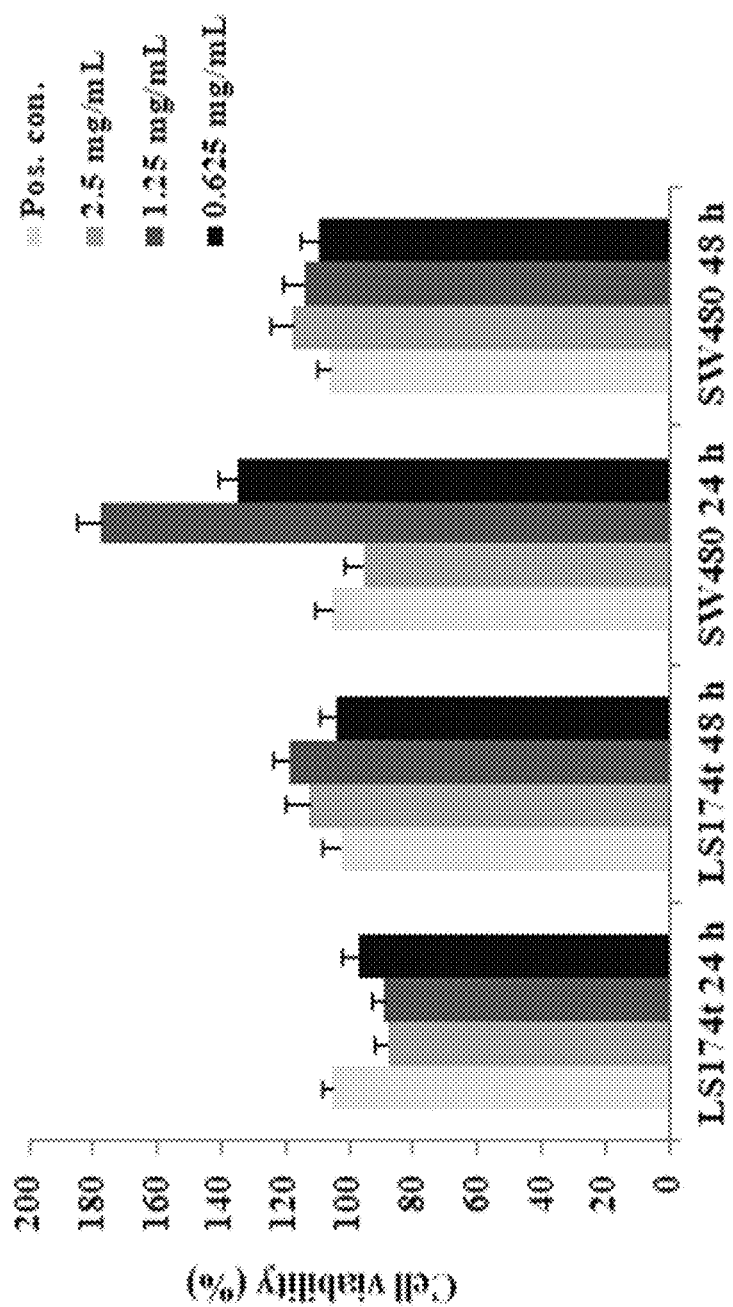

FIG. 7 presents the cell viability levels of human colorectal adenocarcinoma LS174t and SW480 cell lines after exposure to the NIR fluorescent P(EF-PLLA) particles measured by the XTT assay. Cells ($3\times10^5$) were incubated for 24 and 48 h with the polymeric P(EF-PLLA) particles (0.625, 1.25, 2.5 mg/mL and control in PBS-from right to left in each quartet, respectively). Untreated cells (positive control) were similarly incubated. Each bar represents mean ±standard deviations of 4 separate samples.

Figure 8:
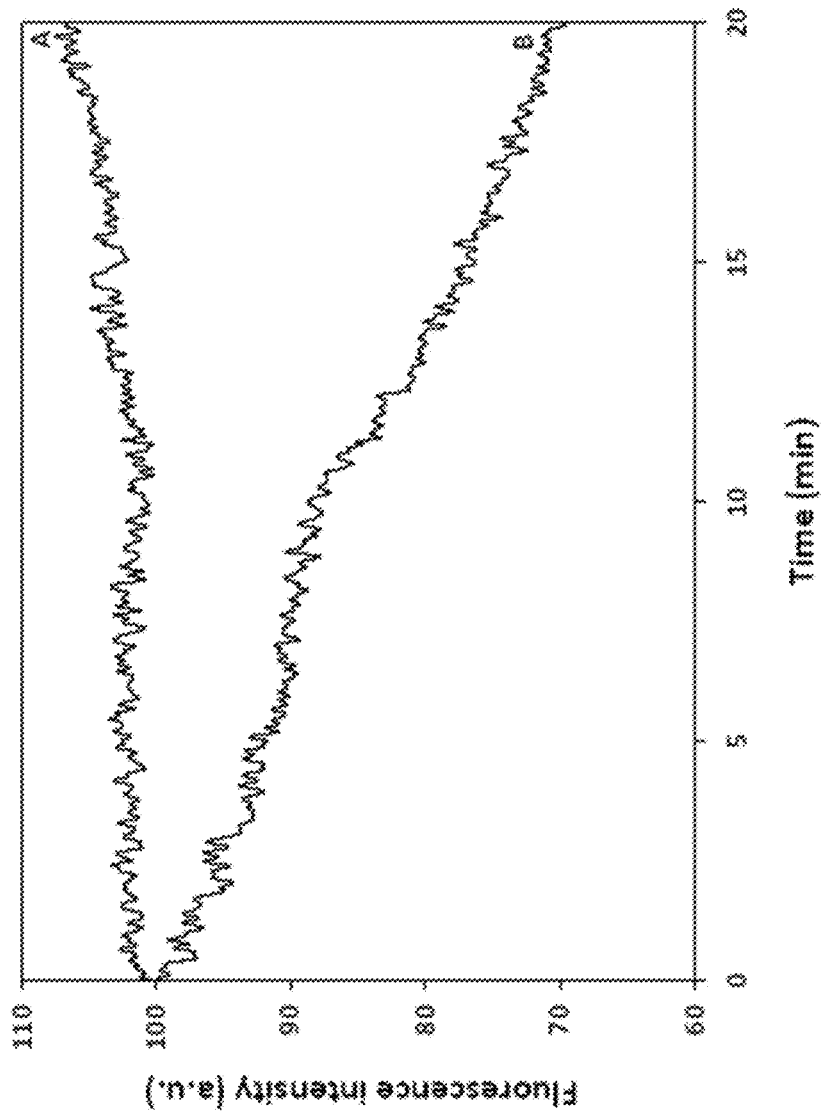

FIG. 8 presents the photostability of the ICG-P(EF-PLLA) particles (A) and free ICG (B) as function of time. Samples of ICG-containing P(EF-PLLA) particles and free ICG were illuminated with a Xenon flash lamp for 20 min as described below (ICG: indocyanine green).

Figure 9:
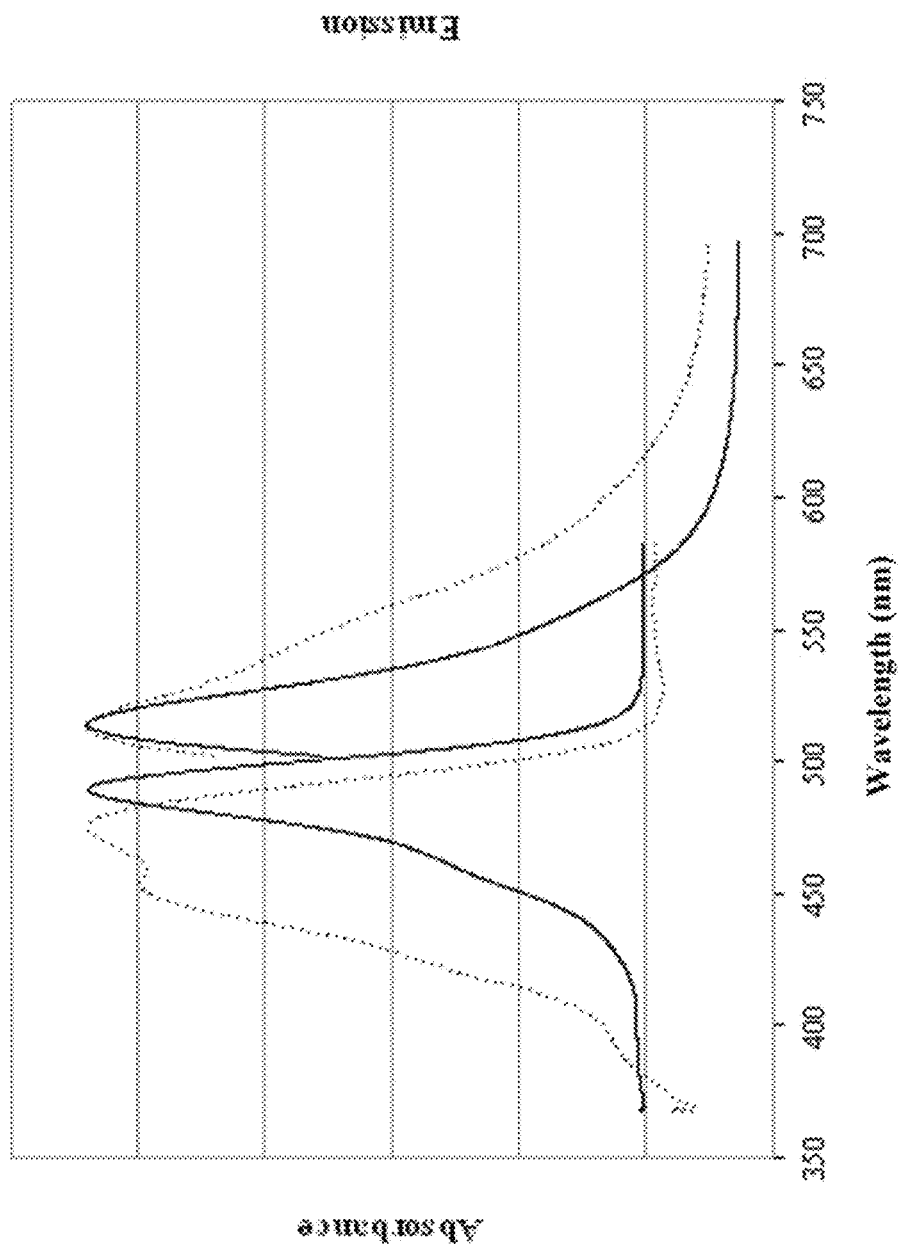

FIG. 9 presents the absorbance and emission spectra of free fluorescein (dotted lines) and fluorescein proteinoid particles dispersed in water (solid lines). The maximum absorbance of free fluorescein and fluorescein encapsulated proteinoid particles occurs at approximately 475 nm and 489 nm, respectively. The fluorescence emission maxima occur at approximately 513 nm and 514 nm, respectively.

Figure 10A:
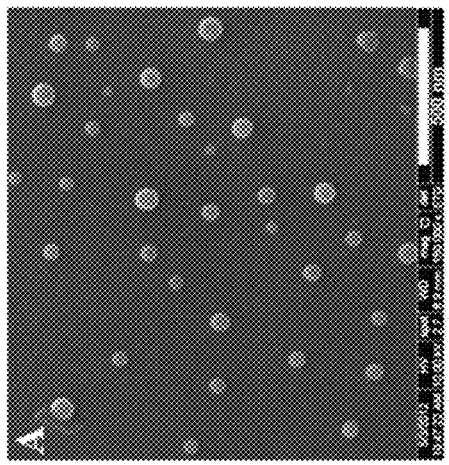
Figure 10B:
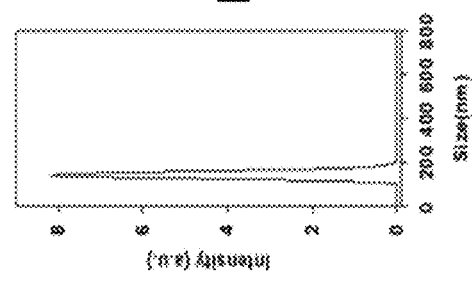
Figure 10C:
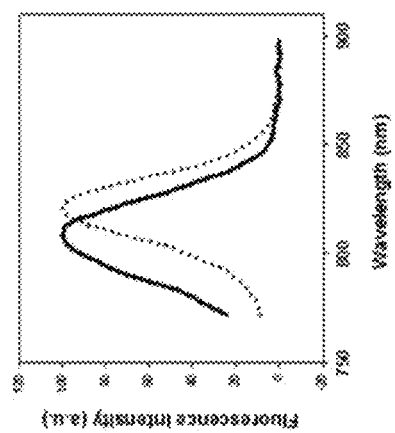
Figure 10D:
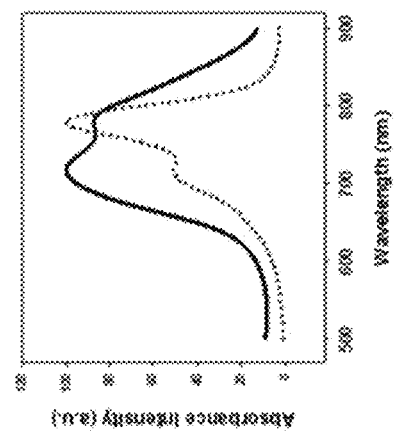

FIGS. 10A-D present characterization of the near infrared (NIR) fluorescent P(EF-PLLA) nanoparticles. FIGS. 10A and 10B present SEM image and hydrodynamic size histogram of the NIR fluorescent P(EF-PLLA) nanoparticles, respectively; FIGS. 10C and 10D present emission and absorbance spectra of free ICG (dotted lines) and nanoparticles containing ICG (solid lines), respectively.

Figure 11:
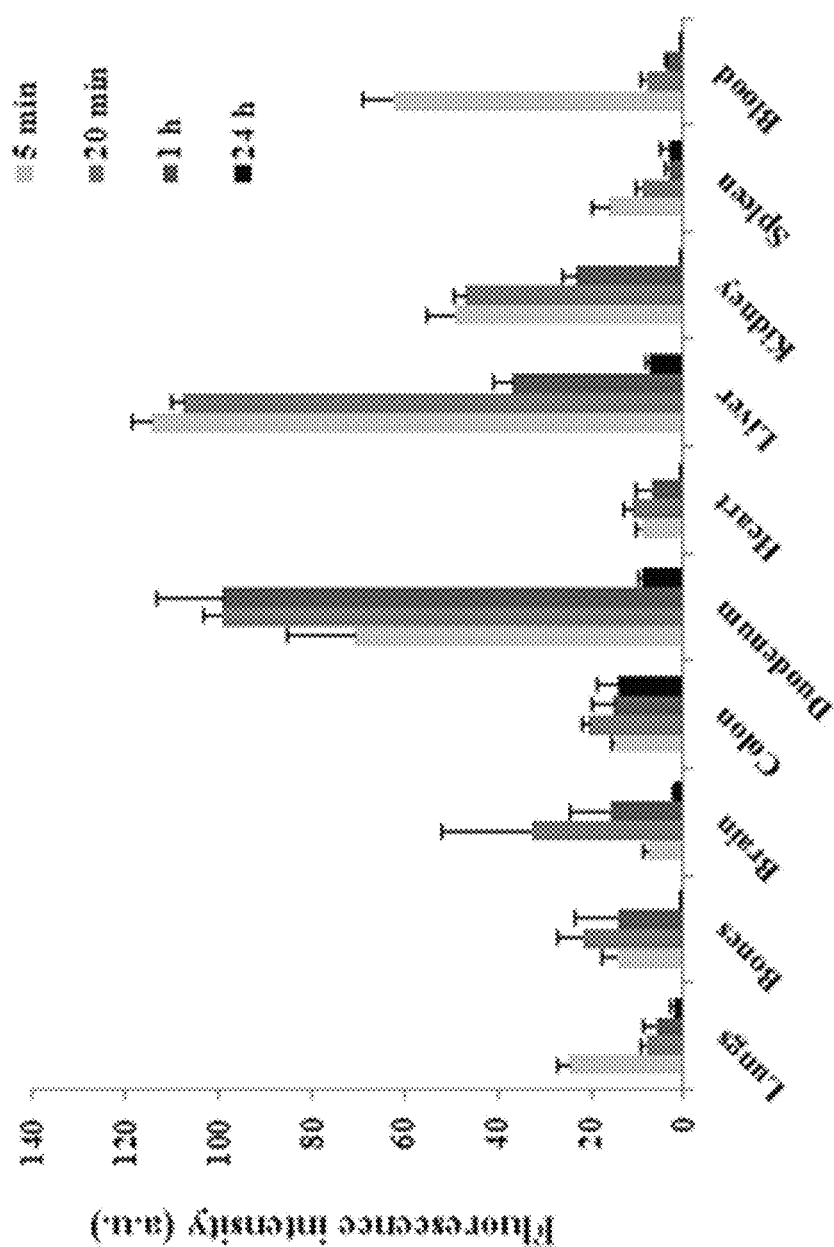

FIG. 11 presents fluorescence intensities of different organs taken at 5 min, 20 min, 1 h and 24 h (from left to right in each quartet of bars) post i.v. injection into mice tail veins. 12 mice (each experiment group contained 3 mice) were anesthetized and treated with NIR fluorescent P(EF-PLLA) nanoparticles (2 mg/mL, 0.01 mg/kg body weight per mouse). Blood was drawn and organs were harvested at each time point. Two uninjected mice served as negative control. The experiment was repeated twice with similar results.

Figure 12:
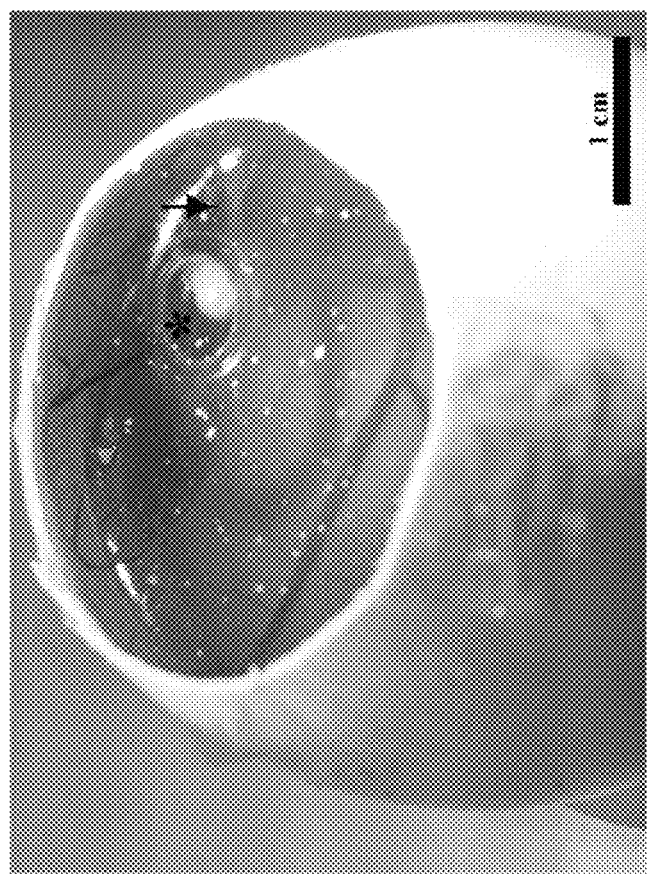

FIG. 12 presents light photograph of SW480 cell line derived tumors bordered by a plastic ring on chicken embryo CAM. Suspensions of $5\times10^6$ SW480 cells suspended in Matrigel formed compact structures (asterisk) 8 days after transplantation with attraction of host blood vessels (arrow). CAM: chicken chorioallantoic membrane.

Figure 13:
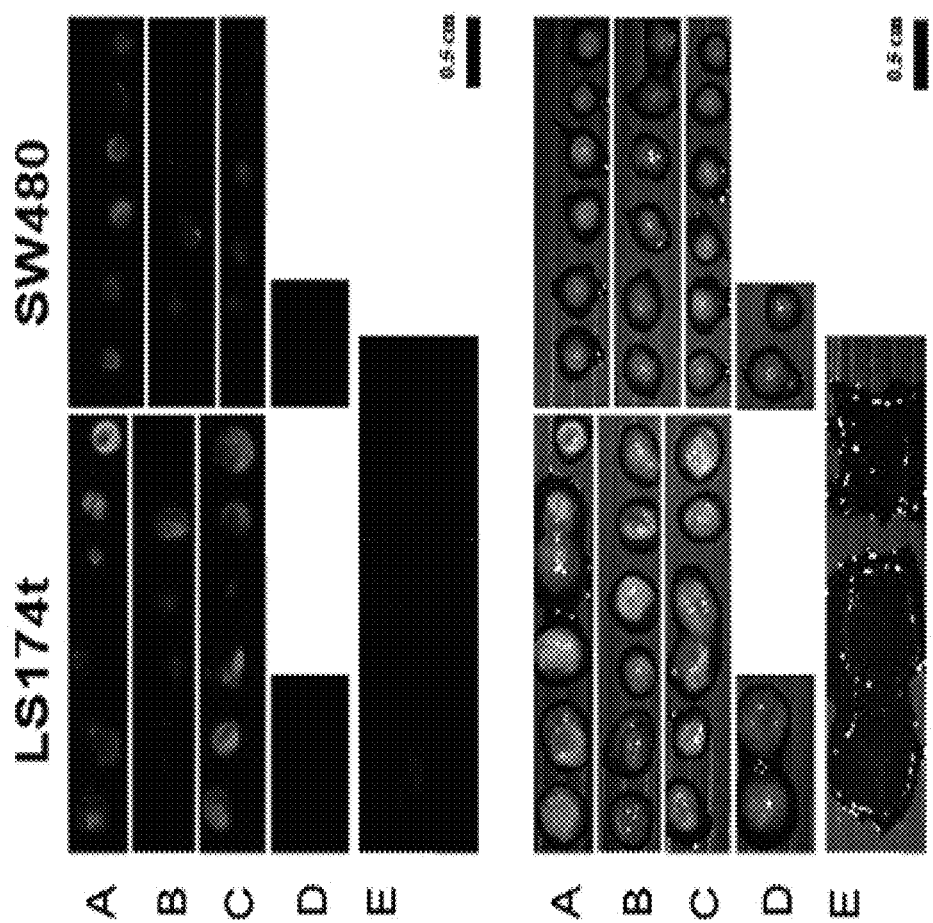

FIG. 13 presents fluorescent (upper) and greyscale (lower) images from a typical experiment of tumor cell lines LS174t and SW480 implants on chicken embryo CAM treated with non-conjugated (A), PNA-conjugated (B) and anti-CEA-conjugated (C) NIR fluorescent P(EF-PLLA) nanoparticles. Images of untreated tumor cell lines are shown in (D). Images of non-pathological CAM treated with non-conjugated, PNA-conjugated and anti-CEA-conjugated particles are shown in (E). The experiment was repeated 5 times with similar results. PNA: peanut agglutinin; CEA: carcinoembryonic antigen.

Figure 14:
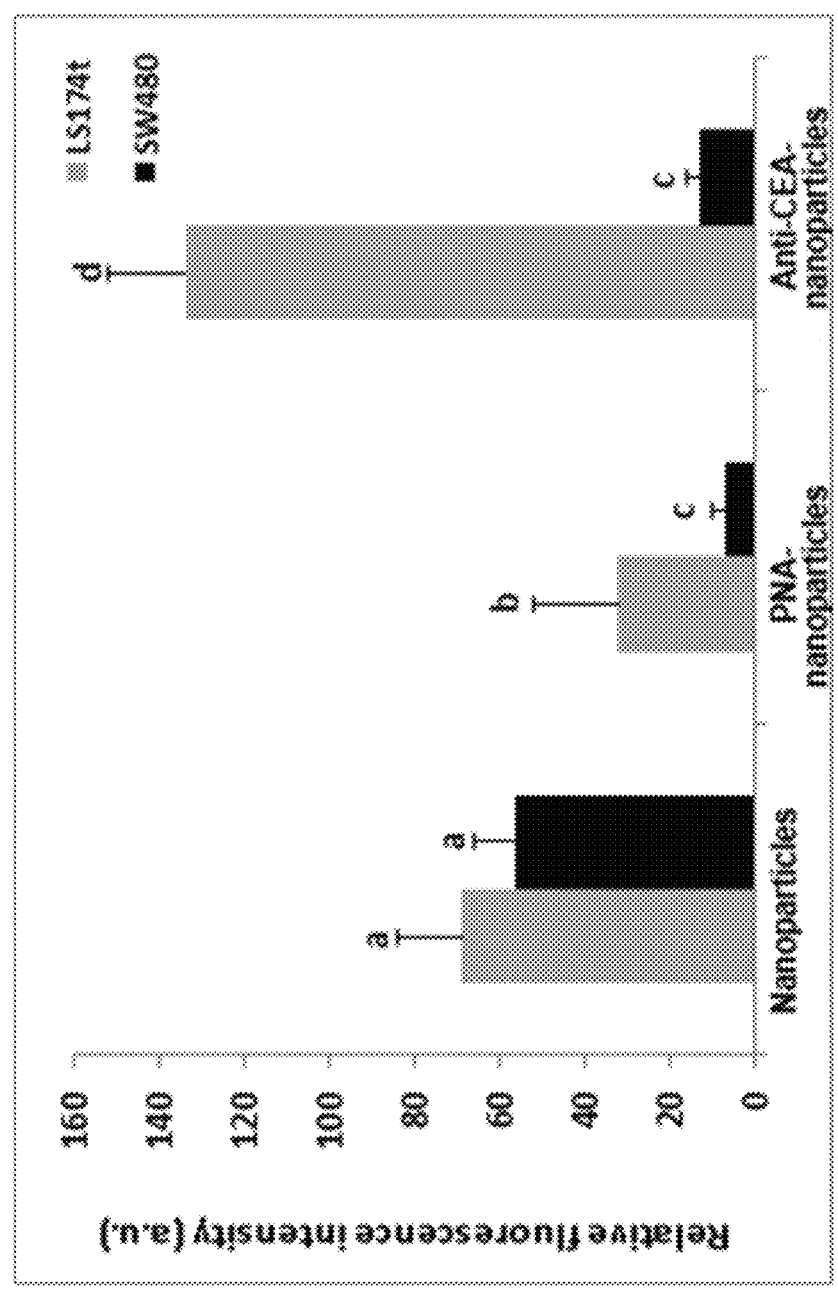

FIG. 14 presents relative fluorescence intensities of LS174t (left bar in each couple) and SW480 tumors labeled with non-conjugated, PNA-conjugated and anti-CEA-conjugated particles. Data is presented as the mean value±SE. Values not sharing a common letter (a, b, c or d) differ significantly from each other (p<0.05). The calculations are an average of 3 experiments.

Figures 15A, 15B:
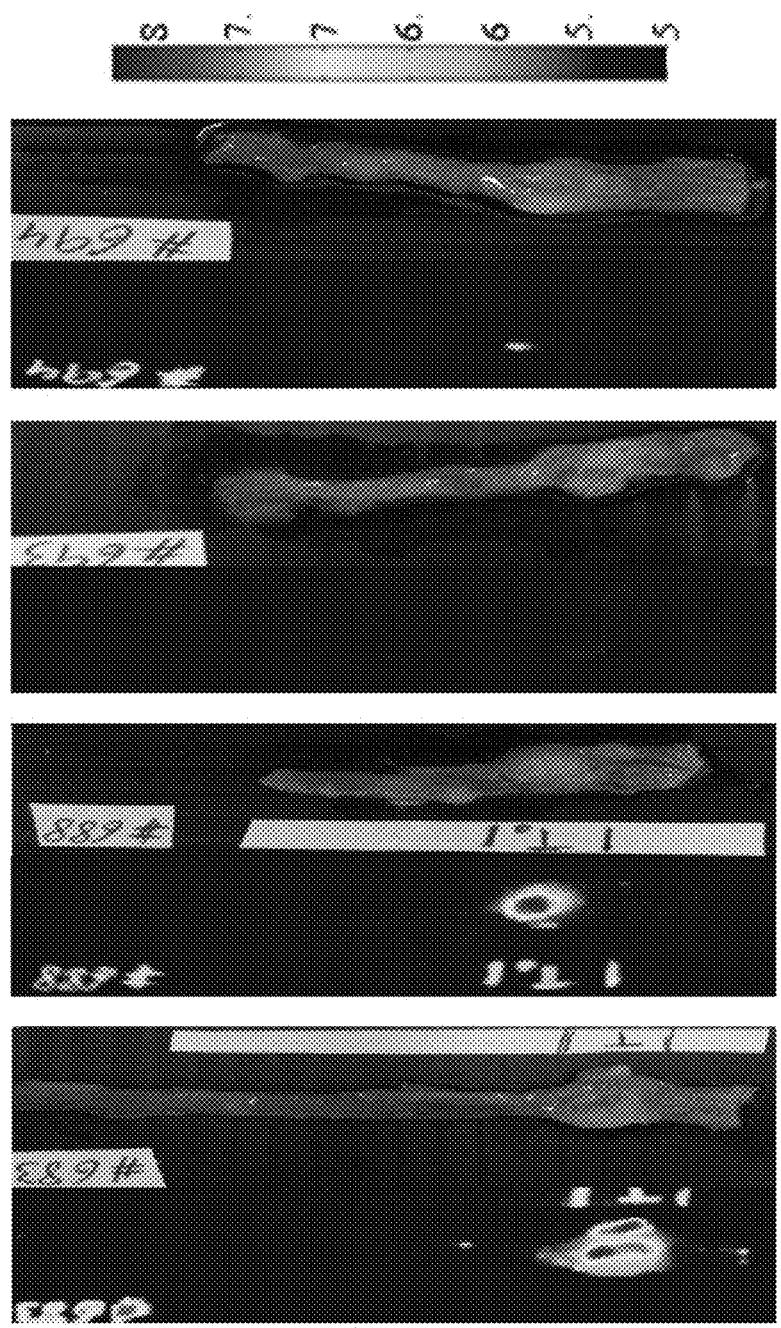

FIGS. 15A-B present fluorescent and grayscale images of typical LS174t colon tumors treated with anti-CEA (FIG. 15A) and anti-rabbit IgG-conjugated NIR fluorescent P(EF- PLLA) nanoparticles (FIG. 15B). 20 mice (10 in each experiment group) were anesthetized and treated with 0.1% particle dispersion in PBS, as described in the methods section. Two untreated mice served as a control group.

FIGS. 16A-C present absorption spectra of the different proteinoids. All proteinoids were dissolved in double distilled water (DDW) (FIGS. 16A, 16B) and PABA in NaOH 1M solution (1 mg in 1 ml) and scanned for their absorption by spectrophotometer (FIG. 16C). PABA: 4-Aminobenzoic acid. The numbers refers to the graphs, respectively, e.g., "1" refers to "AB1".

FIGS. 17A-D present hydrodynamic size histogram (FIGS. 17A and C) and cryo transmission electron microscopy (TEM) image (FIGS. 17B and D) of AB5P (as designated below) and AB5P RA 5%. RA: retinoic acid.

Figures 18A, 18B, 18C:
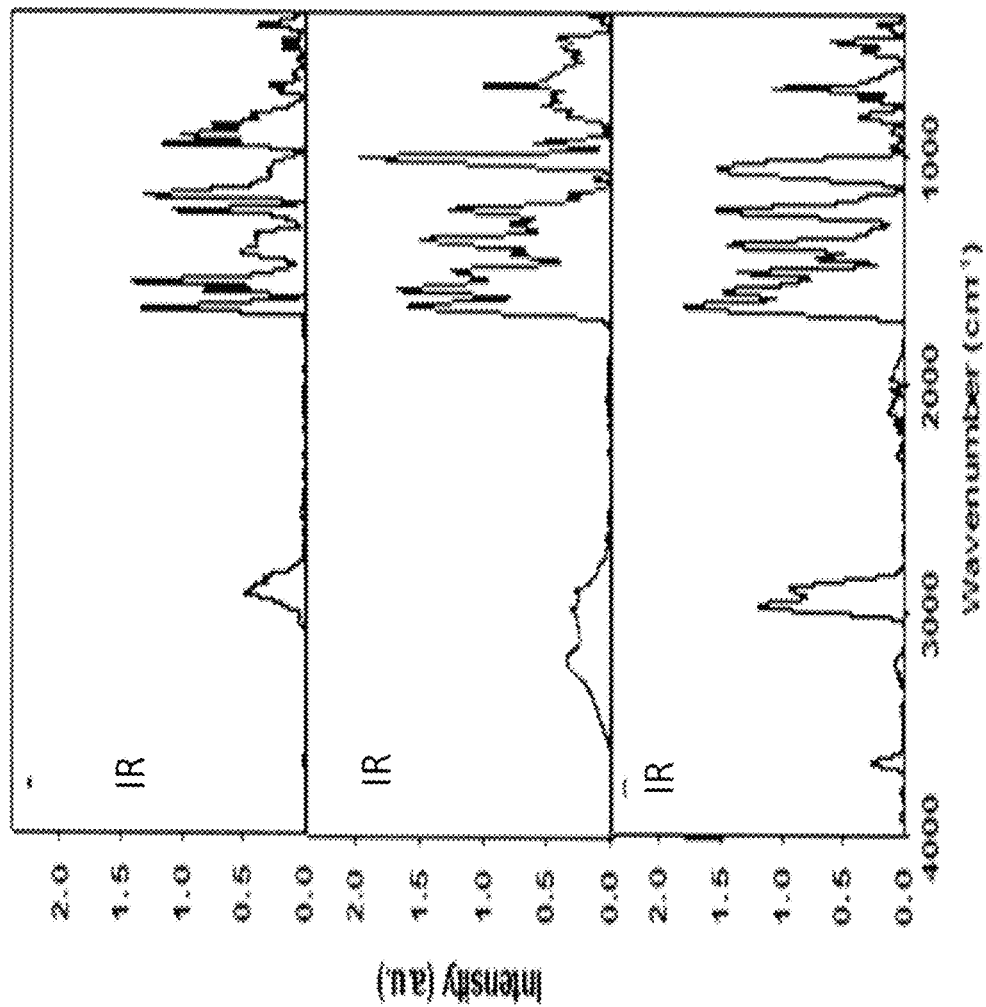

FIGS. 18A-C present FTIR spectrum of RA (FIG. 18A), AB5P (FIG. 18B) and AB5P RA (FIG. 18C). FTIR: Fourier transform infrared spectroscopy.

Figure 19:
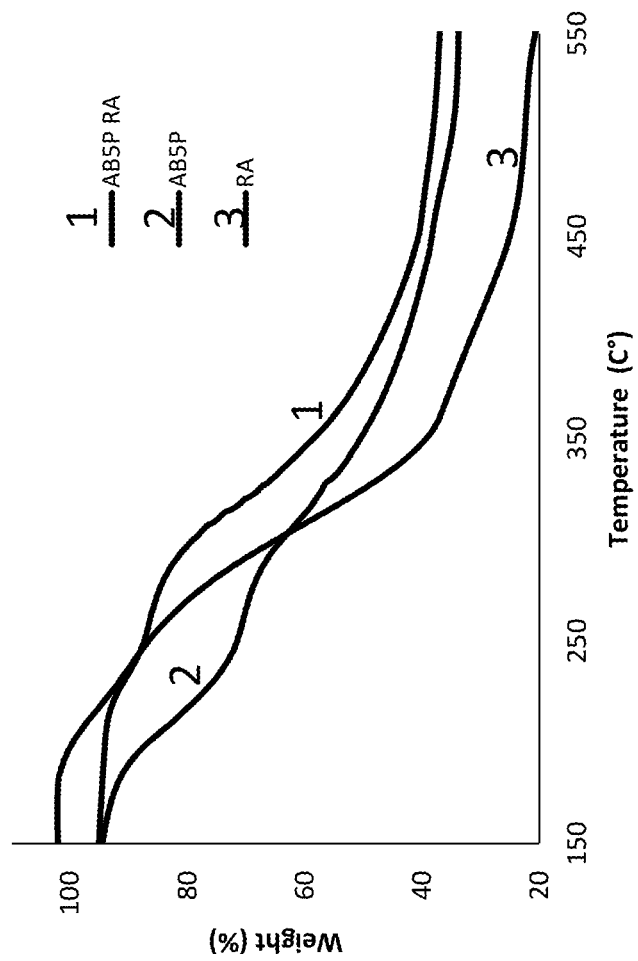

FIG. 19 presents TGA thermogram of RA, AB5P and AB5P RA 1%.TGA: thermogravimetric analysis.

Figure 20:
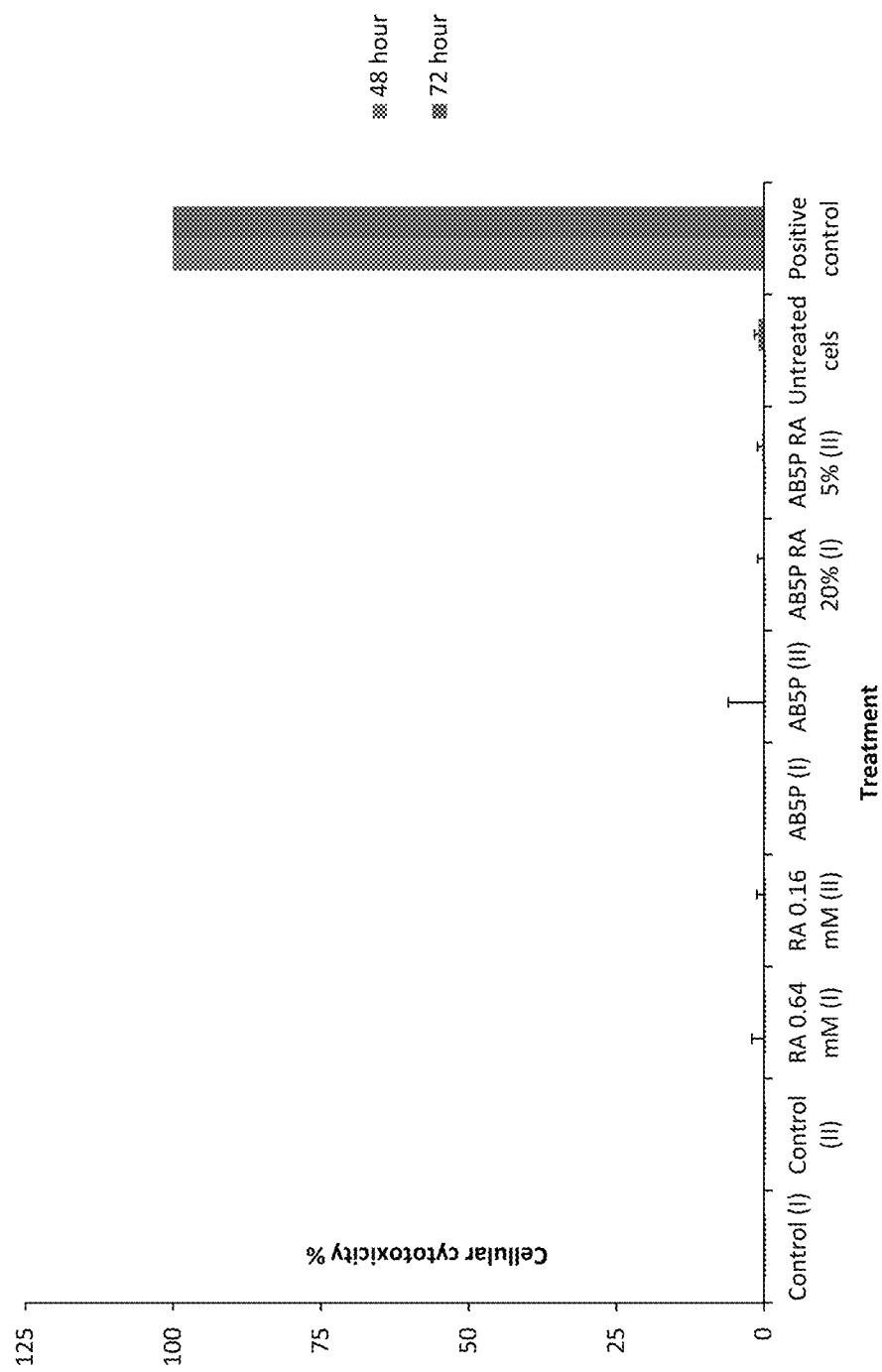

FIG. 20 presents the cytotoxic effect of the proteinoid particles on HaCaT cells measured by the LDH assay. Cells ($3 \times 10^5$) were incubated for 48 (left bar in each couple) and 72 h (right bar) with the proteinoid particles dispersed in DDW (0.1 mg/mL) (I and II depict for 0.1 and 0.05% dimethyl sulfoxide; DMSO). Cells were incubated with Triton-x-100 1% as positive control (100% toxicity). Untreated cells (negative control) were similarly incubated. Each bar represents mean±standard deviations of 4 separate samples.

Figure 21:
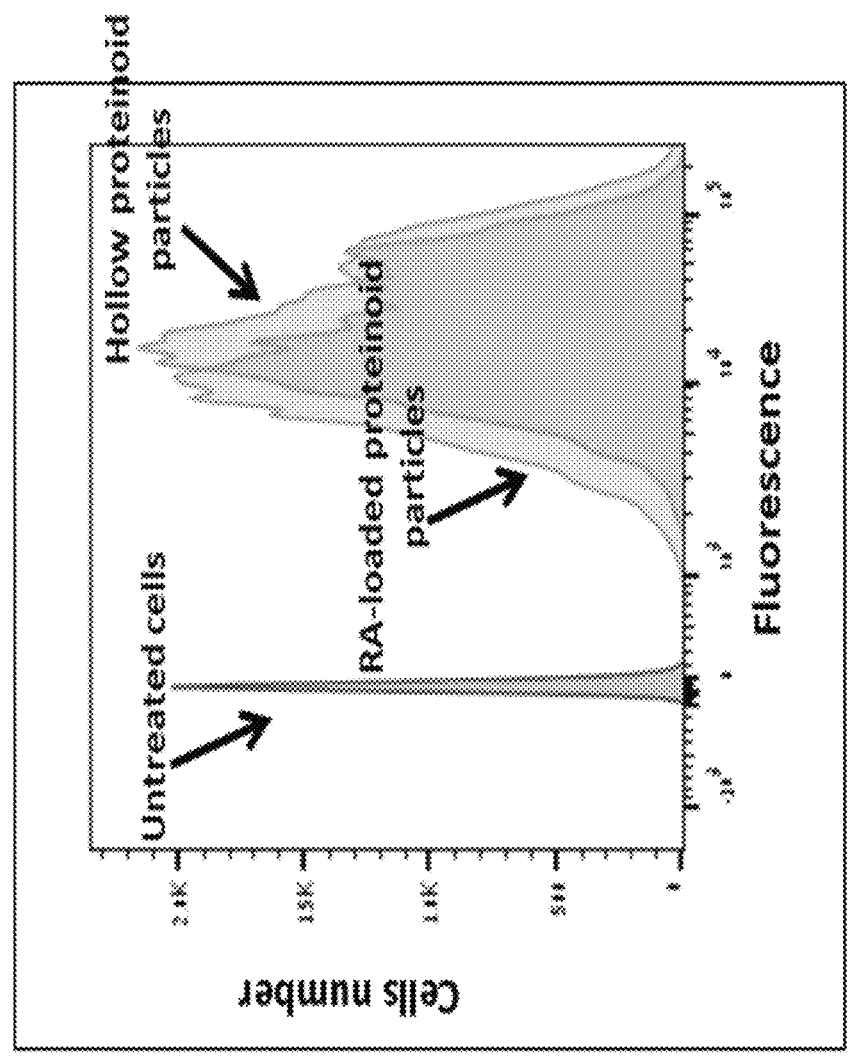

FIG. 21 presents particle penetration into HaCaT cells by fluorescence-activated cell sorting (FACS).

Figure 22:
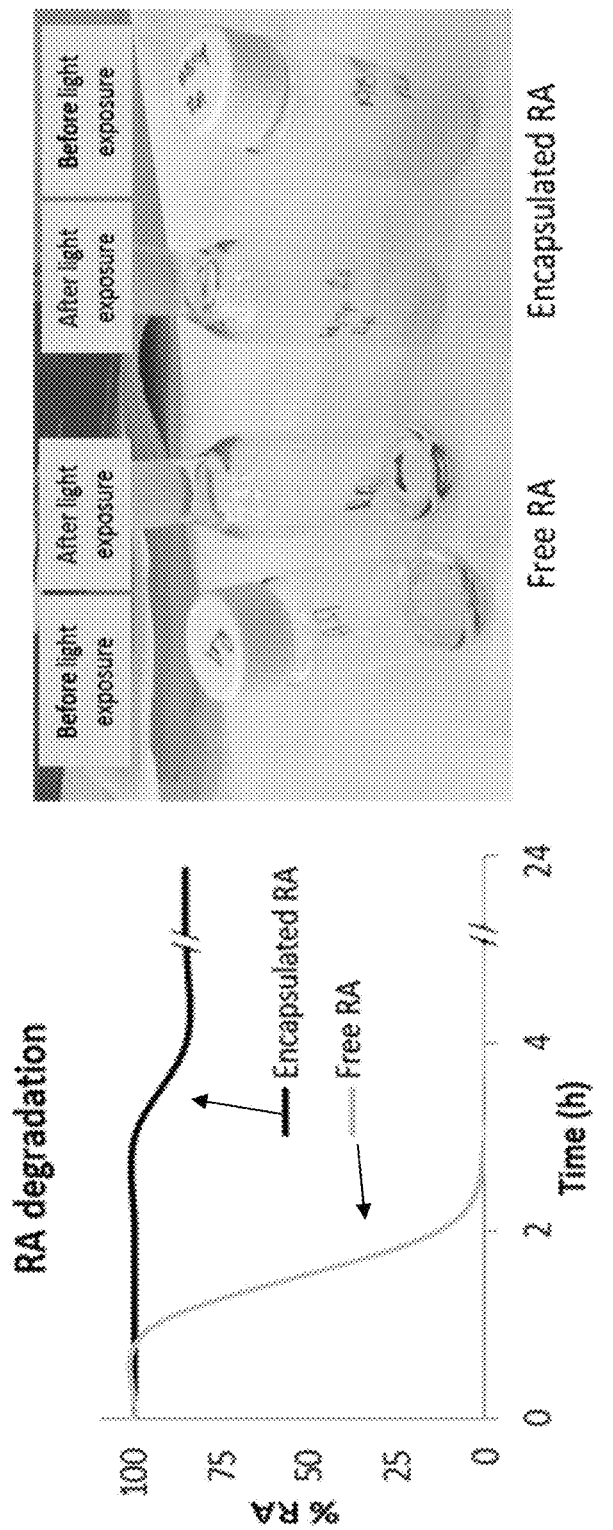

FIG. 22 presents the effect of encapsulation on the degradation of RA over time by HPLC (right) and corresponding real-time photographs (left).

Figure 23:
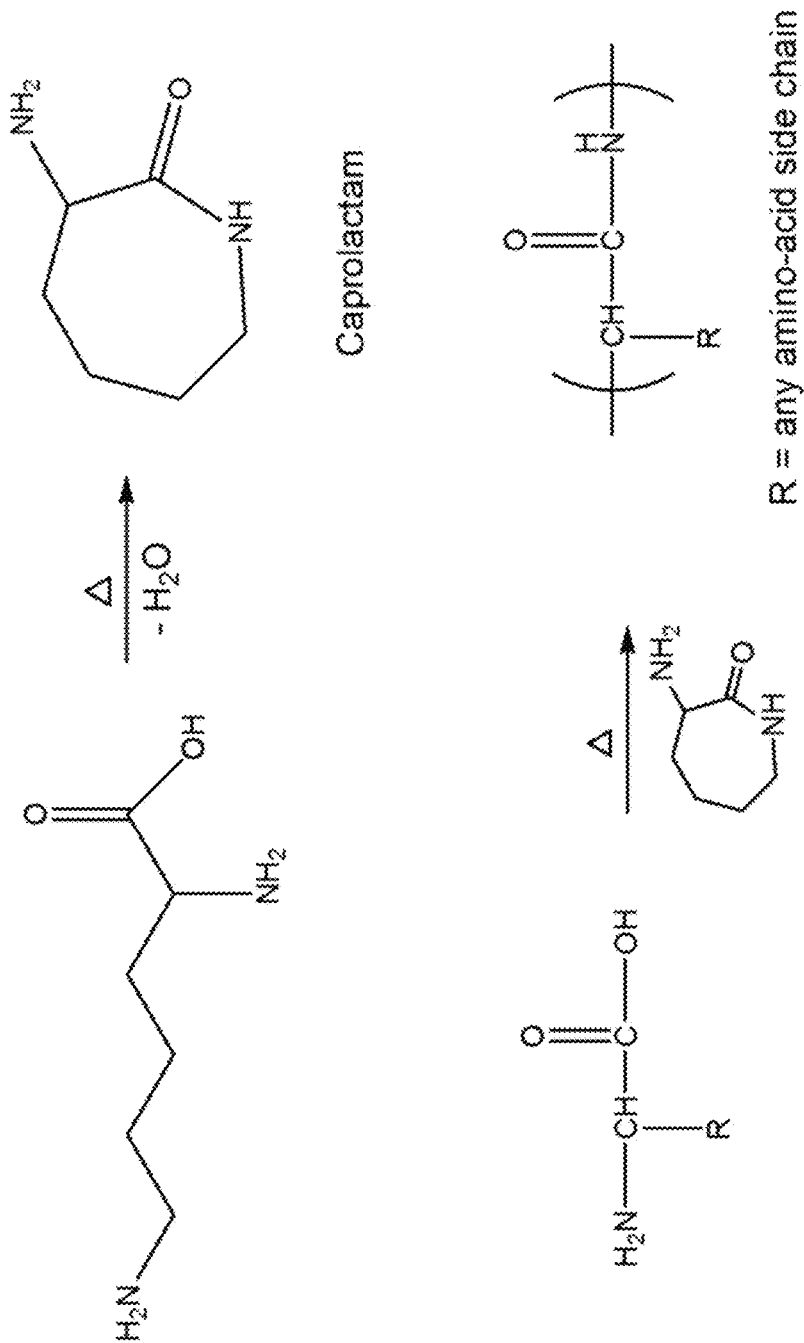

FIG. 23 presents a scheme showing thermal polymerization of amino acids through caprolactam catalysis.

FIGS. 24A-F present hydrodynamic size histogram and SEM images of particles formed from ProtA3 (as designated below) with initial concentrations of 1 mg/mL (FIG. 24A, FIG. 24B), 2 mg/mL (FIG. 24C, FIG. 24D) and 2.5 mg/mL (FIG. 24E, FIG. 24F) in purified water.

Figure 25:
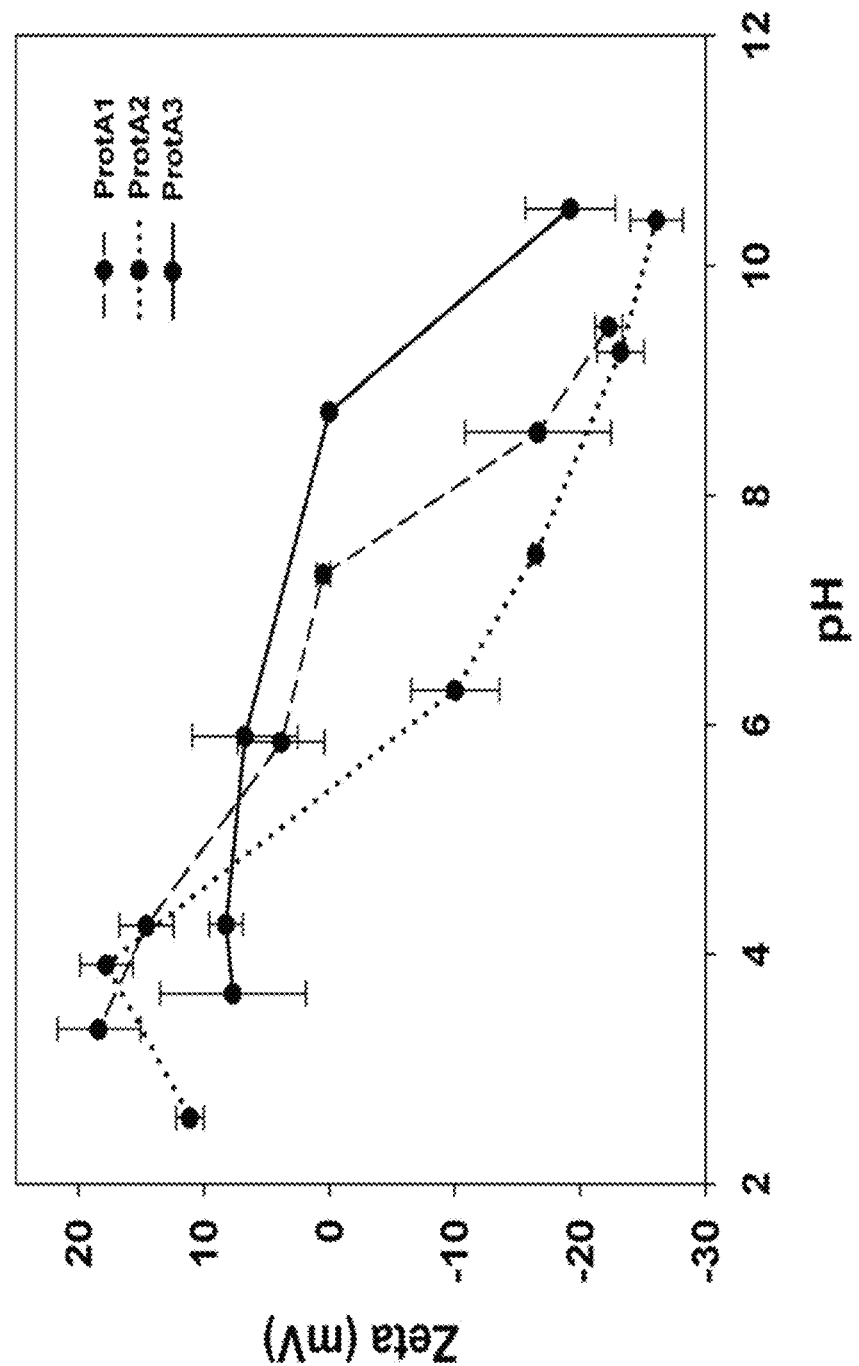

FIG. 25 presents zeta potential of proteinoid particles. Each data point for zeta potentials was an average of at least 5 measurements.

Figures 26A, 26B:
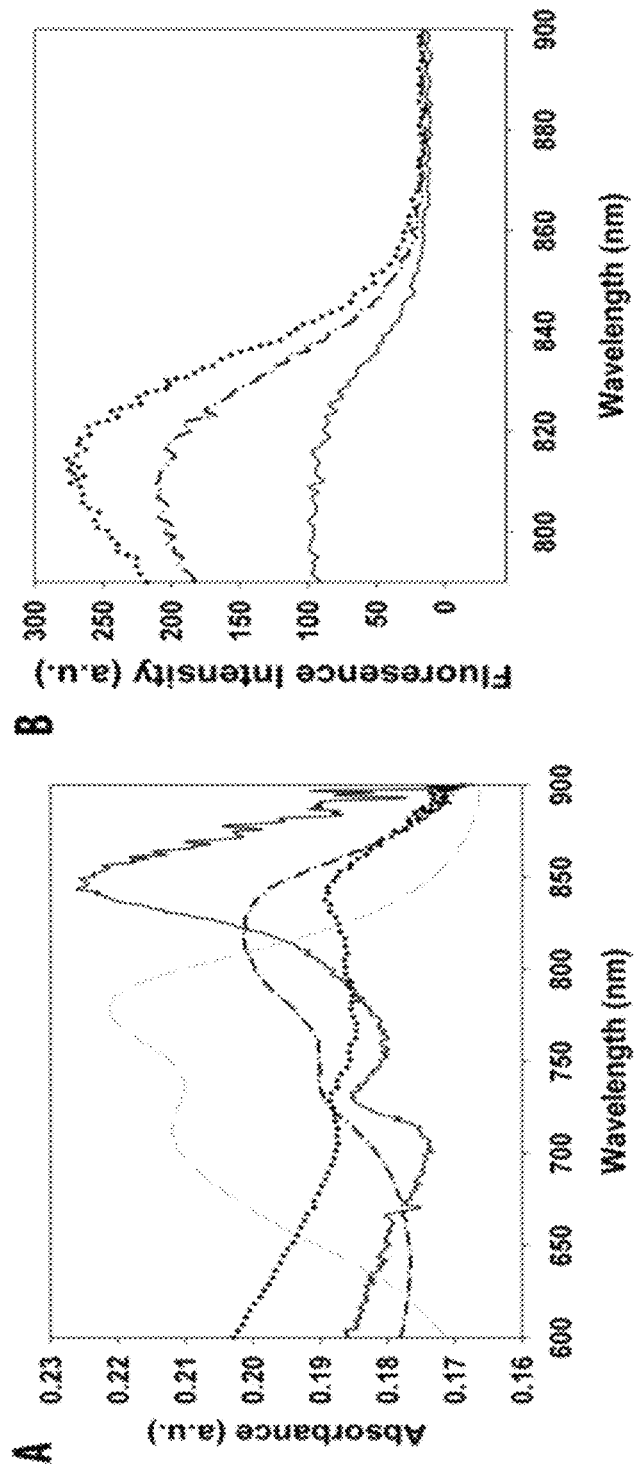

FIGS. 26A-B present the absorbance (FIG. 26A) and emission (FIG. 26B) spectra of ICG-encapsulated particles of ProtA1 (solid lines), ProtA2 (dash dotted lines), ProtA3 (dotted lines) and absorbance spectra of free ICG (dashed line).

Figure 27B:
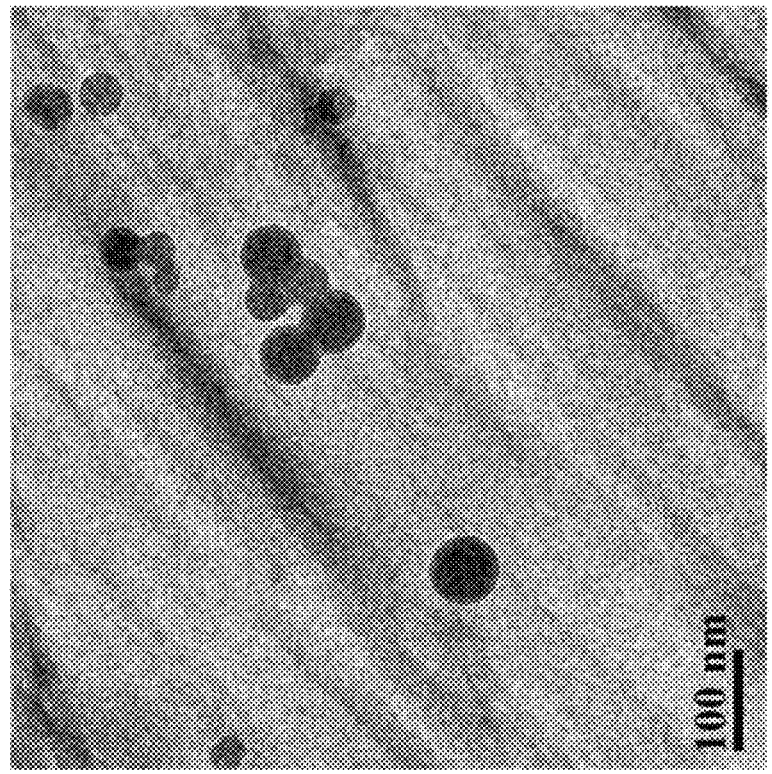
Figure 27A:
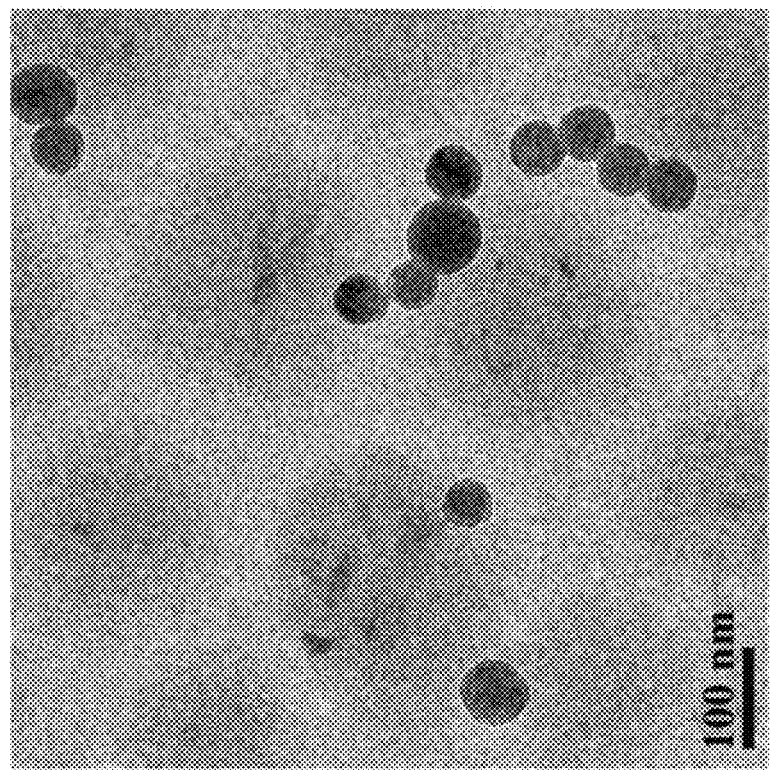

FIGS. 27A-B present Cryo-TEM images of hollow (FIG. 27A) and 15% Dox-encapsulated (FIG. 27B) ProtC6 NPs (as designated below).

Figure 28:
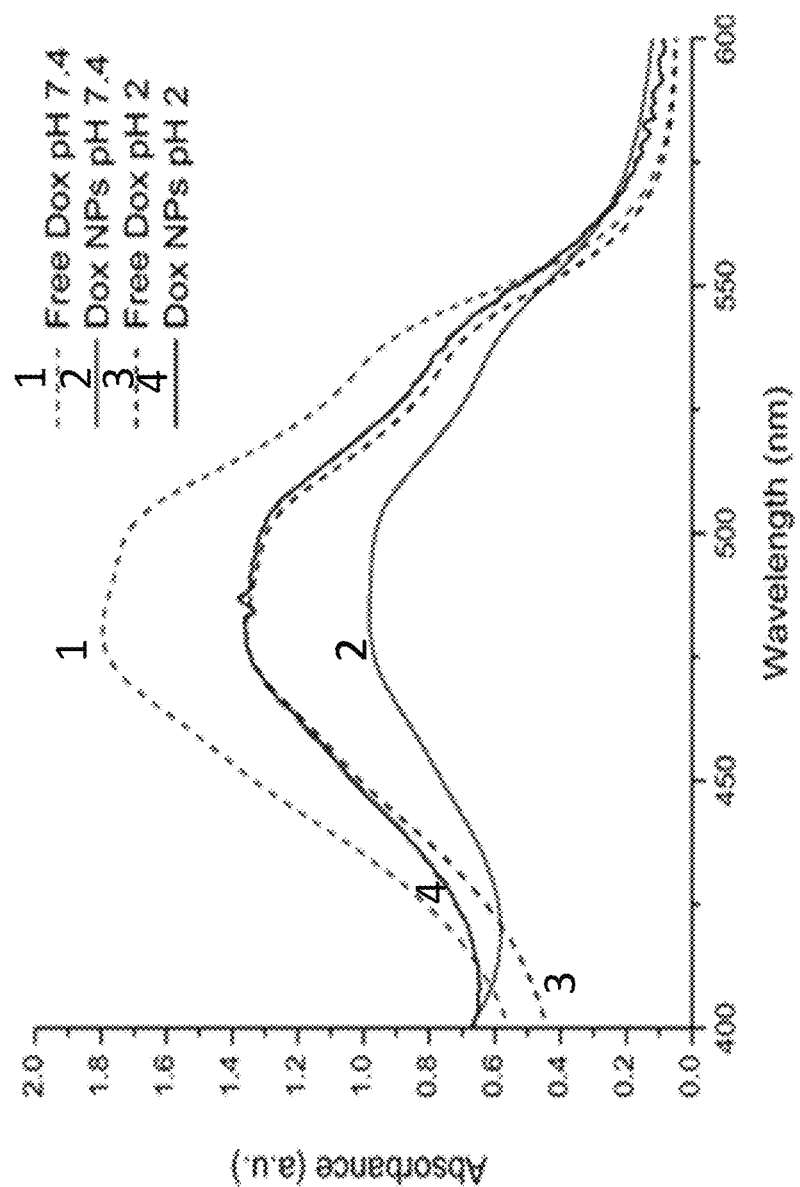

FIG. 28 presents UV-visible light absorption of free Dox (dashed lines), and 15% Dox-encapsulated NPs (solid lines) at pH 7.4 ("1" and "2") and pH 2 ("3" and "4").

Figure 29:
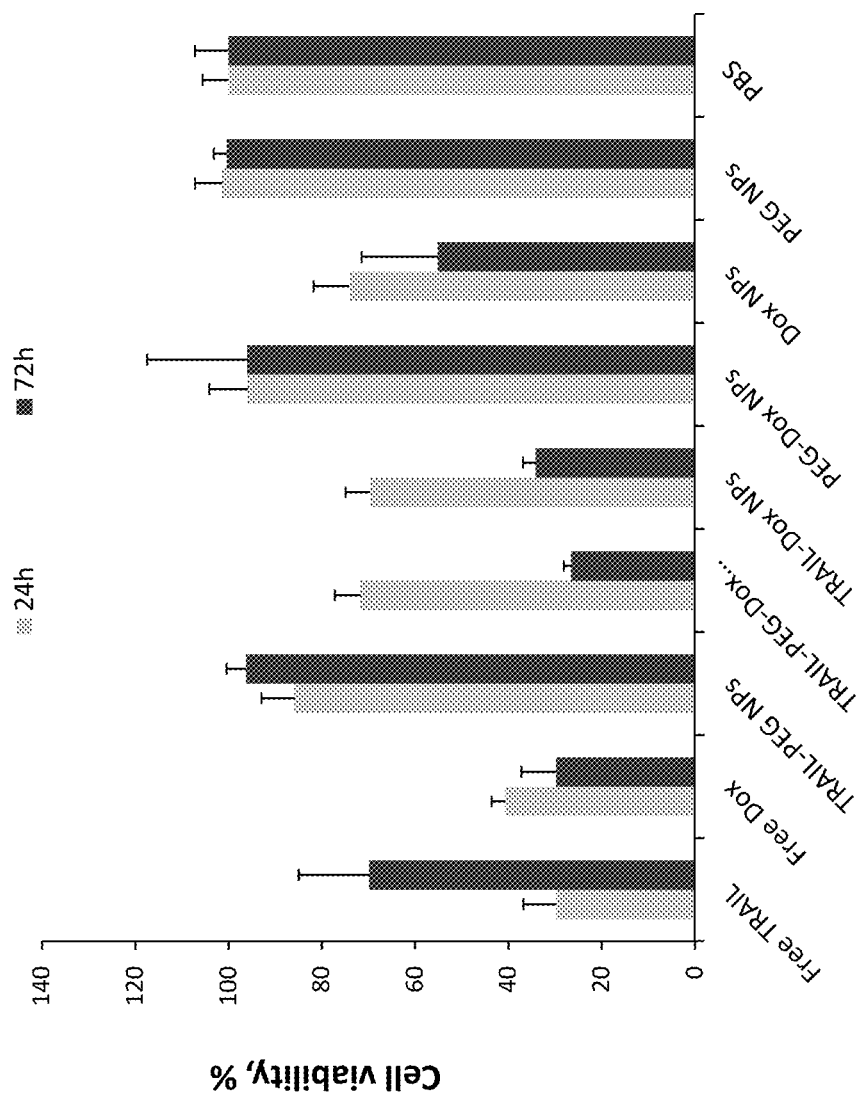

FIG. 29 presents cell viability by XTT assay on HCT116 24 h (left bar in each couple) and 72 h (right bars) after treatment. The cells were treated with 0.01 mg/mL NPs, hollow or containing 1.6 µg Dox, non-conjugated and conjugated to 35 ng TRAIL, free Dox, free TRAIL and PBS. TRAIL: TNF-related apoptosis-inducing ligand.

Figure 30:
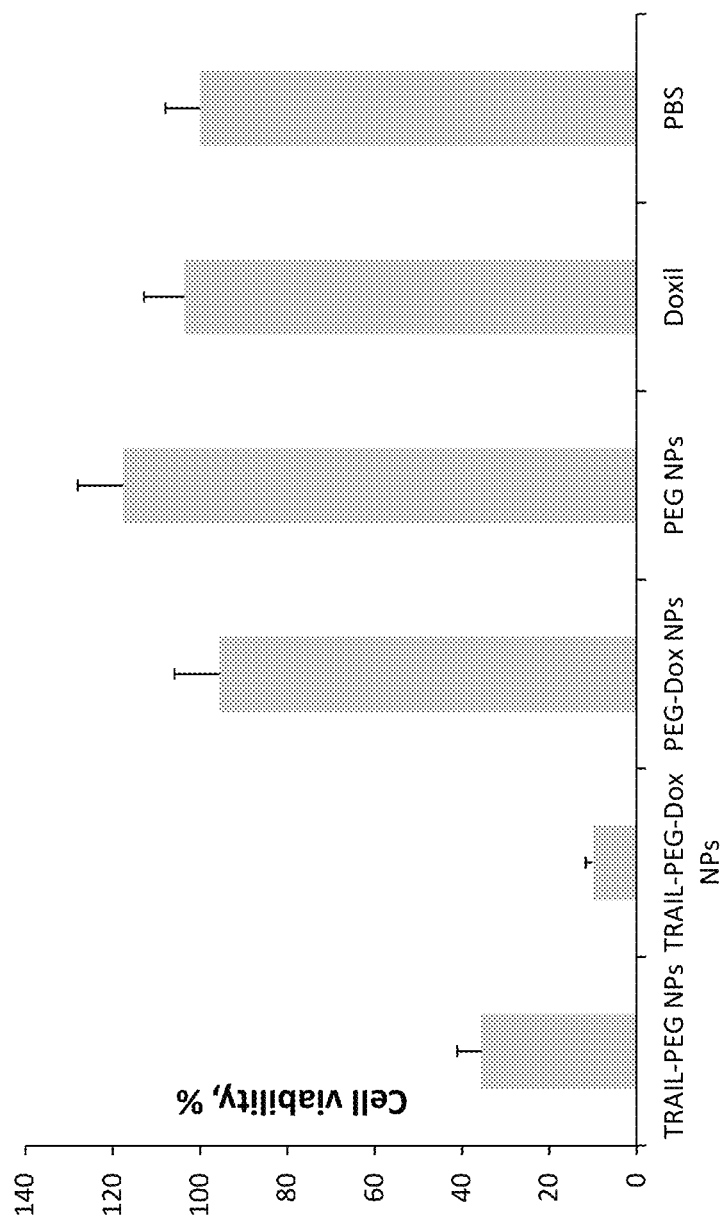

FIG. 30 presents cell viability by XTT assay on HCT116 24 h after treatment. The cells were treated with 0.05 mg/mL NPs and Doxil. PBS served as control.

Figure 31:
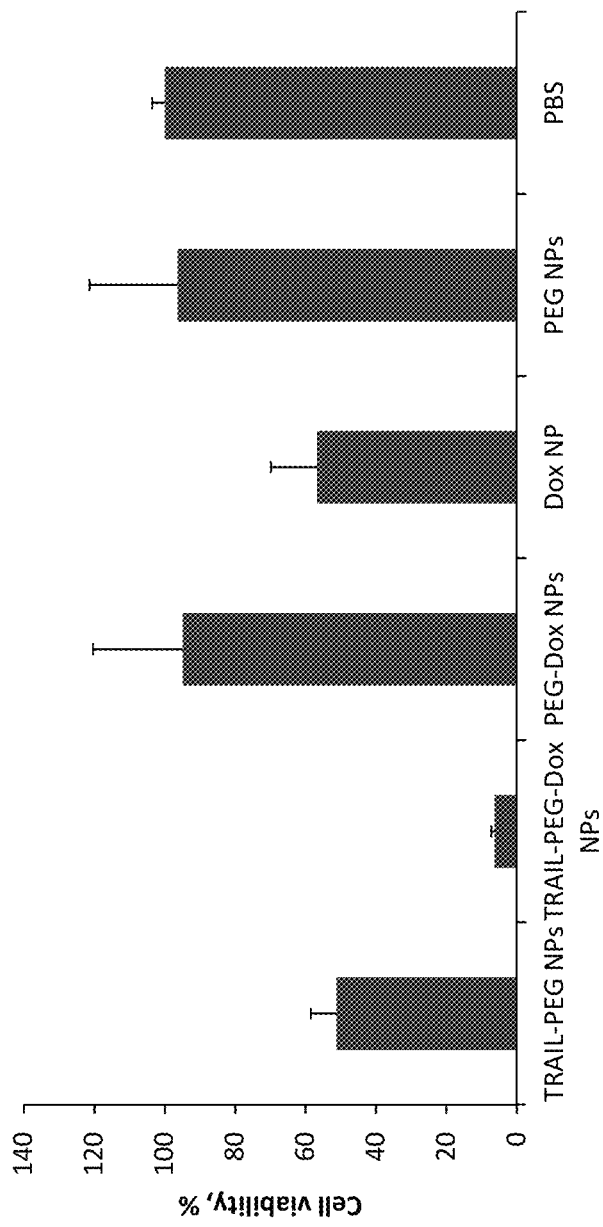

FIG. 31 presents cell viability by XTT assay on 4T1 72 h after treatment. The cells were treated with 0.05 mg/mL NPs. PBS served as control.

Figure 32:
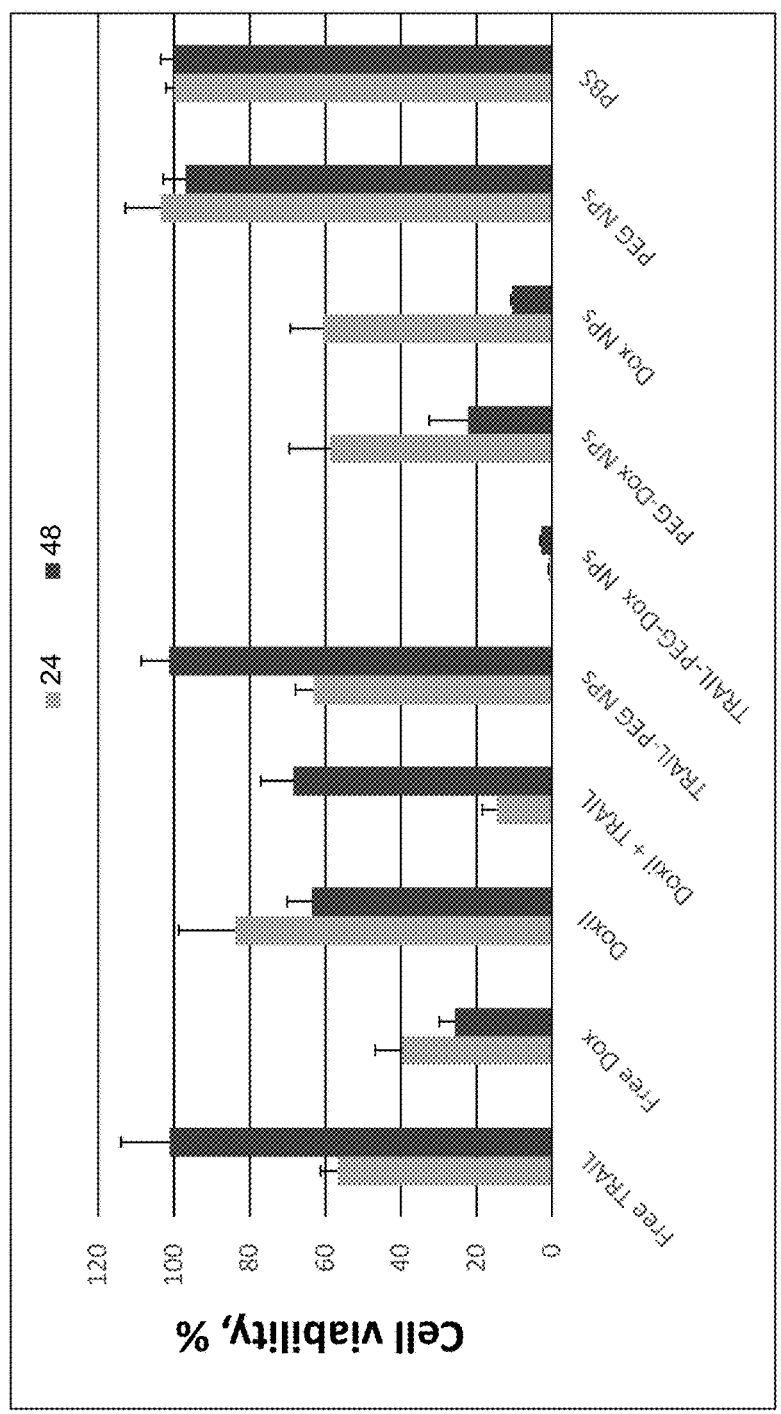

FIG. 32 presents cell viability by XTT assay on A172 24 and 48 h (left and right bars in each couple, respectively) after treatment. The cells were treated with 0.05 mg/mL NPs, an equivalent amount Dox-containing commercial Doxil (8.3 µg Dox), free TRAIL, free Dox and a combination of Doxil and free TRAIL. PBS served as control.

Figure 33:
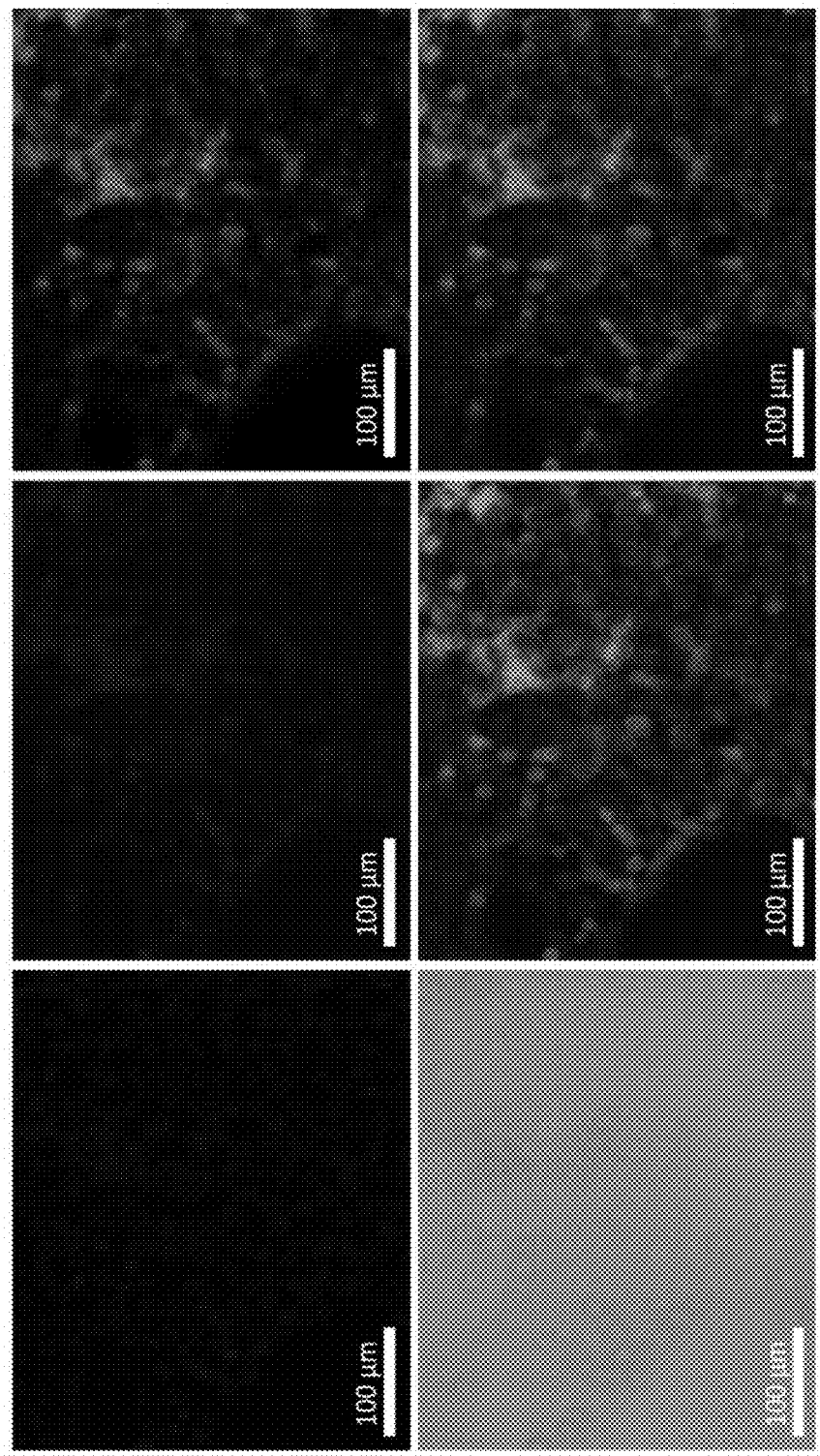

FIG. 33 presents uptake of TRAIL-PEG-Dox NPs containing a NIR fluorescent dye Cy7 on the surface in HCT116 cells. HCT116 cells were incubated for 4 h with Cy7 fluorescent TRAIL-PEG-Dox NPs (0.02 mg/ml). Images were taken using fluorescent microscopy. The nucleus is seen in blue (upper left) (4',6-diamidino-2-phenylindole; DAPI), red (upper middle) represents Dox in NPs, green represents cy7 NPs, bright field and merged fluorescent images.

Figure 34:
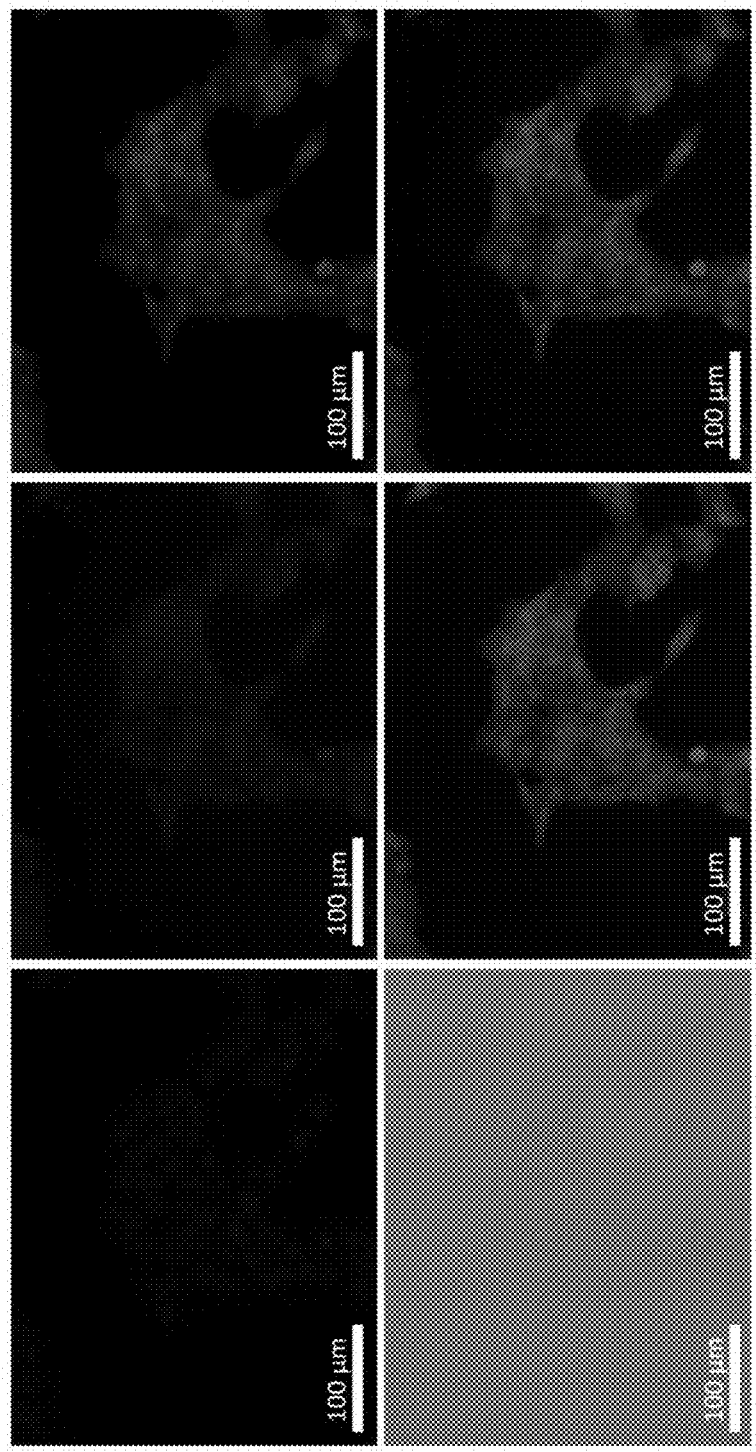

FIG. 34 presents uptake of TRAIL-PEG-Dox NPs containing a NIR fluorescent dye Cy7 on the surface in HCT116 cells. HCT116 cells were incubated for 24 h with Cy7 fluorescent TRAIL-PEG-Dox NPs (0.02 mg/ml). Images were taken using fluorescent microscopy. The nucleus is seen in blue (upper left) (DAPI), red (upper middle) represents Dox in NPs, green represents cy7 NPs, bright field and merged fluorescent images.

DETAILED DESCRIPTION OF THE INVENTION

The present invention, in some embodiments thereof, relates, inter alia, to proteinoid compounds characterized by a molecular weight (Mw) of at least 15,000 Da, to processes of preparing such compounds and to uses thereof.

The principles and operation of the proteinoid compounds, compositions, use, methods and processes according to the invention may be better understood with reference to the drawings and accompanying descriptions in the appendixes as disclosed herewith.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

A proteinoid compound may be used as a polymeric carrier in drug delivery system designed for targeting, e.g., exploitation of the distribution pattern of a drug-carrier in vivo. Attachment of drugs to polymeric carriers typically imparts, inter alia, limited cellular uptake to the endocytic route; improved drug targeting to the tumor; reduce drug toxicity; and overcoming the mechanisms of drug resistance.

The Compositions-of-Matter

According to an aspect of some embodiments of the present invention there is provided a proteinoid compound comprising a polymeric backbone, wherein the polymeric backbone comprises monomeric units, each of the monomeric units being derived from an amino acid, and wherein the polymeric backbone is characterized by a molecular weight (Mw), in some embodiments, of at least 15,000 Da.

Proteinoid are known in the art as being preparable by a thermal condensation reaction from chosen amino acids, such as by synthetic or man-made reactions. Typically, proteinoids lack a defined secondary structure or tertiary structure. One skilled in the art will appreciated that proteinoids are not naturally occurring polypeptides.

The term "condensation reaction", also referred to in the art as "step-growth process", and the like, means reaction to form a covalent bond between organic functional groups possessing a complementary reactivity relationship, e.g., electrophile-nucleophile. Typically, the process may occur by the elimination of a small molecule such as water or an alcohol. Additional information may be found in G. Odian, Principles of Polymerization, 3rd edition, 1991, John Wiley & Sons: New York, p. 108.

As used herein throughout, the term "polymer" describes an organic substance composed of a plurality of repeating structural units (backbone units) covalently connected to one another.

Proteinoid compounds which are suitable for use in the context of the present embodiments are biocompatible, non-immunogenic and non-toxic.

A proteinoid compound may be a biostable polymer. The term "biostable", as used in this context of embodiments of the invention, describes a compound or a polymer that remains intact under physiological conditions (e.g., is not degraded in vivo).

A proteinoid compound may be a biodegradable polymer.

The term "biodegradable" describes a substance which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that e.g., 50 weight percent of the substance decompose within a time period shorter than one year.

The term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

A proteinoid compound may comprise a combination of biostable polymers and of biodegradable polymers.

The proteinoid compound may be water-soluble or water-insoluble. In some embodiments, the polymers are water soluble at a defined temperature range e.g., at room temperature, at 20° C. to 80° C., or at 50° C. to 100° C. The term "water-soluble", or "soluble", as used herein, means the nature with which a proteinoid is not easily precipitated in an aqueous solution and does not easily form inclusion bodies or other aggregates.

The proteinoid compound can further be charged polymers or non-charged polymers. Charged polymers can be cationic polymers, having positively charged groups and a positive net charge at a physiological pH; or anionic polymers, having negatively charged groups and a negative net charge at a physiological pH. Non-charged polymers can have positively charged and negatively charged group with a neutral net charge at physiological pH, or can be non-charged.

In some embodiments, the proteinoid compound is soluble within a defined pH range.

In some embodiments, the defined pH range is basic pH, higher than 7, e.g. 8, 9, 10, 11, 12, 13, 14, including any value therebetween. In some the defined pH range is acidic, lower than 7, e.g., 1, 2, 3, 4, 5, 6, including any value therebetween. In some embodiments, the defined pH range is about 7.

In some embodiments, the solubility in an aqueous solution at various pH is dependent on the structure of the amino acid monomeric units, e.g., the hydrophobic/hydrophilic ratio and the net charge of the proteinoids at different pH. Typically, increasing the temperature leads to increase solubility.

In some embodiments, the proteinoid compound has a weight average molecular weight ($M_W$) in the range of 12,000 Da to 200 kDa. In some embodiments, the polymer has $M_W$ lower than 60 kDa. In some embodiments, the polymer's weight average molecular weight range is 15 to 60 kDa.

The polymeric backbone is derived from, or corresponds to an amino acid.

By "derived from, or corresponds to an amino acid" it is meant to refer to amino acid residue.

The term "amino acid" (or "amino acids", also referred to as "amino acid type(s)") is understood to include, without being limited thereto, the twenty naturally occurring amino acids, as known in the art. Furthermore, unless stated otherwise, the term "amino acid" may refer to both D- and L-amino acids. Non-conventional or modified amino acids (e.g., synthetic), are also conceivable, in some embodiments of the invention, including, for example, para-amino benzoic acid.

In some embodiments, the polymeric backbone is co-polymer, comprising, in each instance, the amino acid is selected from Glu, Lys, Asp, Arg, Tyr, His, Ala, Phe, Cys, Ile, and p-amino benzoic acid.

The term "co-polymer" as used herein, refers to a polymer of at least two chemically distinct monomers.

In some embodiments, the polymeric backbone further comprises polyester.

In some embodiments, the polyester has molecular weight of e.g., 100 Da, 200 Da, 300 Da, 400, Da 500 Da, 600 Da, 700 Da, 800 Da, 900 Da, 1 kDa, 2 kDa, 3 kDa, 4 kDa, 5 kDa, 6 kDa, 7 kDa, 8 kDa, 9 kDa, 10 kDa, 20 kDa, 30 kDa, 40 kDa, 50 kDa, 60 kDa, 70 kDa, 80 kDa, 90 kDa, 100 kDa, including any value therebetween.

Non-limiting examples of polyester which may be used include: aliphatic polyesters, copoly(ether-esters), polyorthoesters, polyoxaesters, polyamidoesters, polyoxaesters containing amine groups, α,ω-hydroxyl, carboxyl compounds, poly(lactic-co-glycolic acid) and combinations thereof.

Additional non-limiting examples of polyester include: polylactide, polyglycolide, polycaprolactone, polyhydroxyalkanoate.

In exemplary embodiments, the polyester is polylactic acid (PLA) e.g., poly(L-lactic acid denoted herein throughout as "PLLA"). Without being bound by any particular theory, it is to note that the incorporation of the polyester in the backbone of the proteinoids may result in the formation of a smaller hydrodynamic size of proteinoid (e.g., proteinoid particles) dispersed in aqueous solution and/or highly degradable proteinoid due to the increased hydrophobicity nature of the proteinoids.

Herein, the term "polyester" is also meant to include one monomeric unit, or oligomer comprising more than one monomeric unit, from which the corresponding polymeric backbone may, or is, derived from. That is, in some embodiments, the polymeric backbone of the proteinoid comprises 1, 2, 3, 4, 5, 6, 7, 8, 9, 10, or more, monomeric units correspond to, or are derived from, polyester. In some embodiments, at least one monomeric unit corresponds to, or derived from polyester is not linked to another monomeric unit corresponds to, or derived from, polyester.

In some embodiments, the polymeric backbone of the proteinoid is represented by the following formula (I) also termed hereinthroughout as "acid proteinoid":

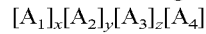

wherein:

$A_1$ is, in each instance, selected from Glu and Lys;

$A_2$, and $A_3$ are each, independently, a monomeric unit derived from an amino acid or are each, independently, absent;

$A_4$ represents a backbone corresponding to, or derived from, polyester, or is absent;

x, y, and z are integers, independently, representing the total numbers of $A_1$, $A_2$, and $A_3$, respectively, in the polymeric backbone, such that x+y+z has a value of at least 100.

For example, a proteinoid comprising aspartic acid may comprise 2 to 100 aspartic acid residues. Therefore, such proteinoid may comprise e.g., 2, 3, 4, 5, 6, 7, 8, 9, 10, 11, 12, 13, 14 15, 16, 17, 18, 19, 20, 25, 30, 35, 40, 45, 50, 55, 60, 65, 70, 75, 80, 85, 90, 95, 100 etc, including any value and range therebetween.

Exemplary types of proteinoid compounds are disclosed hereinthroughout under "The Process".

In some embodiments, the polyester is at least 1%, 2%, 3%, 4%, 5%, 6%, 7%, 8%, 9%, 10%, 11%, 12%, 13%, 14%, 15%, 16%, 17%, 18%, 19%, 20%, 30%, 40%, including any value therebetween, by weight, of the polymeric backbone.

In exemplary embodiments, the amino acid in formula I is selected from the group consisting of: Asp, Lys, Arg, and Phe.

In exemplary embodiments, $A_1$ is Glu, $A_2$ is Phe and $A_3$ is absent.

In still further exemplary embodiments, $A_1$ is Glu, $A_2$ is Asp, and $A_3$ is selected from the group consisting of: Lys, Phe, or is absent.

In still further exemplary embodiments, $A_1$ is Glu, $A_2$ is Lys, and $A_3$ is absent.

In still further exemplary embodiments, $A_1$ is Glu, $A_2$ is Lys, and $A_3$ is Phe.

In some embodiments, the polymeric backbone of the proteinoid is represented by the following formula also termed hereinthroughout as "basic proteinoid":

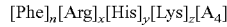

wherein:

$A_4$ represents the polyester or is absent;

n, x, y, and z are integers, independently, representing the total numbers of Phe, Arg, His, and Lys, respectively, in the polymeric backbone, such that n+x+y+z has a value of at least 100.

In some embodiments, the composition further comprises cysteine. In some embodiments, the composition further comprises PABA.

Exemplary types of basic proteinoid compounds are disclosed herein in the Examples section.

In some embodiments, the polyester is at least 1%, 2%, 3%, 4%, 5%, 6%, 7%, 8%, 9%, 10%, 11%, 12%, 13%, 14%, 15%, 16%, 17%, 18%, 19%, 20%, including any value therebetween, by weight, of the polymeric backbone.

In some embodiments, $A_4$ is absent. In some embodiments, $A_4$ is polylactide (e.g. PLLA).

It would be appreciated that n, x, y, and z, can be controlled as desired by selecting the mol ratio of the respective monomeric units used for forming the proteinoid.

Further examples of basic proteinoids are described in the Examples section.

In some embodiments, there is provided a composition-of-matter comprising a plurality of the disclosed proteinoid compounds.

In some embodiments, at least e.g., 50%, 60%, 70%, 80%, 90% or 99% of plurality of the disclosed proteinoid compounds is characterized by a low dispersity index (Ð). In some embodiments, the low dispersity index (Ð) has a value which is lower than a typical Ð of a plurality of polymers derived from a step-growth condensation.

As used herein, "dispersity index", also termed in the art: "polydispersity index" (denoted hereinthroughout as: "Ð") refers to a measure of the distribution of molecular mass in a given polymer sample. The dispersity index is calculated by dividing the weight average molecular weight (Mw) by the number average molecular weight (Mn). As used herein, the term "weight average molecular weight" generally refers to a molecular weight measurement that depends on the contributions of polymer molecules according to their sizes. As used herein, the term "number average molecular weight" generally refers to a molecular weight measurement that is calculated by dividing the total weight of all the polymer molecules in a sample with the total number of polymer molecules in the sample. These terms are known by those of ordinary skill in the art.

Ð has a value always greater than 1, but as the polymer chains approach uniform chain length, the value of Ð approaches unity (1). Homogenous size distribution of the proteinoids may contribute, inter alia, to a more defined biodistribution.

As used herein "low Ð value" refers to a value below 1.6, or in some embodiments, below 1.5. For example a "low Ð value" may be 1.59, 1.58, 1.57, 1.56, 1.55, 1.54, 1.53, 1.52, 1.51, 1.5, 1.49, 1.48, 1.47, 1.46, 1.45, 1.44, 1.43, 1.42, 1.41, 1.4, 1.39, 1.38, 1.37, 1.36, 1.35, 1.34, 1.33, 1.32, 1.31, 1.3, 1.29, 1.28, 1.27, 1.26, 1.25, 1.24, 1.26, 1.25, 1.24, 1.23, 1.22, 1.21, 1.2, 1.19, 1.18, 1.17, 1.16, 1.15, 1.14, 1.13, 1.12, 1.11, 1.1, 1.09, 1.08, 1.07, 1.06, 1.05, 1.04, 1.03, 1.02, 1.01, or 1.005, including any value therebetween.

In some embodiments, Ð may be further reduced by increasing the %, of the polyester in the proteinoid compound.

As described hereinthroughout, and without being bound by any particular theory, the narrow size distribution of the proteinoids and the proteinoids-polyesters dictates the formation of narrower size distribution of nano- or micro-proteinoid particles, as described hereinbelow, via a self-assembly process.

In some embodiments, at least one proteinoid is in form of hollowsphere.

As used herein the term "hollowsphere", or "proteinoid hollowsphere", refers to any polymer having at least one void space in the primary polymeric structure. The term hollowsphere is used only for the purpose of illustration and it is to be construed that is not only limited to spherical shape but also includes any shape which may find suitability to at least some embodiments of the present invention. By "void space" herein it is meant to refer to a polymer-free space or a central cavity, typically filled with water e.g., in aqueous dispersion or with air in the dried hollowsphere.

In the context of the current disclosure, groups on the proteinoid results in the generation of a hydrophobic core inside of the hollow sphere.

In some embodiments, the proteinoids are dissolved in an aqueous solution. In some embodiments, the proteinoids may become insoluble e.g., via a self-assembly process. In some embodiments, the proteinoids are characterized by the hydrophobic part being within the core of the hollowsphere and the hydrophilic residues being exposed towards the aqueous solution.

In some embodiments, the hollowsphere (e.g., in the form of particle) is characterized by a hydrophilic shell.

In some embodiments, the hollowsphere is characterized by a hydrophilic shell and a hydrophobic core.

In some embodiments, each of the proteinoid compounds further comprises one or more agents selected from, but are not limited to: labeling compound (agent), UV blocker, an antibacterial compound, a magnetite, an antioxidant, filler, biologically active agent (e.g., an antibody). In some embodiments, one or more agents are attached to and/or encapsulated within the hollowsphere. In some embodiments, the agent is attached to a surface of the proteinoid or the hollowsphere.

The agent may be attached to the polymeric backbone either directly, or by means of a spacer. In exemplary embodiments, the spacer is polyethylene glycol (PEG).

In some embodiments, the agent is hydrophobic. In some embodiments, the hydrophobic agent is characterized by a degree of polarity which is satisfactory to allow encapsulation thereof within the hydrophobic core of the proteinoid hollowsphere.

It is noteworthy that, for example, the proteinoids and the proteinoids-polyesters possess also many functional groups on the surface, e.g., amines, hydroxyls, carboxyls and thiols, which may be used for physical or covalent conjugation of biomolecules on the surface of these proteinoids.

Alternatively, the agent may be attached to a portion of the backbone units forming the polymeric backbone, directly or via a spacer. Alternatively, the agent may be encapsulated within the void space as described hereinabove.

As used herein, the phrase "labeling agent" or "labeling compound" describes a detectable moiety or a probe. Exemplary labeling agents which are suitable for use in the context of these embodiments include, but are not limited to, a fluorescent agent, a radioactive agent, a near IR dye (e.g., indocyamine green), a rhodamine dye, a fluorescein dye, a magnetic agent or nanoparticle, a chromophore, a photochromic compound, a bioluminescent agent, a chemiluminescent agent, a phosphorescent agent and a heavy metal cluster.

An attachment of a labeling agent to the proteinoids, enables utilizing these proteinoids for monitoring disease or disorders, for example, monitoring the therapeutic effect exhibited by the proteinoid comprising a drug, as described herein.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}Tc$ $^{18}F$, $^{131}I$ and $^{125}I$.

The term "magnetic agent" describes a substance which is attracted to an externally applied magnetic field. These substances are commonly used as contrast media in order to improve the visibility of internal body structures in Magnetic resonance imaging (MRI). The most commonly used compounds for contrast enhancement are gadolinium-based. MRI contrast agents alter the relaxation times of tissues and body cavities where they are present, which depending on the image weighting can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process The term "chemiluminescent agent" describes a substance which emits light as the result of a chemical reaction.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

In some embodiments, the biologically active agent is selected from, but is not limited to, anticancer drug (e.g., doxorubicin, also referred to as "Dox") or combination of drugs (e.g. doxorubicine and TRAIL), benzoyl peroxide, retinoic acid, monoclonal antibody, siRNA, RNA, microRNA, DNA, a plasmid a bisphosphonate, antibacterial or an antifungecide reagent. Herein, in the context of encapsulation, the proteinoid may be acidic or basic. In exemplary embodiments, the proteinoid comprises L-Lys, L-His, L-Arg, L-Phe and PLLA. In some embodiments, one or more the biologically active agents act in synergism in the disclosed composition (e.g., in the form of a particle).

In some embodiments, the agent (e.g., Dox) is e.g., 1%, 2%, 5%, 10%, 15%, 20%, 25%, 30%, 35%, 40%, 50%, by weight, including any value therebetween. Herein, by weight refers to the total weight of the compounds or composition.

In exemplary embodiments, Dox is encapsulated in proteinoid nanoparticles. In additional exemplary embodiments, proteinoid nanoparticles encapsulating Dox were conjugated with spacers (PEG). In additional exemplary embodiments, proteinoid nanoparticles encapsulating Dox were conjugated with spacers (PEG) were conjugated with TRAIL.

The phrase "bioactive agent", which, in some embodiments, is interchangeably referred to as "drug", describes a compound which exhibits a beneficial pharmacological effect when administered to a subject and hence can be used in the treatment of a condition that benefits from this pharmacological effect.

The term "subject" (alternatively referred to herein as "patient") as used herein refers to an animal, preferably a mammal, most preferably a human, who has been the object of treatment, observation or experiment.

The phrase "anticancer agent" or "anticancer drug", as used herein, describes a therapeutically active agent that directly or indirectly kills cancer cells or directly or indirectly inhibits, stops or reduces the proliferation of cancer cells. Anti-cancer agents include those that result in cell death and those that inhibit cell growth, proliferation and/or differentiation. In some embodiments, the anti-cancer agent is selectively toxic against certain types of cancer cells but does not affect or is less effective against normal cells. In some embodiments, the anti-cancer agent is a cytotoxic agent.

The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor which is not self-limited in its growth, is capable of invading into adjacent tissues, and may be capable of spreading to distant tissues (metastasizing). The term "benign tumor" describes a tumor which is not-malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

Hematologic malignancies include leukemia, lymphoma, and multiple myeloma. The following are non-limiting examples of the cancers treatable with the proteinoids described herein: ovarian, pancreas, brain, colon, rectal, colorectal, melanoma, lung, breast, kidney (renal), and prostate cancers.

The term "cancer metastases" describes cancer cells which have "broken away", "leaked", or "spilled" from a primary tumor, entered the lymphatic and/or blood vessels, circulated through the lymphatic system and/or bloodstream, settled down and proliferated within normal tissues elsewhere in the body thereby creating a secondary tumor.

In some embodiments, there is provided a composition-of-matter comprising a plurality of proteinoid hollowspheres as disclosed herein. In some embodiments, the hollowspheres are in the form of particles.

The term "particle" herein may be referred to as, without limitation, a spherical particle, a rod-like particle, a disk-like particle, a polygonal particle or a combination thereof.

In some embodiments, the proteinoid particles form a powder. In some embodiments, the proteinoid particles are in form of dry particles or a dry powder. In some embodiments, the proteinoid particles may be wetted and re-dried.

The term "powder" means a composition that consists of finely dispersed solid particles that are free flowing and capable of being readily dispersed.

In some embodiments, at least 70% of the hollowspheres (or particles) are characterized by a hydrodynamic size that ranges from 10 nm to 10 µm. In some embodiments, at least 80% of the particles are characterized by a hydrodynamic size that ranges from 10 nm to 10 µm. In some embodiments, at least 90% of the particles are characterized by a hydrodynamic size that ranges from 10 nm to 10 µm. In some embodiments, at least 80% of the hollowspheres are characterized by a hydrodynamic size that ranges e.g., from 10 nm to 10 µm, or from 10 nm to 1 µm, or from 20 nm to 500 nm, or from 50 nm to 100 nm, or from 10 nm to 50 nm, or from 100 nm to 1 µm.

In some embodiments, a plurality of proteinoid hollowspheres as disclosed herein is characterized by a narrow hydrodynamic size distribution.

As used herein "narrow hydrodynamic size distribution" is characterized by e.g., at least 60%, at least 70%, at least 80%, at least 90%, of the particles having a hydrodynamic size that varies within a range of less than 25% average hydrodynamic diameter.

In some embodiments, the "narrow hydrodynamic size distribution" is characterized by size distribution of at least 80% of the particles varying within a range of less than e.g., 60%, 50%, 40%, 30%, 20%, 10%, including any value therebetween.

In exemplary embodiments, the "narrow hydrodynamic size distribution" is characterized by size distribution of at least 80% of the particles varying within a range of less than e.g., 60%, 50%, 40%, 30%, 20%, 10%, including any value therebetween.

In some embodiments, the hydrodynamic size of the particles is affected by % (wt.) of the polyester in the polymeric backbone of the proteinoid. In some embodiments, the % (wt.) of the polyester has a value that ranges from 0% to about 15%. In some embodiments, the % (wt.) of the polyester has a value of 1%, 2%, 3%, 4%, 5%, 60%, 7%, 8%, 9%, 10%, 11%, 12%, 13%, 14%, 15%, 16%, 17%, 18%, 19%, 20%, including any value therebetween.

As exemplified hereinthroughout, the polyester is poly-L-lactic acid.

In exemplary embodiments, the % (wt.) of the poly-L-lactic acid is about 10% and the particle size is about 100 nm.

As noted hereinabove, the amino acids may be racemic or of optical activity—L or D or mixed. Therefore, the proteinoids described herein may possess asymmetric carbon atoms (optical centers) or double bonds; the racemates, diastereomers, geometric isomers and individual isomers are further encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

In some embodiments, the particles are characterized as being optically active. The term "optically active" means that the enantiomeric excess is greater than zero.

In some embodiments, there is provided a pharmaceutical, cosmetic or cosmeceutic product comprising the proteinoid compounds or the composition-of-matter as described herein. In some embodiments, the proteinoid compounds or the composition-of-matter as described herein is incorporated in a pharmaceutical, cosmetic or cosmeceutical formulation or capsule forming the product.

In some embodiments, the product comprises a cosmetic, cosmeceutical or pharmaceutical formulation such as skincare formulations, makeup or dermatological or other topical pharmaceutical formulations, comprising the proteinoid compounds or the composition-of-matter as described herein. The formulation can optionally and preferably further comprise a carrier, and optionally additional active agents and/or additives.

As used herein a "formulation" refers to a vehicle in the form of emulsion, lotion, cream, gel etc., which comprises physiologically acceptable carriers and/or excipients and optionally other chemical components such as cosmetically, cosmeceutically or pharmaceutically active agents (e.g., drugs). The formulation may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and anti-histamine.

As used herein, the term "physiologically acceptable" means approved by a regulatory agency of the Federal or a state government or listed in the U.S. Pharmacopeia or other generally recognized pharmacopeia for use in animals, and more particularly in humans.

Herein, the phrase "physiologically suitable carrier" refers to an approved carrier or a diluent that does not cause significant irritation to an organism and does not abrogate the biological activity and properties of a possible active agent.

Herein, the term "excipient" refers to an inert substance added to a formulation as described herein to further facilitate processes and administration of the active ingredients.

In some embodiment of the present invention, the pharmaceutical, cosmetic or cosmeceutical formulation is formulated in a form suitable for topical application on the applied area.

By selecting the appropriate carrier and optionally other ingredients that can be included in the formulation, as is detailed hereinbelow, it may be formulated into any form typically employed for topical application.

The formulations can be water based, oil based or silicon based.

In some embodiments, the formulations are colloidal formulations, in which the proteinoid compounds or the composition-of-matter as described herein are dispersed, suspended or otherwise distributed in the carrier.

The formulations as described herein can be, for example, skin care products, make-up products (including eye shadows, make-up, lipstick, lacquer, etc., or any other product as described herein).

In some embodiments, a formulation as described is in a form of a cream, an ointment, a paste, a gel, a lotion, a milk, an oil, a suspension, a solution, an aerosol, a spray, a foam, or a mousse.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the sunscreens-containing microcapsules, are present in a water or alcohol base. Lotions are typically preferred for covering/protecting large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, generally comprises petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from single-phase aqueous gels. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

The preparation of the formulation can be carried out by mixing and homogenizing all the ingredients. A product comprising such formulations, as described herein, can be prepared, for example, by contacting the formulation with already prepared proteinoid compounds or the composition-of-matter as described herein.

In any of the formulations described herein, additional agents and/or additives can be included.

Some non-limiting representative examples of additives and/or agents include humectants, deodorants, antiperspirants, sunless tanning agents, hair conditioning agents, pH adjusting agents, chelating agents, preservatives, emulsifiers, occlusive agents, emollients, thickeners, solubilizing agents, penetration enhancers, anti-irritants, colorants, propellants and surfactants.

According to an embodiment of the present invention, the pharmaceutical, cosmetic or cosmeceutic product described hereinabove is packaged in a packaging material and identified in print, in or on the packaging material, for use in the treatment of cancer and/or a medical condition associated with cancer. In some embodiments the cancer is colon cancer.

According to another embodiment of the present invention, the pharmaceutical composition is packaged in a packaging material and identified in print, in or on the packaging material, for use in monitoring cancer and/or a medical condition associated with cancer.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the FDA for prescription drugs or of an approved product insert.

Method of Treatments

According to some embodiments, there is provided a method of monitoring the presence and metastases of cancer in a body of an individual, the method comprising administering to the individual the proteinoid compound or composition-of-matter, comprising one or more agents as disclosed herein, and employing an imaging technique for monitoring a distribution of the compound or composition-of-matter within the body or within a portion thereof.

As further described hereinabove, suitable imaging techniques include but are not limited to positron emission tomography (PET), gamma-scintigraphy, magnetic resonance imaging (MRI), functional magnetic resonance imaging (fMRI), magnetoencephalography (MEG), single photon emission computerized tomography (SPECT) computed axial tomography (CAT) scans, ultrasound, fluoroscopy and conventional X-ray imaging. The choice of an appropriate imaging technique depends on the nature of the labeling agent, and is within the skill in the art. For example, if the labeling agent comprises Gd ions, then the appropriate imaging technique is MRI; if the labeling agent comprises radionuclides, an appropriate imaging technique is gamma-scintigraphy; if the labeling agent comprises an ultrasound agent, ultrasound is the appropriate imaging technique, etc.

According to some embodiments, there is provided a method for treatment of cancer comprising administering the any one of the proteinoid compound (e.g., a proteinoid hollowsphere comprising one or more bioactive agents) or composition-of-matter as disclosed herein to a patient in a need thereof.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating", or any grammatical derivative thereof, is meant to refer to abrogating, substantially inhibiting, slowing or reversing the progression of a condition, substantially ameliorating clinical or aesthetical symptoms of a condition or substantially preventing the appearance of clinical or aesthetical symptoms of a condition.

It is understood that the compound or compositions of the present invention may be administered in conjunction with other drugs, including other anti-cancer drugs, e.g., doxorubicine and TNF-related apoptosis-inducing ligand (TRAIL) as exemplified below. Other combinations are known in the art.

When the treatable condition is cancer the term would encompass any inhibition of tumor growth or metastasis, or any attempt to inhibit, slow or abrogate tumor growth or metastasis. The method includes killing cancer cells by non-apoptotic as well as apoptotic mechanisms of cell death.

It is to note that herein, by targeting a therapeutically active agent via the methodologies described herein, the toxicity of the therapeutically active agent is substantially reduced. Consequently, besides the use of the proteinoids described herein in a clinically evident disease, optionally in combination with other drugs, these proteinoids may potentially be used as a long term-prophylactic for individuals who are at risk for relapse due to residual dormant cancers. The use of non-toxic targeted proteinoids for the treatment of asymptomatic individuals who are at risk for relapse of a cancer, may lead to a major paradigm shift in cancer treatment from current methods where treatment is generally not initiated until the cancer becomes clinically evident.

As described hereinabove, the term "cancer cells" describes a group of cells which display uncontrolled growth (division beyond the normal limits).

As described hereinabove, cancers treatable by the proteinoids described herein (alone or in combination of an active agent, e.g., RA) include, but are not limited to, solid, including carcinomas, and non-solid, including hematologic malignancies as described hereinabove.

In some embodiments, the proteinoids described herein may be applied topically (e.g., for treating skin diseases e.g., acne).

The Process

According to an aspect of some embodiments of the present invention there is provided a process of a proteinoid compound characterized by molecular weight (Mw) of at least 15,000 Da, the process comprising:

heating one or more types of amino acids to a high temperature, under an inert gas, thereby forming a molten content or a mixture of the one or more amino acids;

stirring the molten content or a mixture at a high temperature for a specified time duration, thereby polymerizing a plurality of monomeric units derived from the one or more amino acids in the content or mixture;

bringing the content mixture to a room temperature;
adding water to the content or a mixture, thereby obtaining a proteinoid compound solution; and cleaning the solution to thereby obtain the proteinoid compound.

In some embodiment the step of cleaning is performed by one or more process known in the art, e.g., dialysis.

As used herein, the term "high temperature" refers to temperature that ranges e.g., from about 100° C. to about 200° C., or from about 150° C. to about 200° C., from about 120° C. to about 280° C.

As used herein, the term "room temperature" is defined as a temperature in the range of about 15° C. to about 30° C. In exemplary embodiments, the term "room temperature" refers to about 25° C.

As used herein, "specified time duration" refers to e.g., at least 10 min, at least 20 min, at least 30 min, at least 40 min, at least 50 min, at least 60 min, at least 70 min, at least 80 min, or at least 90 min.

In some embodiments, the polymerizing of the monomeric units is affected at a stirring rate of at least e.g., 5 rpm, 10 rpm, 20 rpm, 30 rpm, 40 rpm, 50 rpm, or 60 rpm, including any value therebetween.

In some embodiments, the heating to high temperature is applied by microwave irradiation As used herein, "microwave irradiation" refers to the process of radiating electromagnetic (EM) waves onto/into a material, wherein the EM radiation has a wavelength from about 0.001 to about 1 meter, and power from about $1\times10^{-1}$ watts up to about $1\times10^{9}$ watts (W). In exemplary embodiments, the microwave irradiation is applied at a power of at least 100 W.

Given the speed of light, microwave radiation has a frequency range from about 300 MHz to about 300 GHz. The source of microwave radiation may include, without being limited thereto, any one of magnetrons, klystrons, traveling-wave tubes, gyrotrons, field-effect transistors, tunnel diodes, Gunn diodes or IMPATT diodes, or any other EM radiation source. Microwaves are known to cause rotation of dipoles in polar molecules, localized heating and acceleration of chemical reactions.

In some embodiments, as noted hereinabove, the proteinoid compound further comprises polyester in a polymeric backbone thereof, and accordingly, the process comprises a step of adding the polyester prior to the stirring step of the molten content or a mixture at a high temperature.

In some embodiments, the process further comprises the steps of:

Dissolving a plurality of the proteinoid compounds in water while maintaining the water at elevated temperature for specified time duration as described hereinabove, thereby obtaining a solution and cooling the solution to thereby obtain proteinoid particles.

By "elevated temperature" it is meant to refer to a temperature of at least e.g., 50° C., 60° C., 70° C., 800° C. or 90° C.

Herein, the term "solution", or and any grammatical derivative thereof, is defined in a broad sense and is meant to refer to an aqueous medium wherein proteinoids (or proteinoids comprising polyesters) are dissolved, dispersed or suspended. In some embodiments, the aqueous medium further comprises a salt (e.g., NaCl).

In some embodiments, the dissolving process is performed in the presence of one or more agents as described herein above (e.g., bioactive agent), thereby obtaining a proteinoid compound having attached thereto, or encapsulated therein, the one or more agents.

As described hereinabove, in some embodiments, the particles are characterized by a hydrodynamic size that ranges from 10 nm to 10 μm.

In some embodiments, the hydrodynamic size and/or the molecular weight of the polymer can be controlled or is affected, at least to some extent by one or more parameters selected from:

the time duration of the heating, a concentration of the salt solution, and a rate of cooling and a rate of stirring, wherein:

the time duration of the heating ranges e.g., from about 20 min to about 80 min, or from about 30 min to about 70 min, or from about 20 min to about 60 min or from about 20 min to about 40 min or from about 30 min to about 80 min;

the concentration of the salt solution ranges e.g., from $10^{-5}$ N to 1 N, from $10^{-4}$ N to 1 N, from $10^{-3}$ N to 1 N, from $10^{-2}$ N to 1 N, from $10^{-2}$ N to 1 N, from $10^{-5}$ N to 0.01 N, from $10^{-5}$ N to 0.1 N, from $10^{-5}$ N to 1 N;

the rate of stirring ranges e.g., from 0 to about 100 rpm, from 10 to about 90 rpm from 20 to about 80 rpm; and the rate of cooling.

In some embodiments, the rate of cooling is performed slowly.

By "cooling is performed slowly" it is meant that the slowing rate is set within a defined range allowing a self-assembly process of the proteinoid. This process allows, inter alia, the proteinoid to form a structure in which the core of the particle has hydrophobic nature while the shell is of hydrophilic nature, as described hereinabove. Without being bound by any particular mechanism, it is assumed that such a structure further allows obtaining the protenoids in form of particles.

Typically, the cooling rate ranges from 0.5° C. per min to 5° C. per min, e.g., 0.5° C., 1° C., 1.50° C., 2° C., 2.5° C., 3° C., 3.50° C., 4° C., 4.5° C., 5° C., including any value therebetween.

General

As used herein the term "about" refers to ±10%.

The terms "comprises", "comprising", "includes", "including", "having" and their conjugates mean "including but not limited to". The term "consisting of means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

EXAMPLES

Reference is now made to the following examples, which together with the above descriptions illustrate some embodiments of the invention in a non-limiting fashion.

Example 1

Materials and Experimental Methods

Materials:

The following analytical-grade chemicals were purchased from commercial sources and were used without further purification: (L)glutamic acid, (L)aspartic acid, (L)lysine and (L)phenylalanine, sodium chloride, sodium hydroxide (NaOH 1N), hydrochloric acid (HCl 1N), human serum albumin (HSA), bovine plasma fibrinogen, toluene, perfluorohexane (PFH), solvent blue 59 and fluorescein from Sigma (Rehovot, Israel); Poly(L-lactic acid) (PLLA) MW 2,000 Da from Polysciences (Warrington, Pa., USA); Minimum Essential Medium (MEM) eagle, Fetal Bovine Serum (FBS), Phosphate Buffered Saline (PBS), 1% glutamine, 1% penicillin/streptomycin and mycoplasma detection kit from Biological Industries (Bet Haemek, Israel); Cytotoxicity detection kit from Roche Diagnostics, USA; Human colon adenocarcinoma LS174t cell line from American Type Culture Collection (ATCC). Water was purified by passing deionized water through an Elgastat Spectrum reverse osmosis system (Elga Ltd., High Wycombe, UK).

Preparation of Proteinoids by Thermal Condensation Polymerization:

(L)glutamic acid was heated to the molten state (180° C.) in an oil bath, under nitrogen atmosphere. The molten mass was stirred at 180° C. for 30 min. To this, different contents of additional (L)amino acids were added to give a total monomer weight of 5-5.01 g, as specified in Table 1 showing amino acid content of the different proteinoids, and kept at 180° C. under nitrogen. The mixture was mechanically stirred at 150 rpm for 3 h. The product is a highly viscous orange-brown paste, which hardens to give a glassy mass when cooled to room temperature. Then, water (10 mL) was added to the crude product, and the mixture was stirred for 20 min. The solution was then intensively dialyzed through a cellulose membrane (3500 Da MWCO) against distilled water. The content of the dialysis tube was then lyophilized to obtain a yellow-white proteinoid powder.

TABLE 1

| | Amino acid content (g)[a] | | | | |
|---|---|---|---|---|---|
| Polymer | (L)Glu | (L)Asp | (L)Lys | (L)Phe | PLLA |
| Prot1 | 5 | — | — | — | — |
| Prot2 | 2.5 | 2.5 | — | — | — |
| Prot2[b] | 0.15 | 0.15 | — | — | — |
| Prot3 | 2.5 | — | — | 2.5 | — |
| Prot4 | 1.25 | 2.5 | — | 1.25 | — |
| Prot5 | 1.67 | 1.67 | 1.67 | — | — |
| Prot6 | 1.67 | — | 1.67 | 1.67 | — |
| Prot7 | 1.25 | — | 2.5 | 1.25 | — |
| Prot8 | 2.25 | — | — | 2.25 | 0.5 |

[a]In all proteinoids made by thermal condensation polymerization the total monomer content was 5-5.01 g;
[b]made by microwave-assisted polymerization.

Polymerization kinetics was studied by collecting proteinoid samples from the reaction vessel at different time periods of the polymerization at 180, 190 and 200° C. The samples were then analyzed by both ninhydrin test for the determination of the primary amine groups content and Biuret test for the determination of the amide groups content of the various proteinoids.

Proteinoid Analysis and Characterization:

Amino acid analysis was carried out using Waters AccQTag method. Before analysis, the material was hydrolyzed by standard acid hydrolysis, using 6 N HCl at 110° C. for 22 h. The molecular weights and polydispersity index of the dried crude proteinoids were determined using Gel Permeation Chromatography (GPC) consisting of a Waters Spectra Series P100 isocratic HPLC pump with an ERMA ERC-7510 refractive index detector and a Rheodyne (Coatati, Calif.) injection valve with a 20 μL loop (Waters, Mass.). The samples were eluted with super-pure HPLC water through a linear BioSep SEC-s3000 column (Phenomenex) at a flow rate of 1 mL/min. The molecular weights were determined relative to poly(ethylene glycol) standards (Polymer Standards Service-USA, Silver Spring, Md.) with a molecular weight range of 100-450000 Da, Human Serum Albumin (HSA, 67 kDA) and bovine plasma fibrinogen (340 kDa), using Clarity chromatography software. The optical activities of the proteinoids were determined using a PE 343 polarimeter (PerkinElmer). All of the measurements were done in water, at 589 nm at 25° C. Fourier Transform InfraRed (FTIR) measurements of the crude proteinoids were done by the Attenuated Total Reflectance (ATR) technique, using Bruker ALPHA-FTIR QuickSnap™ sampling module equipped with Platinum ATR diamond module. The thermal behavior of the proteinoids was determined using Differential Scanning calorimetry (DSC) and Thermo Gravimetric Analysis (TGA) with a TGA/DSC 1 STARe system (Mettler Toledo, Switzerland). The samples were heated between 25-400° C. at a rate of 10° C./min under nitrogen atmosphere.

Carboxyl Group Analysis:

Without being bound by any particular theory, it is believed that the content of free carboxyl groups in the synthesized proteinoids is an essential factor in determining their solubility in different media, thus helping to understand their stability at different sites in the human body with different pHs. In order to determine the free carboxyl groups in the synthesized proteinoids, a titrimetric method was carried out. Briefly, to a known quantity of dry proteinoid, a known excess of 0.05 N NaOH was added, followed by the addition of 37% formaldehyde solution. The unreacted NaOH was back-titrated with standard 0.05 N HCl. A blank titration was also performed. In addition, human serum albumin (HSA) was titrated for comparison.

Preparation of Proteinoids by Microwave-Assisted Polymerization:

Microwave polymerization method was conducted by a Biotage microwave synthesizer (Biotage Initiator™). Briefly, a mixture of (L)glutamic acid and (L)aspartic acid (150 mg each) was sealed in a 2.0-5.0 mL microwave glass vial with a magnetic stirrer. The reaction was irradiated for 60 min at 120° C., at a pressure of 0 to 1 bar and a power of 200 W. The microwave-made Prot2 was cleaned, dried and characterized by the same techniques as mentioned above.

Incorporation of poly(L-lactic acid) into the Proteinoids:

In order to effect the chemical and physical properties of the product, a thermal polymerization of (L)glutamic acid and (L)phenylalanine was carried out in the presence of low molecular weight poly(L-lactic acid) (PLLA, 2000 Da). The proteinoid-PLLA (Prot8) consists of 2.25 g of each amino acid and 0.5 g of PLLA. After polymerization, it was washed, dried and characterized as described earlier.

Preparation and Characterization of Proteinoid Nano/Micro-Particles:

Proteinoid particles were prepared by a self-assembly mechanism. Briefly, 100 mg of the dried proteinoid were added to 10 mL double-distilled water. The mixture was then heated to 80° C. until the crude proteinoid dissolves completely. Proteinoid particles were then formed by removal of the heating and leaving the mixture to cool to room temperature. The size and size distribution of the formed proteinoid particles were controlled by changing various parameters of the self-assembly precipitation process, e.g., salt concentration or cooling rate. The obtained particles were dialyzed as previously described to wash off excess reagents. This effect of salt concentration and cooling rate on the size of the proteinoid particles was studied with Prot3.

Hydrodynamic diameter and size distribution of the particles dispersed in double distilled (DD) water were measured at room temperature with a particle DLS analyzer model Nanophox (SympatecGmbH, Germany). Dried particle size and size distribution were measured with a Scanning Electron Microscope (SEM). SEM pictures were obtained with a JEOL, JSM-840 Model, Japan. For this purpose, a drop of dilute particle dispersion in distilled water was spread on a glass surface, and then dried at room temperature. The dried sample was coated with carbon in vacuum before viewing under SEM. The average particle size and distribution were determined by the measurement of the diameter of more than 200 particles with image analysis software (Analysis Auto, Soft Imaging System GmbH, Germany).

The density of the particles was determined by pycnometry. Briefly, dry pre-weighed particles were put in a calibrated pycnometer, which was then filled with water. The density of the sample can then be calculated from the known density of the water, the weight of the pycnometer filled only with water, the weight of the pycnometer containing both the sample and water, and the weight of the sample, as described in the literature.

Cytotoxicity of the Proteinoid Particles:

In vitro cytotoxicity of the proteinoid particles was tested by using human colon adenocarcinoma L5174T cancer cell line. The tests were done on Prot2, Prot4, Prot5, Prot7 and Prot8. The cell line is adherent to the used culture dishes. L5174T cells were grown in MEM that was supplemented with 10% heat-inactivated fetal bovine serum (FBS), 1% glutamine and 1% penicillin/streptomycin. Cells were screened to ensure they remained mycoplasma-free using Mycoplasma Detection Kit.

Cell cytotoxicity was assessed by measuring the release of cytoplasmic lactate dehydrogenase (LDH) into cell culture supernatants. LDH activity was assayed using the Cytotoxicity Detection Kit according to the manufacturer's instructions. Cells ($3 \times 10^5$ cells per well) were seeded and grown to 90-95% confluency in 24 well plates before treatment with the proteinoid particles. Cell cultures that were not exposed to the particles were included in all assays as negative controls. Cell cultures that were treated with 1% Triton-x-100 were used as positive controls. To test if the particles can interact with LDH kit compounds, cell cultures were exposed to a mixture containing maximal nano/micro-particles concentration dispersed in PBS and 1% Triton-x-100.

The proteinoid particles were freshly dispersed in PBS (1.25 and 2.5 mg/mL) and then added to the 95% confluent cell culture in culture medium. The cell cultures were further incubated at 37° C. in a humidified 5% $CO_2$ incubator and then checked for cellular cytotoxicity at intervals of 24 h.

The percentage of cell cytotoxicity was calculated using the formula shown in the manufacturer's protocol. All samples were tested in tetraplicates.

XTT assay was performed to determine the viability of the LS174t and SW480 cell lines after nanoparticle treatment. The assay is based on the ability of the mitochondrial succinate-terazolium reductase system to convert yellow tetrazolium salt XTT (sodium 3'-[1-(phenylaminocarbonyl)-3,4-tetrazolium]-bis (4 methoxy-6-nitro) benzene sulfonic acid hydrate) to orange formazan dye. The test denotes the percentage of the cells that survive after toxic exposure.

Cells were seeded in a 96-well plate at a density of $1\times10^4$ cells/well in 100 µL culture medium and grown in a humidified 5% $CO_2$ atmosphere at 37° C. After 24 h at 37° C., different volumes of the nanoparticles dispersed in PBS were added to the cells, giving final concentrations of 2.5, 1.25 and 0.625 mg/mL per well. After incubation for 24 h or 48 h at 37° C., 50 µL XTT solution was added to each well according to the kit manufacturer's instructions. Absorbance was read at 480 nm. Cell viability was determined using the formula shown in the manufacturer's protocol. The reference wavelength used was 650 nm.

Particle Stability:

Proteinoid particles aqueous dispersions (1 mg/mL) were put in a refrigerator at 4° C. for 6 months. Samples were taken at different time periods, filtered through a centrifugation tube (Vivaspin 3000 Da MWCO) and the filtrate was checked by UV at 200-210 nm, to find aqueous soluble proteinoid and at 630-900 nm to find free ICG. Also, the particle aqueous dispersions were checked by Nanophox for their size and size distribution. In order to check the particle stability after drying, the particles were lyophilized to dryness and then dispersed in an aqueous phase to their original concentration. The samples size and size distribution were then rechecked by Nanophox.

Encapsulation of Different Materials within the Particles:

Prot8 was used to encapsulate several materials. To the heated proteinoid mixture (10 mg in 9.8 mL NaCl $10^{-5}$N, at 80° C.), 1% w/w of the wanted material (dissolved in 200 µL NaCl solution) was added. The heating was stopped, the mixture was mechanically stirred at 250 rpm and left to cool to room temperature in order to form the proteinoid particles containing the encapsulated material. The encapsulated materials were toluene, perfluorohexane (PFH), fluorescein, solvent blue 59 dissolved in toluene and indocyanine green (ICG). The particles were washed and characterized as mentioned before for their size and size distribution. Also, the fluorescein and ICG-containing proteinoid particles were characterized by UV and fluorescence. Absorbance spectra were obtained using a Cary 100 UV—Visible spectrophotometer (Agilent Technologies Inc.). Excitation and emission spectra were measured by a Cary eclipse spectrofluorometer (Agilent Technologies, Inc.).

Determination of the Encapsulated ICG Content:

A calibration curve of free ICG was obtained by measuring the integrals of the absorbance peaks of standard solutions (0.5-10 µg/mL) in PBS, at wavelengths 630-900 nm. The concentration of the encapsulated ICG was determined by measuring the integral of the absorbance spectrum at 630-900 nm of a 1 mg/mL dispersion of the NIR fluorescent nanoparticles in PBS. An estimation of encapsulated ICG per mg of nanoparticles was determined according to the calibration curve.

Optimization of the Encapsulated ICG Content:

The fluorescence intensity of the P(EF-PLLA) (P: poly; E: L-glutamic acid; F: L-phenylalanine) nanoparticles was varied by changing the ICG concentration within the nanoparticles (0.5%, 1%, 2% and 5% w/w).

Different samples of the NIR fluorescent P(EF-PLLA) nanoparticles were prepared as described in the experimental section. The nanoparticle aqueous dispersions were diluted to 1 mg/mL in PBS, illuminated at 750 nm, and their relative fluorescence intensities at 809 nm were measured and compared.

Leakage Extent of the Encapsulated ICG from the Nanoparticles into the PBS Continuous Phase:

An NIR fluorescent P(EF-PLLA) nanoparticle dispersion (10 mg/mL in PBS containing 4% HAS) was shaken at room temperature for 1 h and then filtered via a 300-kDa filtration tube (VS0241 VIVA SPIN) at 4000 rpm (Centrifuge CN-2200 MRC). The fluorescence and absorbance intensities of the filtrate were measured as mentioned in the experimental section, to account for ICG leaks from the nanoparticles to their surroundings.

Photostability of the NIR fluorescent P(EF-PLLA) Nanoparticles:

An aqueous solution of ICG (0.05 M) in PBS was prepared, and the fluorescence intensity with $\lambda_{ex}$ set at 780 nm and $\lambda_{em}$ set at 800 nm was measured. A dispersion of NIR fluorescent P(EF-PLLA) nanoparticles in PBS was prepared, and diluted to give a similar fluorescence intensity to the dye at the same wavelengths. The excitation and emission slits were opened to 20 nm and 5 nm, respectively. Each of the samples was illuminated continuously with a xenon lamp, and the fluorescence intensity was measured over a period of 20 min by a Cary Eclipse fluorescence spectrophotometer (Agilent Technologies Inc.). Intensity values were normalized for comparison.

Biodistribution in a Mouse Model:

Male BALB/C mice (Harlan Laboratories, Israel) were utilized in this study under a protocol approved by the Institutional Animal Care and Use Committee at Bar-Ilan University. The biodistribution of the NIR fluorescent Prot8 nanoparticles was studied in normal 8-weeks-old mice, weighing 20-25 g at the time of experiment. Prior to the experiment, mice were anesthetized by intraperitoneal injection of Ketamine (40-80 mg/kg body weight) and Xylazine (5-10 mg/kg body weight), and the mice's skin was shaved with an electric animal clipper.

100 µL of either nanoparticle dispersion or free ICG solution (0.01 mg/kg body weight, dissolved in PBS) were administered to the mice through tail vein injection at a concentration of 2 mg/mL. During image acquisition, mice remained anesthetized by the intraperitoneal injection of Ketamine/Xylazine. Image cubes were obtained from the mice at several time points up to 24 h after injection. Each treatment group includes 3 mice for each time point (5 min, 20 min, 1 h and 24 h); 2 uninjected mice served as negative control. The experiment was repeated twice, testing a total of 52 mice. At the end of the experiment, the mice were euthanized by cervical dislocation, and organs were taken for imaging (liver, spleen, kidney, duodenum, colon, brain, heart, tibia bone and blood).

Fluorescence images were acquired using a Maestro II in vivo fluorescence imaging system (Cambridge Research &Instrumentation, Inc., Woburn, Mass.). The system is equipped with a fiber-delivered 300W xenon excitation lamp, and images can be acquired from $\lambda$=500-950 nm by a 1.3 megapixel CCD camera (Sony ICX285 CCD chip). Each pixel within the image cube therefore has an associated fluorescence spectrum. The software for the Maestro system (Maestro 2.10.0) contains several algorithms to process the spectral data cubes to remove undesired auto-fluorescence signal and generate overlaid images for multiple fluorophores. A deep red excitation/emission filter set was used for our experiments (λex: 700-770 nm, λem>780 nm). The liquid crystal tunable filter (LCTF) was programmed to acquire image cubes from λ=780 nm-860 nm with an increment of 10 nm per image. The camera was set to 150 ms (whole body image), 15 ms (liver), 500 ms (spleen), 7000 ms (kidney), 10 ms (duodenum), 500 ms (colon), 1000 ms (brain), 1000 ms (tibia bones), 200 ms (heart) and 1000 ms (blood) exposure times. Fluorescence intensity measurements were performed using ImageJ NIH (National Institutes of Health) software.

Conjugation of the Tumor-Targeting Ligands to the Nanoparticles:

PNA was covalently conjugated to the NIR fluorescent P(EF-PLLA) nanoparticles by the cabodiimide activation method. Briefly, EDC (1 mg) and sulfo-NHS (1 mg) were each dissolved in 0.1 M MES (pH 6.0, 1 mL) containing 0.5 M NaCl. The EDC solution (1 mg/mL, 10 μL) was added to an aqueous solution of PNA (0.25 mg, 62.5 μL), followed by the addition of the sulfo-NHS solution (1 mg/mL, 25 μL). The mixture was then shaken for 15 min, followed by the addition of the NIR fluorescent P(EF-PLLA) nanoparticles (2.5 mg in 1 mL PBS). The mixture was then shaken for 90 min. The obtained PNA-conjugated fluorescent nanoparticles were then washed from excess reagents by dilution and filtration through a 30-kDa filtration tube (VS2021 VIVA SPIN) at 1000 rpm (Centrifuge CN-2200 MRC) for 2 min, and this was repeated three times. FITC-PNA and anti-CEA were conjugated to the NIR fluorescent nanoparticles through a similar procedure. In additional experiments, anti-rabbit IgG was conjugated to nanoparticles as a non-specific binding agent, with the intention of inactivating the conjugated particles in terms of tumor detection.

The concentration of bound PNA was determined with FITC-PNA by a calibration curve of FITC-PNA fluorescence using a multiplate reader (TECAN SpectraFluor Plus, Neotec Scientific Instruments). The concentration of bound anti-CEA was determined using a mouse IgG ELISA kit (Biotest, Israel).

Chicken Chorioallantoic Membrane (CAM) Grafting Procedure:

Human colorectal adenocarcinoma cell lines were used for each of the experiments. The LS174t cell line was maintained in Minimum Essential Medium (MEM) eagle supplemented with heat-inactivated FBS (10%), penicillin (100 IU/mL), streptomycin (100 μg/mL) and L-glutamine (2 mM). SW480 cell line was maintained in Dulbecco's MEM supplemented with FBS (10%), penicillin (100 IU/mL), streptomycin (100 μg/mL) and L-glutamine (2 mM).

Tumor cells were grafted on CAM according to the literature. Briefly, fertile chicken eggs obtained from a commercial supplier were incubated at 37° C. at 60-70% humidity in a forced-draft incubator. On day 3 of incubation, an artificial air sac was formed, allowing the CAM to drop. After 8 days of incubation, a window was opened in the shell and the CAM was exposed. Tumor cells were collected by trypsinization, washed with culture medium and pelleted by gentle centrifugation. Following removal of the medium, $5 \times 10^6$ cells were resuspended in 30 μL ice-cold Matrigel and inoculated on the CAM at the site of the blood vessels. Eggs were then sealed and returned to incubation. On day 6 post-grafting, day 14 of incubation, the tumor diameter ranged from 3 to 5 mm with visible neoangiogenesis.

Optical Detection of Human Colon Tumor with the Non-Conjugated and Bio-Conjugated NIR Fluorescent P(EF-PLLA) in a Mouse Model:

Experiments were performed according to the protocols of the Israeli National Council for Animal Experiments by Harlan Biotech, Israel. Cancerous cells (30 μL containing $2 \times 10^6$ LS174t cells) were injected into the mouse intestinal wall. 2 weeks later the nude mice were anaesthetized and treated with the bio-conjugated NIR fluorescent P(EF-PLLA) nanoparticles (0.1%, 200 μL), through the anus, using the guidance of a mini-colonoscope. 20 min later each colon was washed with PBS (5×1 mL) and mice were allowed to recover for 4 h. The mice were sacrificed and the colons were removed. Each colon was spread on a solid surface and imaging was performed using the Odyssey Infrared Imaging System (Li-Cor Biosciences, Lincoln, Nebr., USA) with excitation wavelength of 780 nm and emission wavelength of 800 nm.

Results

Synthesis and Characterization of the Proteinoids:

As described above, different proteinoids were prepared by thermal condensation of different monomer contents. Table 2 exhibits the different synthesized proteinoids and their characteristic molecular weights, polydispersity and optical activity.

TABLE 2

| Proteinoid[a] | Mw (Da)[b] | Mn (Da)[b] | Mp (Da)[b] | PDI[c] | Optical Activity $[α]_D^{25°\,C.}$ (°)[d] |
|---|---|---|---|---|---|
| Prot1 | 26250 | 11300 | 11320 | 2.32 | +6.5 |
| Prot2 | 181540 | 144940 | 195300 | 1.25 | −4.4 |
| Prot2[e] | 500240 | 497280 | 503070 | 1.01 | +8.1 |
| Prot3 | 164930 | 138250 | 158740 | 1.19 | −9.0 |
| Prot4 | 87660 | 84410 | 85250 | 1.04 | −3.3 |
| Prot5 | 195080 | 165870 | 191440 | 1.17 | −7.4 |
| Prot6 | 190390 | 163290 | 204050 | 1.16 | −15.1 |
| Prot7 | 72260 | 56880 | 42870 | 1.27 | +2.8 |
| Prot8 | 168300 | 156600 | 136800 | 1.07 | −4.6 |

[a]The proteinoids were prepared at 180° C. according to the experimental section;
[b]molecular masses were measured by GPC, Mp is the molecular mass at the peak;
[c]PDI is the polydispersity index, given by Mw/Mn;
[d]specific optical rotation (c = 1, in $H_2O$, at 25° C.);
[e]made by microwave-assisted polymerization.
Each experiment was performed 3 times, with an error of 0.5-1.7%.

Table 2 indicates a relatively low PDI values for the obtained proteinoids. This is quite unexpected since the polycondensation of the various amino acids is random. The highest PDI (2.32) was observed for Prot1, composed of the single amino acid (L)glutamic acid, while the PDIs of the other proteinoids composed of at least 2 amino acids range between 1.01 and 1.27.

All of the thermally-made proteinoids have relatively high molecular masses of 26-195 kDa. This indicates that the polymerization procedure by thermal heating used here provides relatively long polymer chains. This fact can be an advantage for different uses later, since polymers with such high molecular weights are usually mechanically stronger and resemble natural proteins. Table 2 indicates that the lowest molecular weight was observed for the proteinoid composed of the single amino acid (L)glutamic acid (Prot1) and the highest one for the proteinoid composed of (L)glutamic acid, (L)aspartic acid and (L)lysine (Prot 5). Prot2, which was synthesized by microwave-assisted polymerization, reached an abundantly higher molecular weight. In this procedure, a 500 kDa proteinoid chain was made, about twice the size of the thermal proteinoid. This kind of procedure gives us better yield over 60 min, compared to the 3 h needed usually. It can be used further for higher molecular weights and more rigid proteinoids. However, unfortunately, this kind of proteinoid does not self-assemble into spherical-shaped particles.

All of the proteinoids exhibit optical activity, although the monomers are known to racemize during the thermal process. This fact can become a benefit later in the design of a stereospecific drug carrier, for example.

Figure 1:
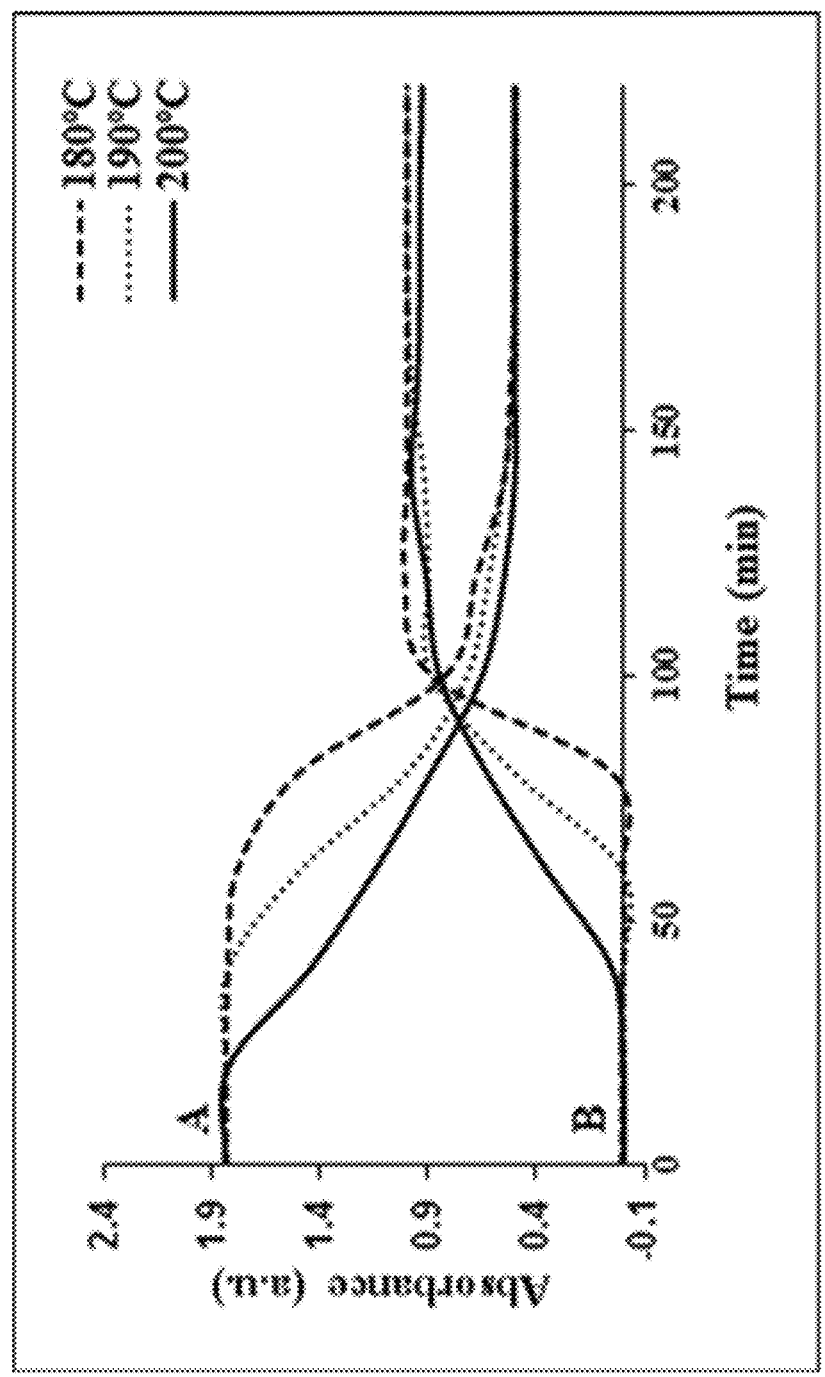

The polymerization kinetics was examined over 220 min at three different temperatures (180, 190 and 200° C.) as illustrated in FIG. 1. The results shown refer to the synthesis of Prot3, consisting of (L)glutamic acid and (L)phenylalanine. Similar results were observed for the other systems, Prot1-8, as well. It can be seen that at all temperatures, the polymerization takes place mainly over the first 100 min. After that, both ninhydrin (A) and Biuret (B) tests show no significant drop of the free amines (ninhydrin signal) or rise of the peptide bonds (Biuret signal). This figure also shows that as the temperature of the reaction was raised, the rate of the reaction increased. However, the preferred reaction temperature is 180° C., as the yield of the reaction is higher since the amino acids decompose faster at the higher temperatures.

The proteinoids were also characterized by infrared spectroscopy. All proteinoids showed characteristic peaks of NH stretching at 3360 and 2990 $cm^{-1}$, amide CO stretching at 1565 $cm^{-1}$, an amide NH bending band at 1450 $cm^{-1}$ and CO bending at 500-700 $cm^{-1}$. A representative spectrum of Prot3 is shown in FIG. 2.

Carboxyl Group Analysis:

The presence of excess dicarboxylic amino acids in the synthesized proteinoids, aspartic acid and glutamic acid, provides acidic nature to the resulted polymers. This is also evident from carboxyl group content of the synthesized proteinoids where it shows higher values of 80-155 mmol/g compared with albumin (see Table 3 showing carboxyl group content in the proteinoids and albumin). This is true also in Prot5-7, where lysine is also a part of the polymer. Moreover, aspartic and glutamic acid moieties in the proteinoids, along with lysine, impart the hydrophilic nature of the whole proteinoid. The biodegradability rate of various amino acid polymers increases with their hydrophilicity. Therefore, it is more appropriate to choose these proteinoids as ideal biomaterials for drug delivery applications.

TABLE 3

| Polypeptide | [Carboxyl groups] (mmol/g)* |
|---|---|
| Albumin | 56 |
| Prot1 | 150 |
| Prot2 | 155 |
| Prot3 | 90 |
| Prot4 | 122 |
| Prot5 | 88 |
| Prot6 | 87 |
| Prot7 | 80 |
| Prot8 | 102 |

*Each experiment was performed 4 times, with an error of 0.5-2%

Thermal properties of the proteinoids: The thermal properties of the proteinoids were investigated by DSC and TGA, as presented in Table 4.

TABLE 4

| Proteinoid | Tm (° C.)[a] | ΔHm (J/g)[a] | Tdec (° C.)[b] | Weight loss (%) |
|---|---|---|---|---|
| Prot1 | 102 | −300.7 | 300 | 55 |
| Prot2 | 89 | −428.7 | 297 | 57 |
| Prot3 | 103 | −174.9 | 341 | 54 |
| Prot4 | 217 | −183.4 | 330 | 25 |
| Prot5 | 78 | −251.5 | 339 | 57 |
| Prot6 | 241 | −90.1 | 373 | 47 |
| Prot7 | 246 | −139.4 | 385 | 64 |
| Prot8 | 117 | −420.5 | 268 | 47 |
| PLLA[c] | 150 | −57.2 | 349 | 90 |

[a]Tm and ΔHm were measured by DSC;
[b]Tdec (temperature of decomposition) was measured by TGA/DSC and refer to the exothermal peak in DSC;
[c]commercial PLLA 2000 Da parameters were measured similar to the made proteinoids. Each experiment was performed 3 times, with an error of 1-1.5%.

The melting temperatures of the different proteinoids range between 78-246° C. The wide range of temperatures derives from the difference in the monomeric units used in each proteinoid. When using phenylalanine, as in Prot3, 4, 6 and 7, the resulted proteinoid gains significant rigidity in the overall structure, due to the aromatic rings which allow pi-stacking. Hence, these proteinoids melt at higher temperatures. When PLLA is incorporated into the proteinoid, as in Prot8 compared to Prot3, the Tm rises mildly (103° C. and 117° C., respectively), due to the presence of 2000 Da rigid polymer chains in the overall proteinoid structure.

The TGA/DSC measurements of the proteinoids show decomposition temperatures of 268-385° C. Most proteinoids lose at this temperature range around 50% of their weight. The decomposition measured at 400° C. of most proteinoids is between 47-64%, except Prot4 (25%). Pure PLLA decomposes at 349° C. almost completely (90% weight loss). Prot8, composed of PLLA segments (10%), has the lowest decomposition temperature of all proteinoids (268° C.). This can be explained by the non-uniformity of the structure of the whole proteinoid due to the inserted segments of 2000 Da PLLA within the random segments of polymerized amino acids.

Preparation and Characterization of the Proteinoid Particles:

The crude proteinoids were self-assembled in a variety of environments, in order to find the best conditions for forming the nano/micro particles. The desired particles, spherically-shaped, have to be small and uniform in size through the whole sample. Each self-assembly method gave particles of different properties, e.g., different size and size distribution.

In order to compare between the different conditions, Prot3 was examined. First, different salt solutions were investigated: double-distilled water, $10^{-5}$-1N NaCl solutions and PBS at the same proteinoid concentration (10 mg/mL), heating for 30 min at 80° C. and cooling slowly to room temperature, simply by removing the heat source and leaving the mixture to cool. As seen in Table 5, (showing the effect of self-assembly conditions on proteinoid particle size and size distribution) the smallest particle size was achieved using $10^{-5}$N NaCl solution, with a relatively good standard deviation of 12%. In general, as the ionic strength of the salt solution decreases, the particle size and size distribution decreases. When the self-assembly process takes place in water, in the absence of the salt, the particles formed are large, over 3 μm, and have a very wide size distribution. In PBS, the particles formed are around 2 μm with a relatively narrow size distribution. This way, a large variety of proteinoid particles of different size and size distribution can be made, by changing their outside environment only.

TABLE 5

| Solution | Particle size (nm)$^{a-c}$ | Standard deviation (%) |
|---|---|---|
| Water | Over 3000 | 200 |
| NaCl $10^{-5}$N | 196.2 ± 23.9 | 12.2 |
| NaCl $10^{-3}$N | 486.2 ± 54.3 | 11.2 |
| NaCl 0.1N | 573.4 ± 47.9 | 17.5 |
| NaCl 1N | 1035.5 ± 325.1 | 31.4 |
| PBS | 2151.0 ± 204.3 | 9.5 |

$^a$Particles were made of Prot3;
$^b$particles made by heating to 80° C. with mechanical stirring and then slow cooling to room temperature;
$^c$the particle size and size distribution were measured by DLS.

In addition to the outside environment control, the effect of the reaction conditions on the size was examined by changing the heating, stirring and cooling parameters. Four proteinoid samples in water (10 mg/mL) were introduced to different conditions in terms of heating time after dissolving the proteinoid polymer, stirring and cooling method.

The results are shown in Table 6 presenting the effect of self-assembly reaction conditions on proteinoid particle size and size distribution.

TABLE 6

| Heating time (min) | Stirring$^a$ | Cooling method$^b$ | Particle size (nm)$^c$ | Standard deviation (%) |
|---|---|---|---|---|
| 30 | – | slow | 722.5 ± 84.8 | 11.7 |
| 60 | – | slow | 2293.7 ± 277.8 | 12.1 |
| 30 | + | slow | 811.4 ± 118.5 | 14.6 |
| 30 | – | fast | 1898.1 ± 213.2 | 11.2 |

$^a$Stirring by a magnetic stirrer;
$^b$slow cooling by removal of the heating and leaving the sample to cool to room temperature, fast cooling by refrigerating the sample;
$^c$the particle size was measured by DLS.

As seen, the smallest particles were produced by the first procedure: heating for 30 min and cooling slowly to room temperature. Overall, the different procedures gave particles of narrow size distributions.

Self-assembly of Prot8 was carried out in the best conditions found until now: $10^{-5}$N NaCl solution, heating at 80° C. for 30 min, followed by slow cooling to room temperature. The procedure produced spherical proteinoid particles of 103±11 nm hydrodynamic diameter and 70±15 nm dry diameter, as shown in FIGS. 3A-B. The hydrodynamic diameter of these particles dispersed in water is illustrated by the typical light scattering measurement shown in FIG. 3A. The dry diameter of the proteinoid particles is illustrated by the typical SEM photomicrograph shown in FIG. 3B.

Several P(EF-PLLA) copolymers were synthesized, changing the PLLA percentage in the total monomer weight, as specified in the methods section. FIG. 4 exhibits the effect of changing the PLLA content on the different P(EF-PLLA) particle sizes.

As shown, the optimal particles, judging by their size and size distribution, are the particles made of P(EF-PLLA) where PLLA is 10% of the total monomer. In this case, the particles formed are nanoparticles of the smallest nanometric size with a narrow size distribution, 103±11 nm. When PLLA is of lower percentage in the total monomer weight, the copolymers self-assemble into larger particles in size, 232-502 nm. Overall, as the PLLA fraction in the copolymer rises, the particles formed are smaller in size, indicating the importance of incorporating PLLA into the proteinoid particles, where these hydrophobic moieties are well-packed to form the interior of the nanoparticle. However, P(EF-PLLA) with 20% PLLA does not self-assemble into particles at the specified conditions in the methods section.

The difference in the particle size between the SEM and the light scattering measurements is due to the fact that SEM measurements determine the dry diameter, whereas light scattering measurements takes into account the hydrated water layers adsorbed onto the particle's surface. As mentioned above, Prot8 has small PLLA segments incorporated within the random polymerized amino acid segments. This fact grants the proteinoid a more hydrophobic backbone. These hydrophobic segments are packed better in the interior part of the spherical particles during the self-assembly precipitation process. The addition of the PLLA segments also leads to the formation of smaller size particles. For example, under similar preparation conditions Prot3, composed of (L)glutamic acid and (L)phenylalanine, provided particles of 196.2±23.9 nm while Prot8 composed of (L)glutamic acid, (L)phenylalanine and PLLA provided particles of 103±11 nm diameter.

It should also be noted that overall, the proteinoid particles maintain their size and size distribution upon change of the outside environment, given that the change is not by drastic pH values. This way, for instance, Prot8 particles preserve their size when transferred from water to PBS.

Density measurements indicated that all proteinoid particles possess a very low density, ranging from 0.001 to 0.014 g/mL indicating that the particles formed are hollow. The hollow nature of the particles is significantly important for applications such as ultrasound imaging agents, drugs and dyes encapsulation, controlled released, etc.

Without being bound by any particular theory, it is suggested that the proteinoid forms particles of different sizes according to the nature of its surrounding. The hydrophobic portions of the crude proteinoid are assembled within the particle matrix, while the polar hydrophilic groups (carboxylic acids and amines) are exposed to the aqueous environment, as illustrated in FIG. 5.

Cellular Cytotoxicity of the Proteinoid Particles by LDH Assay:

In order to revoke cell toxicity of the new proteinoid particles, in vitro cytotoxicity of the particles was assessed by measuring the release of cytoplasmic lactate dehydrogenase (LDH) into the cell culture supernatants. LDH is an intracellular enzyme that catalyzes the reversible oxidation of lactate to pyruvate. Since LDH is mainly present in the cytosol, it is released into the supernatant only upon cell damage or lysis. When tested by the LDH quantitative assay, Prot2, 4, 5, 7 and 8 particles dispersed in PBS at concentrations of 1.25 and 2.5 mg/mL had none, or minor cytotoxic effect on the human colon adenocarcinoma cell line LS174T (FIG. 6). Treatment of the cells with Prot2 and Prot5 particles at both concentrations produced the highest LDH levels (up to 13% toxicity), when compared to untreated (blank) cells, indicating minor toxicity of these proteinoids to this cell line. Prot8 had the lowest, or no cytotoxic effect on the cells treated with both concentrations. This proteinoid is therefore the most suitable for treating cells, considering its low toxicity.

Cytotoxicity of the P(EF-PLLA) Nanoparticles:

In order to revoke cell toxicity of the NIR P(EF-PLLA) nanoparticles, in vitro cytotoxicity of the particles was tested by using human colorectal adenocarcinoma LS174t and SW480 cell lines. The NIR fluorescent nanoparticles were tested by the XTT assay for in vitro cell viability following exposure to the nanoparticles. In order to determine the number of viable cells the XTT assay uses 2,3-Bis-(2-methoxy-4-nitro-5-sulfophenyl)-2H-tetrazolium-5 carboxanilide salt (XTT). Only in living cells mitochondria are capable to reduce XTT to form orange colored water soluble dye, which its concentration is proportional to the number of living cells and can be calculated as mentioned in the experimental section. LS174t and SW480 were exposed to different concentrations of the P(EF-PLLA) nanoparticles. FIG. 7 exhibits the cell viability levels of the cells post nanoparticle treatment. Treatment of LS174t cells with 1.25 and 2.5 mg/mL nanoparticles in PBS produced a minor decrease in viability level (10%) after 24 h when compared to untreated (blank) cells. On the other hand, the nanoparticles (1.25 and 0.625 mg/mL) increase the viability levels of SW480 cells (177% and 134%) 24 h after treatment, probably due to cell exploitation of the nanoparticles as nutrients. Overall, the nanoparticles can be considered as non-toxic and can be further used with human cells.

Particle Stability:

The stability against agglomeration of the proteinoid particles dispersed in an aqueous phase (1 mg/mL) and kept in the refrigerator was examined at different time periods over 6 months as described in the experimental section. Overall, the proteinoid particles as well as the NIR fluorescent P(EF-PLLA) nanoparticles remain in the same size after 6 months in storage at 4° C. Also, the degradation and/or dissolution of the proteinoid particles in the aqueous continuous phase was tested by the filtration centrifugation method and resulted in negative results in the filtrate, meaning no degradation or dissolution occurs at this temperature over 6 months. When lyophilized to dryness, the proteinoid particles can be redispersed in water completely while the particle size and size distribution remains the same. This means that the particles can be stored as a freeze-dried powder as well, and redispersed when needed, without the need to add cryoprotectants.

Photostability:

In order to examine the photostability of the encapsulated ICG as opposed to free ICG, photobleaching experiments were performed for both the encapsulated and the free dye. Samples of free ICG and the ICG-containing P(EF-PLLA) particles were illuminated at 800 nm and their fluorescence intensities were measured over a period of 20 min. During illumination, the fluorescence intensity of the ICG-containing P(EF-PLLA) particles remains intact while that of the free ICG decreased significantly, as shown in FIG. 8. As illustrated in FIG. 8, the photobleaching of ICG is significantly reduced by the encapsulation within the proteinoid-PLLA particles. The encapsulation probably protects the free dye from light-inducing factors such as oxygen, oxidizing or reducing agents, temperature, exposure time and illumination levels, which may reduce the fluorescence intensity irreversibly.

Encapsulation of Different Materials within the Proteinoid Particles:

Different materials were encapsulated within Prot8 according to the description above. Fluorescein encapsulation was successful, as no fluorescein was detected in the aqueous filtrate. The fluorescein encapsulation process yields 425.2±21 nm particles, which were found stable for at least 6 months. FIG. 9 exhibits the absorbance and emission spectra of free fluorescein compared to encapsulated fluorescein particles. A 14 nm red-shift of the absorbance spectrum of the fluorescent proteinoid particles, compared to free fluorescein in solution, was observed. This indicates that the physical binding to the proteinoid, which places the dye in a more hydrophobic environment, affects the dipole moment of the dye. The fluorescence and absorbance of the fluorescent proteinoid particles dispersed in PBS and stored at 4° C. remain the same after 6 months.

Similarly, the encapsulation of toluene was successful, as no organic separate phase was present at the end of the process. In this case, the proteinoid serves as a surfactant for dispersing the organic toluene droplets in water. No phase separation was observed within 6 months following the encapsulation. Particles containing toluene reached a size of 411.9±59.1 nm. The encapsulation of solvent blue 59 dissolved in toluene resulted in slightly larger particles, 442.5±66.6 nm. In this case, as in the encapsulation of toluene, no phase separation is observed over 6 months. When PFH is present during the particle formation, encapsulation yields 546.9±52.4 nm particles. Examination the PFH particles over 24 h, shows a clear phase separation. Hence, the PFH particles can only serve immediate needs, such as ultrasound contrast agent.

Likewise, the NIR FDA-approved ICG was encapsulated successfully in the Prot8 nanoparticles. FIGS. 10A and 10B show that the dry (FIG. 10A) and hydrodynamic (FIG. 10B) diameters of the NIR fluorescent Prot8 nanoparticles are 70±15 nm and 145±20 nm, respectively. FIGS. 10C and 10D exhibit the fluorescence and absorbance spectra of the NIR fluorescent Prot8 nanoparticles compared to those of the free dye in solution. The absorbance spectra show no shift in the absorbance. However, due to the dye encapsulation process the maximal absorbance peak of the free ICG became minimal and the minimal peak of the free dye became maximal after encapsulation, since the ICG molecules get close to each other inside the nanoparticle interior and aggregation may occur and cause this change in absorbance. Moreover, a blue-shift of 12 nm in the emission spectrum of the NIR fluorescent nanoparticles compared to the free ICG in solution was also observed, due to the dye molecule aggregation inside the particle.

Biodistribution in a Mouse Model:

NIR fluorescent Prot8 nanoparticles (2 mg/mL, 0.01 mg/kg body weight per mouse) were injected into mice through the tail vein. Organs from mice were harvested and blood was drawn 5 min, 20 min, 1 h and 24 h post injection of the nanoparticles into the tail vein. The calculated fluorescence intensities of the lungs, bones, brain, colon, duodenum, heart, liver, kidney, spleen and blood screening are shown in FIG. 11. Evidently, the results show that the nanoparticles penetrated and were found in all organs. It is shown that by 20 min the majority of the inserted quantity of the fluorescent nanoparticles is cleared from the blood. The nanoparticles concentrate mostly at the liver and are possibly evacuated from the body. It is also apparent that the nanoparticles pass the blood-brain barrier (BBB), since they are found in the brain at 20 min post injection. This may open up a scope of drug targeting to the brain for drug molecules which are usually blocked. Overall, it was demonstrated that following a single in vivo injection of the nanoparticles, fluorescence intensity at all organs decreased over time, and only traces of fluorescence could be seen after 24 h.

Conjugation of the Bioactive Reagents:

To demonstrate the feasibility of using the NIR fluorescent P(EF-PLLA) nanoparticles for tumor detection, PNA and anti-CEA were covalently conjugated to these fluorescent nanoparticles. PNA binds to the terminal sugar β-D-galactosyl-(1-3)-N-acetyl-D-galactosamine of the Thomsen-Friedenreich antigen. According to the literature, this antigen is upregulated on the mucosal side of various colorectal cancer cell lines such as LS174t, compared to the SW480 cell line in which this antigen is expressed at much lower extent. Anti-CEA antibody is an antibody against carcinoembryonic antigen (CEA), a highly glycosylated glycoprotein expressed on most types of human carcinomas. As stated in the literature, CEA is upregulated on the mucosal side of LS174t colorectal cancer cell line, as opposed to SW480 (at least ×10³ less).

Anti-rabbit IgG was also conjugated to nanoparticles as a non-specific binding agent, with the intention of inactivating the conjugated particles in terms of tumor detection.

The concentration of biological ligand conjugated to the nanoparticles should be monitored carefully. The ligand content on the surface should be both sufficient for recognition by the cell from any angle of approach, and limited to revoke steric interference of the interaction with the cell receptors.

The concentration of bioactive ligand bound to the nanoparticles was determined using FITC-PNA for PNA and mouse IgG ELISA for anti-CEA, as described above. The calculated quantities of bound PNA and anti-CEA were 3.2 and 1.9 µg per mg nanoparticles, respectively. As will be demonstrated later, when using these concentrations of bound ligands in testing the ligand-receptor interaction, an increased signal of fluorescence was seen in cancer cells with upregulated corresponding receptors. Experiments with larger concentration of bound ligand showed a significant decrease in the fluorescence, possibly due to steric hindrance.

In additional experiments, the fluorescent signal of LS174t tumors labeled by anti-CEA-conjugated nanoparticles was 4 times higher than that of the tumors labeled by the anti-rabbit IgG-conjugated nanoparticles. Anti-rabbit IgG "blocks" the particle from interacting with the tumor receptors by the conjugation to the surface active moieties, thus serving as a negative control in colon tumor labeling.

Tumor Growth on the Chicken Chorioallantoic Membrane (CAM) Model:

A chicken embryo CAM model was used to test the specific tumor detection by both the non-conjugated and the bioactive (PNA and anti-CEA) conjugated NIR fluorescent P(EF-PLLA) nanoparticles. Among most commonly used animal models, the chicken egg model allows the imaging of several tumors in a short time period and is less expensive than other models. All cancer cell lines evaluated in this study were able to form solid tumors, 3 to 5 mm in diameter depending on the cell line. FIG. 12 shows typical SW480 cell line derived tumors bordered by plastic rings on a chicken embryo CAM inside the egg.

Optical Detection of LS174t and SW480 Human Colorectal Tumor Cell Lines on CAM Model:

LS174t and SW480 colorectal cell lines were used to demonstrate the possible use of the NIR fluorescent P(EF-PLLA) nanoparticles in tumor detection. As mentioned in the experimental section, LS174t cells express certain receptors (β-D-galactosyl-(1-3)-N-acetyl-D-galactosamine and CEA) to a much higher extent than SW480 cells. This way, the chosen bioactive ligands PNA and anti-CEA, once conjugated to the P(EF-PLLA) nanoparticles, can lead the nanoparticles specifically to the LS174t cancer cells. As shown in FIG. 13, the LS174t tumors treated with bioactive-conjugated nanoparticles (B and C) gained higher fluorescence than SW480 tumors, compared to those treated with non-conjugated nanoparticles (A). This is accurate both for P(EF-PLLA) nanoparticles conjugated with PNA (B) and anti-CEA (C), probably as a result of effective ligand-receptor interactions.

In addition, the SW480 tumors treated with bioactive-conjugated P(EF-PLLA) nanoparticles gained less fluorescence compared to those treated with the non-conjugated nanoparticles. The relative fluorescence intensities of the tumors treated by conjugated and non-conjugated P(EF-PLLA) nanoparticles are summarized in FIG. 14. LS174t cells compared to SW480 cells gave fluorescence intensity ratios of 4:1 and 8:1 for PNA-conjugated nanoparticles and anti-CEA-conjugated nanoparticles, respectively. The non-conjugated P(EF-PLLA) nanoparticles also labelled the tumors. However, the difference in the intensities between the types of tumors were not statistically significant. In this case, the overall fluorescence in both types of cells was higher than when treated with PNA-conjugated nanoparticles. This fact shows that even the bare non-conjugated nanoparticles penetrate the human cancer cell lines to a good extent. The possible reason is that the P(EF-PLLA) nanoparticles can penetrate and label the cancerous cells specifically by either receptor-ligand interaction or utilization of these nanoparticles as nutrients for tumor growth, as they resemble biological proteins.

The fluorescence intensity ratios between the types of cells show the significance of the nanoparticle surface. As seen in FIG. 13(D), no autofluorescence was observed in untreated tumors, signifying that all fluorescent signals are related to the fluorescent P(EF-PLLA) nanoparticles labeling. FIG. 13€ shows that no non-specific labeling of non-pathological CAM tissue was observed, indicating the specificity of the P(EF-PLLA) nanoparticles towards the tumor tissue.

In Vivo Optical Detection of Human Colon Tumors in a Mouse Model:

Labeling of human colorectal tumors was performed using orthotopic mouse model (22 mice) with colonic tumors originated from LS174t cells injected to the colon wall 2 weeks before the experiment. Mice were anesthetized and treated with 0.1% bioconjugated NIR fluorescent P(EF-PLLA) nanoparticles dispersion in PBS through the anus. After 20 min, the colons were extensively washed with PBS and were left to recover for 4 h. The colons were then removed and prepared for the imaging as described in the methods section. FIGS. 15A-B show typical (8 out of 10 mice) fluorescent and grayscale images of the mice colons after treatment with anti-CEA (FIG. 15A) and anti-rabbit IgG (FIG. 15B) conjugated nanoparticles. As illustrated in FIG. 15A, the anti-CEA-conjugated nanoparticles detected the tumors specifically and selectively with good signal to background ratio (SBR), the background refers to the surrounding non-pathological tissue. Moreover, as illustrated in FIG. 15B, the "inactive" anti-rabbit IgG-conjugated nanoparticles did not produce a significant signal of the tumors.

Example 2

Proteinoid Polymers and Nano/Micro-Particles Containing Retinoic Acid for Biomedical and Cosmetic Applications Materials and Methods Synthesis:

The process as detailed hereinabove, was repeated with various mixtures of amino acids at different ratios (w/w), as described in Table 7 showing the amino acid content of the different proteinoids.

Characterization of the Proteinoids:

The molecular weights and polydispersity index of the dried crude proteinoids were determined using Gel Permeation Chromatography (GPC) as described hereinabove.

The optical activities of the proteinoids were determined using a PE 343 polarimeter as described hereinabove.

Preparation of the Proteinoid Nano/Micro-Particles by Self-Assembly Process:

Proteinoid particles were prepared by a self-assembly mechanism. Briefly, 10 mg of the dried proteinoid were added to 10 mL NaCl solution $10^{-5}$M. The mixture was then heated to 80° C. and stirred at 250 rpm, until the crude proteinoid dissolved completely. After 30 min of heating, 50 μl of DMSO were added and the proteinoid particles were formed by the removal of heating and slowly cooling to room temperature. After preparation, particles dispersion was then dialyzed through a cellulose membrane (1000 Da MWCO) against distilled water for 24 h in order to remove the DMSO.

Preparation of the Proteinoid Nano/Micro-Particles Containing RA:

Proteinoid particles containing retinoic acid (RA) were prepared in the same manner as the hallow particles, 10 mg of the dried proteinoid were added to 10 mL NaCl solution $10^{-5}$M. The mixture was heated to 80° C. and stirred at 250 rpm. Then, 0.5 mg of RA were dissolved in 50 μl of DMSO and heated to 80° C. After 30 min of heating, RA solution was added to the proteinoid mixture. The mixture was left to cool to room temperature, in order to form the proteinoid particles containing RA. After preparation, the particles dispersion was filtered through 3 μm glass microfiber membrane syringe filter (VWR EU, England) to remove excess RA crystals. In order to remove the DMSO, the particles dispersion was dialyzed through a cellulose membrane (1000 Da MWCO) against distilled water for 24 h.

Characterization of the Proteinoid Nano/Micro-Particles:

Hydrodynamic diameter and size distribution of the particles dispersion was measured at room temperature with a particle DLS analyzer as described hereinabove.

Surface potential of particles was measured by Zeta Potential Analyzer, Zetasizer 3000 HSa model, Malvern Instruments Company, England.

HPLC analysis carries out by Thermo SCIENTIFIC SpectraSYSTEM HPLC (USA) attached with a reverse phase C18 column (75 mm×4.6 mm, PHENOMENEX, USA). Mobile phase used was DDW and acetonitrile, both containing 0.1% aqueous solution of trifluoroacetic acid at 1 mL/min flow, wavelength were set at 350 nm. Samples were diluted by ethanol, sonicated in an ice-water bath for 10 min and injection volume was set at 50 μL for all standards samples.

The thermal behavior of the proteinoid particles was determined TGA with a TGA/DSC 1 STARe system as described above.

FTIR measurements of the proteinoid particles was performed as described above.

Cytotoxicity of the Proteinoid Nano/Micro-Particles:

Cell cytotoxicity was assessed by measuring the release of LDH into cell culture supernatants as described above.

Results

Synthesis of Proteinoid Polymers:

Without being bound by any particular theory, it is assumed that in order to obtain a proteinoid polymer with sufficient mechanical properties, a proteinoid should contain glutamic acids (or aspartic acid) to form an acid based polymer and incorporate phenylalanine that can provide physical stability. Phenylalanine has an aromatic ring, which is a rigid side chain and can form pi-stacking bonds that strengthens the particles. The proteinoid polymers synthesized here contain also tyrosine for its distinctive UV absorbance at 280 nm, and 4-Aminobenzoic acid (PABA) for its UV blocking ability between 290-320 nm. PABA consists of a benzene ring substituted with para-amino group and carboxyl group, and is incorporated in the proteinoid polymer as an unnatural amino acid A series of 5 proteinoids (AB1-5) were prepared using L-Glu, L-Phe and L-Tyr, with increasing PABA concentrations (0, 1, 5, 10, 20%, Table 7). The chosen amino acids that construct the proteinoid polymers were selected to provide the polymer with UV filtering features, for protection of RA from photo-dependent degradation. All trans-RA ("at-RA") is extremely sensitive to photo-degradation by bright artificial light or by sunlight. Light causes extensive conversion of at-RA to 13-cis-RA, which is much less potent than at-RA. Furthermore, proteinoids with different combinations of amino acids were also synthesized, to evaluate the influence of different amino acids on the proteinoid properties. A basic based proteinoid using L-Lys (instead of L-Glu) was synthesized (AB8), with the assumption that RA might be able to form electrostatic bonds between its carboxylic group and the lysine amino group. In addition, a proteinoid combining both L-Glu and L-Lys was prepared, to evaluate the ability to form particles of such proteinoid, with proximity to physical pH (AB9). A proteinoid containing L-Ile was synthesized (AB7), with the intent to form a particle core with similar structural residues to RA (Ile and RA have lipophilic side chains). Lastly, a proteinoid containing L-Glu, L-Phe and L-Trp was synthesized, to compare the particles formation between L-Tyr and L-Trp (both absorb at 280 nm; AB6). As described below, basic proteinoid is also being studied for its drug delivery properties (LPA). This to proteinoid showed the ability to encapsulate doxorubicin, and form nano-sized particles. Therefore, LPA is now being studied for its suitability to encapsulate RA.

TABLE 7

| Proteinoid | Amino Acids | Amino Acid Ratio (w/w) | PABA Percentage (%) |
|---|---|---|---|
| AB1 | Glu-(L), Phe (L), Tyr (L) | 1:1:1 | 0 |
| AB2 | Glu-(L), Phe (L), Tyr (L) | 1:1:1 | 1 |
| AB3 | Glu-(L), Phe (L), Tyr (L) | 1:1:1 | 5 |
| AB4 | Glu-(L), Phe (L), Tyr (L) | 1:1:1 | 10 |
| AB5 | Glu-(L), Phe (L), Tyr (L) | 1:1:1 | 20 |
| AB6 | Glu-(L), Phe (L), Trp (L) | 1:1:1 | 0 |
| AB7 | Glu-(L), Phe (L), Ile(L) | 1:1:1 | 20 |
| AB8 | Lys-(L), Phe (L), Tyr (L) | 1:1:1 | 20 |
| AB9 | Glu-(L), Lys-(L) Phe (L), Tyr (L) | 0.5:0.5:1:1 | 20 |
| LPA | Lys-(L), Phe (L), Arg (L), His (L) | 2:1:1:1 | 0 |

*In all proteinoids made by thermal condensation polymerization the total monomer content was 5 gr.

Characterization of the Proteinoid Polymers:

All polymers were characterized for their molecular weights and polydispersity index (PDI) by Gel Permeation Chromatography (GPC), and for their optical activity by a polarimeter. The molecular weights (Mw) of all the polymers made by thermal polymerization process were in range from 20 to100 kDa (see Table 8 showing Mw, Mn, Mp, PDI and optical activity of the various proteinoids), which is relatively high. The high Mw indicates that the polymerization procedure by thermal heating used here may provide relatively long polymer chains which resemble long proteins. Long polymers can be an advantage for different uses in later study. The proteinoid with the lowest molecular weight was AB6, possibly due to the bulky structure of L-Trp that can interfere with the polymerization presses. Yet, 20 kDA is still a molecular weight high enough to form proteinoid particles.

TABLE 8

| Proteinoid | Mw (Da) | Mn (Da) | Mp (Da) | PDI$^c$ | Optical Activity $[\alpha]_D^{25°\,C.}$ (°) |
|---|---|---|---|---|---|
| AB1 | 65084 | 61903 | 55350 | 1.02 | 2.4 |
| AB2 | 44263 | 39201 | 30394 | 1.12 | 4.2 |
| AB3 | 42199 | 39046 | 33136 | 1.08 | 4 |
| AB4 | 51684 | 47504 | 41611 | 1.08 | 12 |
| AB5 | 84201 | 80403 | 77179 | 1.04 | 6.4 |
| AB6 | 21294 | 20070 | 18484 | 1.06 | 3 |
| AB7 | 43401 | 40538 | 33926 | 1.07 | 10 |
| AB8 | 44766 | 39194 | 29300 | 1.14 | 18.8 |
| AB9 | 66766 | 61840 | 50214 | 1.07 | 11.2 |
| LPA | 96639 | 95601 | 91494 | 1.01 | 13.4 |

Molecular masses were measured by GPC,
Mp is the molecular mass at the peak;
PDI is the Poly Dispersity Index, given by Mw/Mn;
Specific optical rotation (c = 1, in H$_2$O, at 25° C.).

In general, the proteinoids did not lose their optical activity as a result of the polymerization process. This fact is notable, for example, when designing a stereospecific drug carrier.

Next, the proteinoids were scanned for their absorption spectra (FIGS. 16A-B), in order to study whether they can provide UV blocking for the RA, as discussed previously. All proteinoids displayed peaks between 240-320 nm (except LPA), FIG. 16A shows a series of proteinoids AB1-AB5, which contain the same amino acids (L-Glu, L-Phe and L-Tyr) and increasing PABA concentration (0, 1, 5, 10, 20%). Proteinoid AB1 (FIG. 16A,) displays a peak at 278 nm, derived from L-Tyr (absorbs at 280 nm). A proteinoid constructed of only L-Glu and L-Phe does not display peaks above 220 nm (peptide bond). Proteinoid AB2 (1% PABA) has a slightly larger absorption than AB1, and the peak shifted to 275 nm due to the incorporation of PABA in the proteinoid. As the concentration of PABA increases in the proteinoid, the intensity of the peak increases as well. The shifts in the proteinoids spectra can be caused by the different content of molecules, which causes a difference in the HOMO-LUMO interactions. Proteinoid AB5 (20% PABA; FIG. 16A) has the largest intensity peak at 265 nm, in comparison, proteinoid AB8 (FIG. 16B) that is L-Lys based (L-Lys, L-Phe, L-Tyr and 20% PABA) has a slightly lower peak at 272 nm. Proteinoid AB9 (FIG. 16B) has a very wide peak also at 272 nm, similar to AB8, although it contains both L-Lys and L-Glu (and also L-Phe, L-Tyr and 20% PABA). Furthermore, proteinoid AB7 (FIG. 16B) contains L-Ile instead of L-Tyr, and yet has a peak at 264 nm that stands from the PABA molecule that is a part of the proteinoid.

Proteinoid AB6 that contains L-Trp instead of L-Tyr (compared to AB1), and does not contain any PABA, has a peak at 280 nm that is derived from L-Trp absorbance at the same wavelength. Finally, LPA (L-Lys, L-Phe, L-Arg and L-His) is a proteinoid that is intendent for in-vivo use, and thus does not exhibit any unique absorbance.

Size, Size Distribution (SD) and Zeta Potential (ZP) Analysis of Hollow Nano/Micro-Particles:

Particles were prepared from each proteinoid in order to evaluate which proteinoid can produce particles with the best properties. As mentioned previously, proteinoid nano/micro-particles are formed by a self-assembly process. After preparation, the obtained particle were characterized for their size and size distribution, and for their physical stability by zeta potential (ZP), see Table 9 presenting size, SD and ZP of the different proteinoid particles. The hydrodynamic diameter of the particles was measured using dynamic light scattering (DLS). Most proteinoid particles were less than 180 nm, and have narrow SD of 10-12%. The first particles, AB1P, formed from proteinoid AB1, showed promising properties, such as, nanometric size particles, 118.2 nm, with SD of 12%. The next particles, AB2P, are made of proteinoid AB2 which contains 1% PABA, increased somewhat in size to 180.9 nm. As the PABA concentration increased in the proteinoid, the size of the particles decreased. Proteinoid particles AB5P are the smallest particles in this series, only 56.4 nm, and were made from proteinoid AB5 that contains the highest PABA concentration, 20%. The additional particles, AB6-9P, were also of nanometric size range 62.7-84.1 nm with narrow SD of maximum 12%. Particles made from proteinoid LPA, were larger, 550.5 nm, under these conditions. However, by altering the conditions of self-assembly process in the future, the particles size can be decreased.

The physical stability of the particles was measured using Zeta Potential (ZP) Analyzer. Generally, ZP value can predict physical stability of the nano\micro-dispersion. The ZP indicates the degree of repulsion between close and similarly charged particles in the dispersion (negative or positive) and the ability to prevent aggregation of the particles. ZP more than e.g., |30| mV indicates stable nano/micro-dispersion.

Proteinoid particles AB1P have ZP of −16.98. The negative charge is driver from the carboxylic groups of the L-Glu, which reside on the outside of the particle. AB2P have slightly lower ZP, −14.47 mV, could be from the addition of PABA to the proteinoid. Incorporation of PABA in the proteinoid might disrupt the particle stability (AB2-4P), if PABA is polymerized sequentially, and causes inflexibly in the proteinoid chain, the proteinoids will form less stable particles. Yet, addition of 20% PABA to the proteinoid, produces the most stable particles, AB5P, with ZP of −19.85 mV.

TABLE 9

| Particle* | Size (nm) | SD (%) | ZP (mV) |
|---|---|---|---|
| AB1P | 118.2 ± 14.2 | 12 | −16.98 |
| AB2P | 180.9 ± 19.8 | 11 | −14.47 |
| AB3P | 170.3 ± 13.6 | 8 | −5.37 |
| AB4P | 77.5 ± 8.5 | 11 | −12.95 |
| AB5P | 56.4 ± 5.8 | 10 | −19.85 |
| AB6P | 84.1 ± 10.1 | 12 | −3.9 |
| AB7P | 70.5 ± 8.5 | 12 | −6.4 |
| AB8P | 83.2 ± 9.2 | 11 | +1.6 |
| AB9P | 62.7 ± 7.1 | 11 | 0 |
| LPAP | 550.5 ± 50.6 | 10 | +13.2 |

*Proteinoid particles were made by self-assembly, 10 mg proteinoid dissolved in 10 mL of 10$^{-5}$ 1N NaCl solution, and then heated to 80° C., for 30 min Proteinoid particles were assembled by slowly cooling the dispersion to room temperature. After preparation, proteinoid particles were measured by DLS and by Zeta Potential Analyzer.

Although PABA donates rigidity to the proteinoid chain, PABA can stabilize the particles by forming pi-stacking interactions. Proteinoid particles AB1P-AB7P are acid based, and therefore have negative ZP, whereas AB8P and LPAP are basic based proteinoids and have positive ZP. Proteinoid AB9P incorporates both L-LYS and L-Glu at the same (molar) ratio and, hence AB9P ZP value is 0 mV.

Size, SD, ZP and RA Encapsulation Efficiency Analysis of Nano/Micro-Particles Containing RA:

All proteinoid particles were examined for their RA encapsulation ability. Proteinoid particles containing RA were prepared in a similar manner as hallow particles. RA was dissolved in DMSO (0.5 mg/50 μl), and added to the proteinoid mixture prior to cooling. After the particles dispersion reached room temperature, and the particles were formed, the dispersion was dialyzed for the removal of the DMSO. The dispersion was then filtered through a syringe filter (glass microfiber membrane, 3 μm) to remove excess RA crystals that were not encapsulated. When RA is not encapsulated within the particles it forms crystals that are larger than 3 μm, and thus can be filtered out from the particles suspension. After preparation, proteinoid particles were analyzed for their drug loading (L) and encapsulation efficiency (EE) by HPLC. Proteinoid particles containing RA were characterized for their size and SD, and ZP as well. Table 10 shows Size, SD, ZP, L and EE of the different proteinoid particles.

The encapsulated proteinoid particles increased in size compared to hallow particles, AB5P RA, 129.6±13.2 nm and AB6P RA, 64.8±6.5 nm, had the highest L %. Proteinoid particles that encapsulated RA, which is negatively charged, increased in their negative ZP values close to −30 mV or more. As the L % increases so does the ZP, which can indicate that RA encapsulation strengthens the particles and improve their physical stability.

TABLE 10

| Particle* | Size (nm) | SD (%) | ZP (mV) | L (%) | EE (%) |
|---|---|---|---|---|---|
| AB1P RA | 146.7 ± 14.3 | 10 | −23.6 | 2.6 | 54 |
| AB2P RA | 165.5 ± 19.8 | 12 | −26.9 | 1.2 | 24 |
| AB3P RA | 179.1 ± 19.7 | 11 | −29.7 | 1.2 | 24 |
| AB4P RA | 80.5 ± 9.1 | 11 | −36.3 | 2.4 | 50 |
| AB5P RA | 129.6 ± 13.2 | 10 | −36.8 | 4 | 84 |
| AB6P RA | 64.8 ± 6.5 | 10 | −33.6 | 3.8 | 80 |
| AB7P RA | 90.3 ± 11 | 12 | −37.6 | 3.4 | 70 |
| AB8P RA | 383.1 ± 42.1 | 11 | −8.5 | 0 | 0 |
| AB9P RA | 297.8 ± 35.7 | 12 | −1.7 | 0 | 0 |
| LPAP RA | 266.7 ± 29.4 | 11 | +10.4 | 2.3 | 48 |

*Proteinoid particles were made by self-assembly, 10 mg proteinoid dissolved in 10 mL of $10^{-5}$ 1N NaCl solution, and then heated to 80° C., for 30 min. Proteinoid particles were assembled by slowly cooling the dispersion to room temperature. After preparation, proteinoid particles were measured by DLS for their size and size distribution, and by Zeta Potential Analyzer for particles stability.

AB8P RA and AB9P RA did not encapsulate any RA according to the HPLC analysis, however, there is a difference in their ZP values compared to hallow particles. The ZP of AB8P shifted from +1.6 mV to −8.5 mV for AB8P RA. Proteinoid AB8 is L-Lys based, and without being bound by any particular theory, it is assumed that might have formed electrostatic bonds between the amino groups of the proteinoid and the RA carboxyl group. The hydrogen-bond interaction resulted in a monolayer of RA on the particle surface that is under the detection limit of the HPLC. Likewise, AB9 that is partially incorporated with L-Lys, has shifted from ZP 0 mV to −1.7 mV for AB9P RA.

Proteinoids that with the best RA encapsulation ability are AB5, AB6 and AB7 (L=4, 3.8 and 3.4%). Proteinoids AB5 (L-Glu, L-Phe, L-Tyr and 20% PABA) and AB6 (L-Glu, L-Phe, L-Trp) have high content of aromatic rings and therefor can form lipophilic bonds with the RA. Moreover, AB7 (L-Glu, L-Phe, L-Ile and 20% PABA) has a lipophilic residues from the L-Ile side chain that can also form lipophilic bonds with the RA.

Overall, proteinoid AB5 showed the most promising properties for particles formulation. Particles AB5P were the smallest particles, 56.4 nm, with the highest ZP of −19.85 mV between the hallow particles. AB5P RA had the highest L % of 4% and high ZP of −36.8 mV, between the encapsulated particles. Therefore, AB5P and AB5P RA were chosen and further characterized by Cryo TEM, FTIR and TGA measurements.

Characterization of AB5P and AB5P RA

Figure 17A:
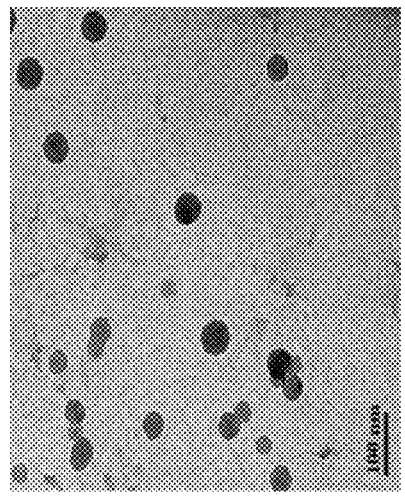
Figure 17B:
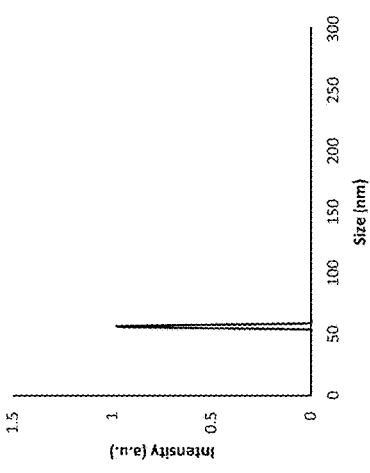
Figure 17C:
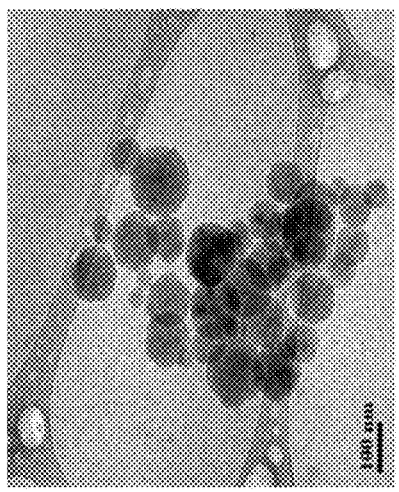
Figure 17D:
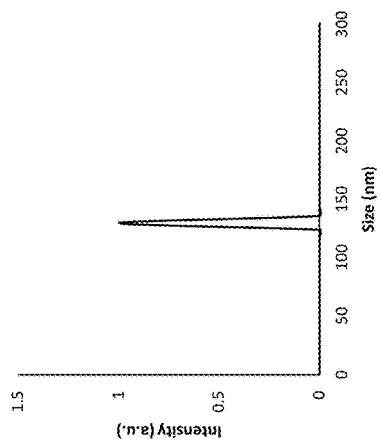

Cryo TEM Analysis:

The particles size was measured by DLS and cryo TEM (FIGS. 17A-D). Proteinoid AB5 produced hallow spherical particles of 56.4±10 nm diameter, as shown by the DLS histogram and cryo TEM images (FIGS. 17A and 17B). Particles containing RA, AB5P RA 5% (w/w), were larger, and have diameter of 129.6±13.2 nm (FIGS. 17C and 17D).

Fourier Transform Infra-Red Spectroscopy (FTIR):

The proteinoid particles and the RA were also characterized by FTIR.

RA powder (FIG. 18A) demonstrated characteristic peaks of alkene, such as, =C—H stretch at 955 $cm^{-1}$ and C=C stretching at 1680 $cm^{-1}$. Furthermore, peaks in the 2800-3000 $cm^{-1}$ region may be attributed to an alkene C—H bend, or to the carboxylic acids O—H stretch of the RA.

Hollow proteinoid particles, AB5P (FIG. 18B) showed characteristic peaks of amine N—H and carboxylic O—H stretching at 2700-3500 $cm^{-1}$ region, amide C—N stretch at 1250 $cm^{-1}$, ketone C=O stretching at 1670 $cm^{-1}$ and an amide N—H bending at 1600 $cm^{-1}$.

Proteinoid particles containing RA, AB5P RA (FIG. 18C), demonstrate different spectra than AB5P. AB5P RA spectra presents peaks that can be attributed to both the proteinoid and to the RA. For example, characteristic peaks of amide C—N stretch at 1250 $cm^{-1}$ and ketone C=O stretching at 1670 $cm^{-1}$ resulting from the proteinoid, and characteristic peaks of alkene, C—H stretching at 2900 $cm^{-1}$ and —C=C—H at 700 $cm^{-1}$ resulting from the RA. Moreover, the peaks at the 2800-3000 $cm^{-1}$ region, that can be relevant to alkene C—H bend and carboxylic acids O—H stretch, appear sharper and more intense, probably as a result of the proteinoid and the RA combination. A new sharp peak of O—H stretching at 3680 $cm^{-1}$ appeared, and it might be due to a hydrogen-bond interaction between the proteinoid and the RA. The FTIR spectra of AB5P RA can suggest to the interaction between the proteinoid and the RA inside or on the surface of the particles.

Thermo Gravimetric Analysis (TGA):

The thermal behavior of the proteinoid particles and RA was investigated by TGA measurements (FIG. 19). The TGA thermogram of RA shows one decomposition slope at 200-500° C. (FIG. 19, "RA"). The proteinoid particles AB5P (FIG. 19) thermogram presents two decomposition slopes, firs slope at 160-270° C., and a second, more moderate slope at 270-500° C. Similarly, AB5P RA thermogram (FIG. 19), also presents two decomposition slopes, firs slope at 210-270° C., and a second slope at 270-500° C. The thermal durability of AB5P RA increased in 50° C. compared to AB5P, possibly due to hydrophobic interaction or hydrogen-bonding between the RA and the proteinoid that strengthens the particle.

In-Vitro Study of the Proteinoid Particles in HaCat Cell Line:

In this study, HaCaT cell line was used as a model for topical treatment HaCaT cell line is a spontaneously transformed human epithelial cell line from adult skin, it is the first permanent epithelial cell line that exhibits normal differentiation and provides a useful tool for studying regulation of keratinization in human cells.

In order to revoke the cell toxicity of the proteinoid particles, in vitro cytotoxicity of the particles was tested using HaCaT cell lines. Cell cytotoxicity was assessed by measuring the release of cytoplasmic lactate dehydrogenase (LDH) into the cell culture supernatants. When tested by the LDH quantitative assay, AB5P and AB5P RA (5 and 20% RA; 0.05 and 0.1% DMSO sequentially) particles dispersed in DDW at concentrations of 0.1 mg/mL had none, or minor cytotoxic effect on the HaCaT cell line (FIG. 20) when compared to untreated (blank) cells. AB5P and AB5P RA can be suitable candidate for topical treatment considering their low toxicity in epithelial cell line.

Particle Penetration into HaCaT Cells:

Proteinoid particles were conjugated to fluorescent dye (cy7) and incubated with HaCaT cells for 4 h, after incubation the cells were washed and analyzed using fluorescence-activated cell sorting (FACS). Results shown in FIG. 21.

Effect of Encapsulation on the Rate of RA Degradation:

Free RA and encapsulated RA and were exposed to artificial light for 24 h and checked by HPLC at several time points up to 24 h. The results in FIG. 22 show that the encapsulation protects at-RA from degradation up to 85% over 24 h.

Example 3

Basic Proteinoids

Preparation and characterization of lysine-based proteinoids by thermal polymerization Lysine was heated to a molten state in an oil bath, under a nitrogen atmosphere. The molten mass was stirred at 180° C. for 30 min. Then a mixture of amino acids was added to a total mass of 5.0 g. The system was kept at 180° C. under a nitrogen atmosphere and permanent stirring. The stirring was achieved by a mechanical stirrer at 150 rpm for 90 min. The amber-brown pasty mass was allowed to cool to room temperature and hardened to a resin-like mass. The residue was then extracted with 20 mL of water and dialyzed through a cellulose membrane (1000 Da MWCO) against distilled water for 48 h. The content of the dialysis tube was then lyophilized to yield the solid proteinoid material. This process was performed with various mixtures of amino acids at different ratios.

The prepared basic proteinoids are summarized in Table 11 showing the amino acid content.

TABLE 11

| Amino acid content (g) | | | | | |
|---|---|---|---|---|---|
| PLLA | (L) Phe | (L) Arg | (L) His | (L) Lys | Polymer |
| 0.5 | 1.0 | — | 1.5 | 2.0 | ProtA1 |
| 0.5 | 1.0 | — | 2.0 | 1.5 | ProtA2 |
| 0.5 | 1.5 | — | 1.5 | 1.0 | ProtA3 |
| — | 1.0 | — | 1.5 | 2.5 | ProtA4 |
| — | 1.0 | 1.0 | 1.0 | 2.0 | ProtA5 |
| 0.5 | 0.75 | 0.75 | 1.5 | 1.5 | ProtA6 |
| — | 1.0 | 1.0 | 1.5 | 1.5 | ProtA7 |

The molecular weights and polydispersity index of all the proteinoids and the molecular weights were determined as described above.

Preparation and Characterization of Basic Proteinoid Particles:

Proteinoid particles were prepared by dissolving 20 mg dried proteinoid in 10 mL superpurified water, and heating the mixture to 80° C. The mixture was then left to cool slowly to room temperature. Proteinoid particles were produced via a self-assembly process. The influence of the initial concentration of the crude proteinoid on the size and size distribution of the obtained particles was examined at 1 mg/mL and 2.5 mg/mL. Moreover, the effect of different solvents on the obtained particles was studied at different environments, e.g. different molar concentrations of NaCl (10−5 M-10−2 M).

The size and size distribution of the resulted particles were checked by DLS and by SEM.

Stability Study of the Proteinoid Particles:

In order to check the stability of the proteinoid particles Zeta potential measurements were performed over changing pH. The ProtA1, ProtA2, and ProtA3 particles were prepared using self-assembly at 2 mg/mL, as mentioned before. To obtain different pH values, 0.01M NaOH or 0.01N HCl solutions were added to the initial solution.

Formation of the Fluorescent Particles:

The ProtA1 particles were prepared by self-assembly, as before. Briefly, 10 mg of the dried fabricated proteinoid were resuspended in 5 ml of super purified water. The mixture was heated to 80° C. while stirring for 30 min, followed by the addition of 0.1 mg (1% of the polymer's weight) of ICG was added to the solution. The mixture was then removed from the hot plate and was allowed to return to room temperature. The excess ICG was removed by dialysis.

Fluorescence intensity of ICG-encapsulated particles was measured using a Maestro II™ in vivo imaging system (Cambridge Research & Instrumentation, Inc., Woburn, Mass.).

A similar experiment was performed with fluorescein. For this experiment ProtA3 particles were used with a proteinoid concentration of 2 mg/mL. Fluorescein was added to the hot proteinoid solution (0.1 mg, 1% of the proteinoid polymer's weight) and the mixture was left to cool to room temperature. The fluorescent particles were cleaned as mentioned before.

Formation of Doxorubicin Basic Proteinoid Particles:

ProtA6 and ProtA7 containing doxorubicin (up to 5%) were prepared similarly to that described for the preparation of proteinoids containing fluorescent dyes (see previous paragraph) substituting the fluorescent dyes for doxorubicin.

Results

Proteinoids ProtA1-A7 were prepared as described above. The suggested mechanism starts with thermal cyclization of the lysine into caprolactam, which further catalyzes the thermal polymerization with the rest of the amino acids, as shown in FIG. 23. Table 12 below exhibits the molecular weights and polydispersity indices (PDI) of the proteinoids.

Considering the fact that the synthesis was based on random polycondensation, and that the PDIs of all synthesized proteinoids are very low (1.01-1.39), we can conclude that the polymerization was mostly uniform. Using the suggested technique produce relatively high-Mw polymers can be produced. The molecular weights of the polymers presented herein varied from 81 kDa up to 858 kDa.

TABLE 12

| PDI | Mp | Mn | Mw | | Proteinoid |
|---|---|---|---|---|---|
| 1.39 | 99300 | 58300 | 81300 | | ProtA1 |
| 1.05 | 760200 | 687600 | 725000 | | ProtA2 |
| 1.01 | 283300 | 297400 | 300300 | | ProtA3 |
| 1.05 | 934100 | 844500 | 858800 | Peak 1 | ProtA5 |
| 1.17 | 219300 | 162900 | 191300 | Peak 2 | |
| 1.02 | 124800 | 134700 | 137100 | | ProtA6 |
| 1.02 | 127000 | 146800 | 146800 | | ProtA7 |

A series of experiments with varying initial concentrations of crude ProtA3 were conducted to obtain monodispersed particles. The results are presented in FIGS. 24A-F. All of the experiments were performed in superpurified water and the concentration of the proteinoid was gradually elevated from 1 to 2.5 mg/mL. As shown in the figure, the particles obtained when the initial concentration of the crude proteinoid was 2 mg/mL (FIGS. 24C and 24D) were the most uniform in size and size distribution. In this case, the hydrodynamic and dry diameters were 96.4±2.6 nm and 104.4±33.1 nm, respectively.

Figure 24F:
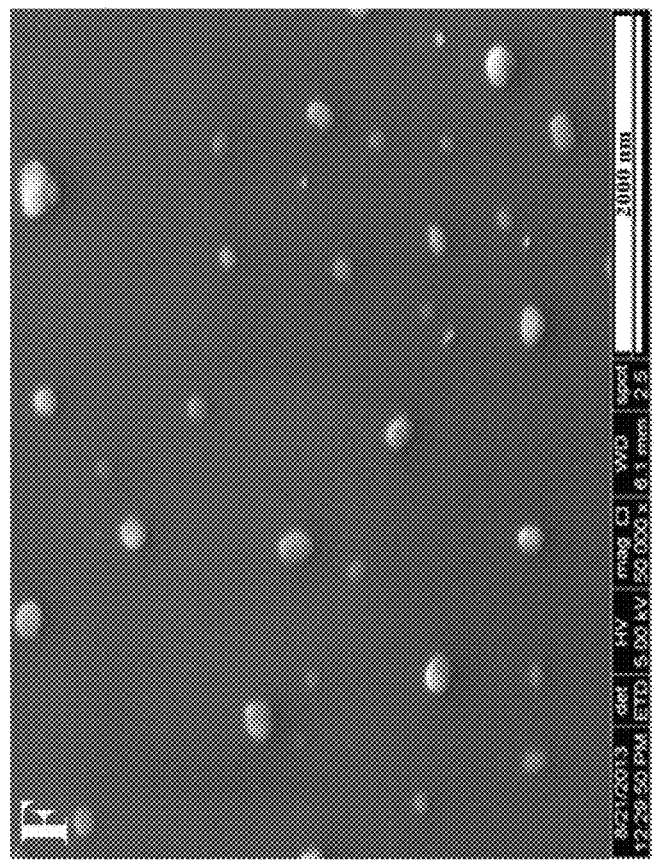
Figure 24E:
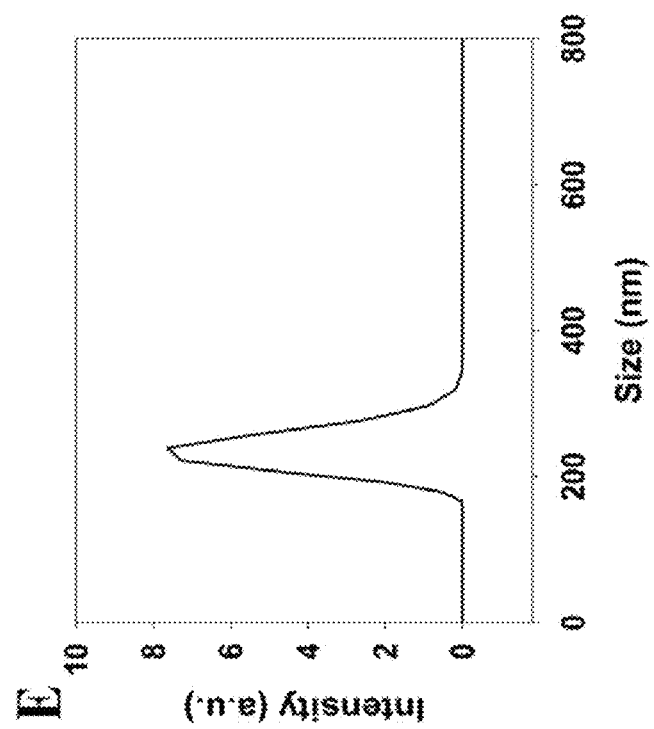

Larger particles were obtained when the concentration was 1 mg/mL (FIGS. 24A and 24B), and their hydrodynamic and dry diameters were 246±65.9 nm and 231.7±81.7 nm respectively. When the concentration was elevated up to 2.5 mg/mL, the maximum hydrodynamic diameter of the particles was 343±58.6 nm and their dry diameter was 210±50.1 nm (FIGS. 24E and 24F).

Stability Study of the Basic Proteinoid Particles:

Zeta potential measurements were performed on the proteinoid particles. The results of ProtA1-3 are shown in FIG. 25. It can be seen that the isoelectric point of ProtA1 is around pH 7. This is because ProtA1 has a greater amount of lysine with $\alpha$- and $\xi$-amine groups, whose pKa values are 9.0 and 10.5 respectively, and in pure water those groups will be protonated and have a positive charge. In the same manner, the carboxylic group, whose pKa is 2.18, will be negatively charged. However, ProtA1 particles also consist of histidine, phenylalanine and PLLA. Histidine has a combination of imidazole and an $\alpha$-amine group, whose pKa values are 6.04 and 9.33, respectively.

Also, the pKa of the carboxylic group of histidine is 1.77, in neutral pH histidine will be uncharged and will not contribute to the overall particle's charge. Phenylalanine with $\alpha$-amine group (pKa=9.24) and carboxylic group (pKa=2.58) will not contribute any charge to the particles either. As can be seen in FIG. 25, the net potential of ProtA1 particles is positive.

The presence of PLLA (whose pKa is 3.9-4.9) in all of the particles may cause a slight negative potential.

FIG. 25 shows that the particles obtained from all of three types of polymers demonstrated positive zeta potential in acidic pH. When the pH was increased, the values of zeta potential decreased simultaneously. In basic pH all obtained particles showed very high negative zeta potentials because of the unprotonated carboxylic groups of amino acids and PLLA.

The positive zeta potential values, which were measured in this study, serve as additional proof polymer-histidine conjugates can be endosomolytic.

NIR Fluorescent Particles Formation:

ICG was encapsulated within the ProtA1 particles. The dry diameter of ICG encapsulated particles was 130.9±37.65 nm. The hydrodynamic diameter, which was measured by using DLS, was 256.7±46.4 nm. Without being bound by any particular mechanism, the difference between the dry diameter and the hydrodynamic diameter can be explained by the fact that the hydrodynamic diameter also takes into account the water molecules adsorbed on surface of the particles. ICG was encapsulated in ProtA2 and ProtA3 particles as well. FIG. 26A illustrates that the maximum absorbance of the free ICG and the NIR fluorescent proteinoid particles occurs at approximately 780 and 810-840 nm respectively, and the maximum fluorescence emission intensity of the NIR fluorescent proteinoid particles occurs at approximately 810 nm (FIG. 26B). ProtA2 particles gained greater fluorescence than particles formed from the other proteinoids.

Example 4

Synthesis of Basic Proteinoid-PLLA Polymers with Varying Ratios of PLLA

All the polymers were produced via a simple thermal condensation reaction which utilizes carboxyl and amine groups that are part of an amino acid side chain or those at the $\alpha$-position. Table 13 below summarizes the percentage of amino acids and PLLA content in polymers that were synthesized.

Lysine was heated to a molten state in an oil bath, under a nitrogen atmosphere. The molten mass was stirred at 180° C. for 30 min. Then a mixture of amino acids was added to a total mass of 5.0 g. The system was kept at 180° C. under a nitrogen atmosphere and permanent stirring. The stirring was achieved by a mechanical stirrer at 150 rpm for 90 min. The amber-brown pasty mass was allowed to cool to room temperature and hardened to a resin-like mass. The residue was then extracted with 20 mL of water and dialyzed through a cellulose membrane (1000 Da MWCO) against distilled water for 48 h.

Ten additional different proteinoids were synthesized in total. To determine if changing the amount of PLLA allows control of the size, size distribution and rate of particle degradation, the proteinoids were synthesized with varying PLLA content starting at 0%, and going up to 10%. The base composition of lysine, phenylalanine and histidine was kept constant across all proteinoids from the first group ProtB1-ProtB4 (Table 13 below). Proteinoids that are presented in the second group have the same percentage of PLLA as ProtB4 (10%), however, the amino acid composition of all six proteinoids of this group varies. In this case improving the physical properties of the proteinoids by increasing the relative content of phenylalanine was aimed at, so as to enhance the rigidity to the proteinoid backbone. The addition of arginine and histidine can guarantee the cell penetration of the proteinoid NPs as well. In all cases, altering the proteinoids amino acid content has a significant effect on the physical and chemical properties of the obtained polymers.

TABLE 13

| | Amino acid content (weight % of the total composition) | | | | |
|---|---|---|---|---|---|
| Proteinoid | (L)Lys | (L)His | (L)Arg | (L)Phe | PLLA (2 kDa) |
| ProtB1 | 30 | 30 | 20 | 20 | 0 |
| ProtB2 | 30 | 30 | 17.5 | 20 | 2.5 |
| ProtB3 | 30 | 30 | 15 | 20 | 5 |
| ProtB4 | 30 | 30 | 10 | 20 | 10 |
| ProtC1 | 40 | 30 | — | 20 | 10 |
| ProtC2 | 30 | 40 | — | 20 | 10 |
| ProtC3 | 30 | 30 | — | 30 | 10 |
| ProtC4 | 25 | 35 | 15 | 15 | 10 |
| ProtC5 | 25 | 30 | 15 | 20 | 10 |
| ProtC6 | 25 | 20 | 15 | 30 | 10 |
| ProtC7 | 25 | 25 | 15 | 25 | 10 |

The molecular weights and polydispersity index of the dried crude proteinoids were determined using GPC as described hereinabove.

All of the measurements were done in water, at 589 nm at 25° C. Table 14 shows the characteristic molecular weights (Mw, Mn, Mp), polydispersity and optical activity of the prepared proteinoids.

TABLE 14

| Proteinoid | Mw | Mn | Mp | PDI |
|---|---|---|---|---|
| ProtB1 | 83443 | 81125 | 88897 | 1.03 |
| ProtB2 | 93496 | 92457 | 93029 | 1.00 |
| ProtB3 | 129859 | 128863 | 127242 | 1.02 |
| ProtB4 | 100773 | 95351 | 92906 | 1.06 |
| ProtC1 | 81300 | 58300 | 99300 | 1.39 |
| ProtC2 | 42959 | 40180 | 33573 | 1.07 |
| ProtC3 | 300300 | 297400 | 283300 | 1.01 |
| ProtC4 | 122442 | 121401 | 123800 | 1.01 |
| ProtC5 | 145107 | 141852 | 136560 | 1.02 |
| ProtC6 | 149355 | 145973 | 142401 | 1.02 |
| ProtC7 | 140760 | 139392 | 136918 | 1.01 |

Table 14 indicate relatively low PDI values for the obtained proteinoids. The highest PDI (1.39) was observed for ProtC1, composed of 10% PLLA, 20% Phe, 30% His, and 40% Lys. The PDIs of all others proteinoids varied from 1.0 to 1.04. As we can see from Table 14, all obtained proteinoids demonstrated high molecular weights and low PDIs.

Nanoparticle Formation and Doxorubicin Loading:

Nanoparticles were formed from ProtB4 and ProtC4-7, either hollow or containing 15% Dox. Drug loading was performed by the encapsulation of Dox during the self-assembly. In most experiments, varying amounts (0, 10, 15, 20, 25 and 30 weight % relative to the proteinoid) of Dox (0, 5, 7.5, 10, 12.5 and 15 mg) were dissolved in 0.5 ml of water and added to the heated solution of proteinoid (50 mg in 4.5 ml) to give total volume of 5 ml. The drug excess was removed by dialysis against super purified water, repeated three times. The Dox loading content was determined by the following method: the Dox-encapsulated NPs were lyophilized and then disrupted by an addition of pH 2 buffer and sonication. The sample was then analyzed using a Cary 100 UV Visible spectrophotometer (Agilent Technologies Inc.) at 487 nm. Prior to this analysis, quantification was performed using the calibration curve of the Dox standard solutions (0-125 µg/ml) in a pH 2 buffer at 487 nm. Each experiment was carried out in triplicate, and the average values were compared. Excitation and emission spectra were recorded using a Cary Eclipse spectrofluorometer (Agilent Technologies Inc.).

Drug loading efficiency was measured by the ratio of Dox in NPs to the reweighed Dox-encapsulated NPs as calculated using UV spectrophotometric measurements. The encapsulation of 15, 20 and 25% Dox, it was found that the whole amount (close to 100%) of Dox was encapsulated within the proteinoid NPs. Self-assembly of proteinoid with 30% Dox did not yield NPs.

The particle size and size distribution of ProtB4, ProtC4-C7 encapsulating 15% Dox were measured by dynamic light scattering (DLS). The mean diameter varied from 79.8±10.3 to 193.4±31.6 nm (Table 15, presenting characteristics of Dox-loaded NPs obtained from ProtB4 and ProtC4-C7 encapsulating 15% Dox). All samples show relatively narrow size distribution. To check the stability of the proteinoid particles zeta potential measurements were performed. It can be seen that the positive zeta potential value increases with increasing phenylalanine ratio in the polymer. Having all that in mind, ProtC6 was chosen for further experiments.

FIGS. 27A-B show the diameters of hollow and 15% Dox-encapsulated ProtC6 NPs by cryo-TEM.

TABLE 15

| Type of proteinoid | ζ (mV) | Size of NPs (nm) |
|---|---|---|
| ProtB4 | 8.48 | 79.8 ± 10.3 |
| ProtC4 | 8.84 | 100.3 ± 38.7 |
| ProtC5 | 8.05 | 302.2 ± 31.75 |
| ProtC6 | 16.6 | 111 ± 15.2 |
| ProtC7 | 10.13 | 193.4 ± 31.6 |

Table 16 shows the ProtC6 Dox-encapsulating NPs yield and size. The smallest NPs were obtained when encapsulating 20% Dox, at a yield of 97%. These particles were chosen for further research. The 20% Dox-containing NPs contain a higher amount of the active Dox in comparison to commercial Doxil (approximately 12.5 weight % of the liposome).

TABLE 16

| Drug fed initially (%) | Nanoparticles formation yield (%) | Size of NPs (nm) |
|---|---|---|
| 10 | 99 | 96.5 |
| 15 | 97 | 111 ± 15.2 |
| 20 | 97 | 63.4 ± 17.2 |
| 25 | 94 | 116 ± 2 |
| 30 | No particles detected | |

Free Dox and Dox-encapsulated NPs (containing the same amount of Dox) absorption spectra were measured at pH 2 (wherein the particles are dissolved) and physiological pH (7.4), shown in FIG. 28. The main absorption peak of Dox occurred at 487 nm at each tested pH. The main absorption peak at pH 2 was shaped similarly to Dox, however, at pH 7.4 the intensity of the main absorption peak of the Dox-encapsulated NPs was much lower than the intensity of main peak of free Dox. This indicates the encapsulation of the drug within the NPs. Additionally, it is seen that at pH 2 the absorption peaks of the Dox-encapsulated NPs and the free Dox are similar. This fact reveals the release of encapsulated Dox from the disrupted NPs.

Biodegradation of the Dox-NPs:

The release of Dox was measured in order to determine the biodegradation of the NPs. Dox-NPs were put in activated serum and in PBS as control, incubated at 37° C. and samples were taken at 4 time points: 1 min, 1 h, 5 h and 24 h. The Dox was filtered and checked by UV at 487 nm.

In PBS, no release of Dox was observed over 24 h, and further checked after a weak, demonstrating the stability of the NPs in storage conditions. In serum, close to 20% of the Dox is released over 5 h.

TRAIL Conjugation to the Dox NPs:

Hollow NPs and Dox-containing NPs were conjugated to TRAIL via two routes: 1. Carbodiimide activation of the carboxylate groups on the particle surface; 2. NETS-PEG-Maleimide 3000 spacer between the particle surface and TRAIL. The concentration of the TRAIL conjugated to the NPs was determined using an ELISA assay. This ELISA assay indicated that the concentration of TRAIL is 3.5±0.3 µg per 1 mg NPs wherein the TRAIL was conjugated via a PEG spacer. The concentration of TRAIL conjugated directly to the NPs surface was similar.

Cell Proliferation Analysis:

XTT analysis was performed on HCT116, A172 and 4T1 cells, according to manufacturer instructions (Biological Industries).

HCT116 human colon cancer cells were treated with 0.01 mg/mL NPs, hollow or containing 1.66 µg Dox, non-conjugated and conjugated to 35 ng TRAIL. Free Dox, free TRAIL and PBS served as control groups. Absorption was measured for all samples, each in six, with TECAN spectrophotometer to determine the cell viability. FIG. 29 shows the cell viability of HCT116 cells 24 h and 72 h post-treatment. As observed, TRAIL conjugated using PEG or directly to the NPs does not affect the NPs' toxicity. It was chosen to continue with the TRAIL-PEG-Dox NPs, as PEGylation modifies the physical and chemical properties of the drug, and can decrease immunogenicity and improve drug solubility.

In addition, PEGylation improves drug stability. Consequently, it extends blood half-life and therefore reduces dose frequency. Importantly, both kinds of Dox-NPs conjugated to TRAIL show good toxicity after 24 h, and their activity is preserved leading to 30-35% cell viability after 72 h. This shows the synergetic effect of both Dox and TRAIL in a single NP. NPs with PEG-Dox, PEG-TRAIL or PEG only, did not have a toxic effect. Interestingly, although free TRAIL shows good toxicity over 24 h, after 72 h there is a recovery in the cell viability, probably due to growth of the surviving living cells, that are no longer under TRAIL treatment. PEG-TRAIL NPs (without Dox) show the same effect after 72 h, in comparison to 24 h.

HCT116 cells were treated with a higher dose of 0.05 mg/mL NPs and an equivalent amount Dox-containing commercial Doxil (8.3 µg Dox). FIG. 30 shows the cell viability 24 h after treatment. The highest toxicity was achieved by the treatment with TRAIL-PEG-Dox NPs, again, showing the synergetic affect. It can be seen that Doxil hardly affected the cell viability over 24 h at all.

4T1 mouse breast cancer cells were treated with 0.05 mg/mL NPs. FIG. 31 shows the cell viability 72 h after treatment. Again, the highest toxicity was achieved by the treatment with TRAIL-PEG-Dox NPs.

A172 human glioblastoma cells were treated with 0.05 mg/mL NPs, an equivalent amount Dox-containing commercial Doxil (8.3 µg Dox), free TRAIL, free Dox and a combination of Doxil and free TRAIL. FIG. 32 shows the cell viability 24 and 48 h after treatment. Here, the cells treated with Doxil reached viability levels of 63% after 48 h and the combination of Doxil and TRAIL led to 14% cell viability over 24 h, but the cells recovered over 48 h, reaching 68%. The highest toxicity (2% viability) was achieved by the treatment with TRAIL-PEG-Dox NPs.

Cell Uptake:

HCT116 cells were seeded on a cover glass and treated for 4 h and 24 h with 0.02 mg/mL TRAIL-PEG-Dox NPs containing a NIR fluorescent dye Cy7 covalently bound on the surface. After fixation, the cells were examined with a fluorescent microscope in brightfield, red fluorescence for Dox, NIR fluorescence for Cy7 and nucleus in blue (DAPI). FIGS. 33 and 34 show that the NPs entered the cells in NIR (green) and red fluorescence. The red fluorescence is seen both at the nucleus and cytoplasm, NIR is detected only in the cytoplasm. This indicates that the Dox is released. After 24 h the red fluorescence intensity is higher in the nucleus, indicating the continuing release of Dox over time.

Cytokines Induction Assay:
Method:

In order to evaluate the safety profile of the ProtC6-Dox NPs as a future drug delivery vehicle, an ex-vivo cytokine induction study was performed using the human Peripheral Blood Mononuclear Cells (PBMCs), which examined the secretion of major inflammatory cytokines. The secretion level of three different inflammatory interleukins was tested using IL-6 and TNF-a as a model for the innate immune response and IL-10 as a model for the late immune response.

Cytokines induction assay was performed according to Landesman-Milo D1 et al., Hyaluronan grafted lipid-based nanoparticles as RNAi carriers for cancer cells. Cancer Lett. 2013 Jul. 1; 334(2):221-7.

The effect of Dox nanoparticles (NPs), in presence or absence of bound PEG (polyethylene glycol), on TNF-α, IL-10 and IL-6 cytokines secretion from human Peripheral Blood Mononuclear Cells (PBMCs) was tested. PBMCs were freshly isolated from 3 healthy human donors obtained from Tel Hashomer (Sheba) Blood Bank. Whole blood of each human was diluted with PBS$^{-/-}$ (Calcium and Magnesium free, Biological Industries, Bet Haemek) in a volume ratio of 1:1. Samples containing 4 ml diluted blood were then gently overlaid onto 3 ml Ficoll (GE Healthcare) (3:4 ratio). Gradient was then obtained by centrifugation at 22° C., 1400 rpm for 35 min. Opaque-Light PBMCs ring was removed from the interphase into a new tube. PBMCs were washed with PBS$^{-/-}$ and then centrifuged at 1400 rpm for 10 min. Each PBMCs pellet was resuspended in PBMC growth medium (with 5% Fetal Bovine Serum and 1% Penicillin-Streptomycin Solution) to which PBS dispersion of the Dox NPs or Dox-PEG NPs were added. The final concentration of each 1 ml well (24 well plates) contained $3*10^6$ cells and 0.05 mg NPs. Lipopolysaccharides (LPS, L6529, sigma) was used as a positive control (100 ng/ml) and PBS$^{-/-}$ as a negative control. The different 24 well plates were then incubated at 37° C. humidified, 5% $CO_2$ for 2 and 24 h. Upon incubation, at each interval of time, the cells were centrifuged at 1400 rpm for 10 min and the supernatant was removed and stored in −80° C. freezer for quantification of IL-6, TNF-α and IL-10 secreted cytokines. Human cytokines TNF-α, IL-10 and IL-6 levels were determined using Human IL-6 ELISA kit (RayBiotech), IL-10 ELISA kit (RayBiotech), and Human TNF-α ELISA kit (RayBiotech), respectively, according to the manufacturer instructions.

Results:

The results are summarized in Tables 17 and 18. Neither the Dox NPs nor the Dox-PEG NPs, caused an elevated secretion of both innate and late cytokines response in two different time points, 2 h (Table 5) and 24 h (Table 6) post incubation with the particles. As a positive control, we used the Toll-like receptor 4 (TLR4) natural ligand, lipopolysaccharides (LPS) that secreted high levels of both TNF-α and IL-6 already 2 h post incubation with increase after 24 h of exposure to the LPS. IL-10 was secreted after 24 h, as expected.

Table 17 presents the effect of Dox nanoparticles (NPs), in presence or absence of bound PEG on the secretion of TNF-α, IL-10 and IL-6 in human PBMCs 2 h post incubation.

TABLE 17

| Treatment | TNF-α (pg/ml) | IL-10 (pg/ml) | IL-6 (pg/ml) |
|---|---|---|---|
| Negative control (PBS) | N.D. | N.D. | N.D. |
| Positive control (LPS 1 µg/ml) | 6586 ± 1591 | N.D. | 1788 ± 782** |
| Dox NPs | N.D. | N.D. | N.D. |
| PEG-Dox NPs | N.D. | N.D. | N.D. |

Values are expressed as means ± sdv.
N.D.—not detectable.
**Upper limit of quantification.

Table 18 presents the effect of Dox nanoparticles (NPs), in presence or absence of bound PEG on the secretion of TNF-α, IL-10 and IL-6 in human PBMCs 24 h post incubation.

TABLE 18

| Treatment | TNF-α (pg/ml) | IL-10 (pg/ml) | IL-6 (pg/ml) |
|---|---|---|---|
| Negative control (PBS) | N.D. | N.D. | N.D. |
| Positive control (LPS 1 µg/ml) | 16697 ± 8875 | 669 ± 42** | 2480 ± 321** |
| Dox NPs | N.D. | N.D. | N.D. |
| PEG-Dox NPs | N.D. | N.D. | N.D. |

Values are expressed as means ± sdv.
N.D.—not detectable.
**Upper limit of quantification.

As a summary, optimal NPs were achieved, made of ProtC6 with 20% Dox, which is a higher concentration comparing to commercial Doxil. The ProtC6 NPs were found to be non-toxic. The ProtC6 TRAIL-PEG-Dox NPs showed good results in-vitro, i.e. reaching very low cell viability, in comparison to commercial Doxil. The ProtC6 NPs containing Dox showed no secretion of major inflammatory cytokines in ex-vivo cytokine induction study on human PBMCs.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A proteinoid compound comprising a polymeric backbone, wherein said polymeric backbone comprises monomeric units and polyester, wherein each of said monomeric units being derived from an amino acid, and wherein said polymeric backbone is characterized by a molecular weight (Mw) of at least 15,000 Da.

2. The proteinoid compound of claim 1, wherein said amino acid, in each instance, is selected from the group consisting of: Glu, Lys, Asp, Arg, Tyr, His, Ala, Phe, Cys, Ile, and p-amino benzoic acid.

3. The proteinoid compound of claim 1, wherein said polyester is selected from the group consisting of polylactide, polyglycolide, polycaprolactone, and polyhydroxyalkanoate.

4. The proteinoid compound of claim 1, wherein said polymeric backbone is represented by the following formula $[Phe]_n[Arg]_x[His]_y[Lys]_z[A_4]$
wherein:
$A_4$ represents a polyester;
n, x, y, and z are integers, independently, representing the total numbers of Phe, Arg, His, and Lys, respectively, in the polymeric backbone, such that n+x+y+z has a value of at least 100.

5. The proteinoid compound of claim 1, wherein said polymeric backbone is represented by the following formula: $[A_1]_x[A_2]_y[A_3]_z[A_4]$
wherein:
a) $A_1$, in each instance, is a monomeric unit derived from an amino acid selected from Glu and Lys;
b) $A_2$, and $A_3$ are each, independently, a monomeric unit derived from an amino acid or are each, independently, absent;
c) $A_4$ represents the polyester, and
d) x, y, and z are integers, independently, representing the total numbers of $A_1$, $A_2$, and $A_3$, respectively, in said polymeric backbone, such that x+y+z has a value of at least 100.

6. The proteinoid compound of claim 5, wherein the monomeric units $A_2$ and $A_3$ are derived from the group consisting of:Asp, Lys, Arg, and Phe.

7. The proteinoid compound of claim 1, wherein said polyester is at least 1%, by weight, of the polymeric backbone.

8. The proteinoid compound of claim 5, wherein $A_1$ is Glu, $A_2$ is Phe and $A_3$ is absent.

9. The proteinoid compound of claim 5, wherein $A_1$ is Glu, $A_2$ is Asp, and $A_3$ is selected from the group consisting of Lys, Phe, or is absent.

10. The proteinoid compound of claim 5, wherein $A_1$ is Glu, $A_2$ is Lys, and $A_3$ is Phe or is absent.

11. The proteinoid compound of claim 5, wherein x, y, and z have a value such that at least one of: x/y, x/z, and y/z ranges from about 1:3 to about 3:1.

12. The proteinoid compound of claim 4, wherein $A_4$ is polyactide.

13. The proteinoid compound of claim 5 being in the form of a hollowsphere.

14. A composition-of-matter comprising one or more of the hollowspheres of claim 13.

15. The composition-of-matter of claim 14, characterized by a dispersity index (Đ) value of less than 1.1.

16. The composition-of-matter of claim 14, further comprising one or more agents selected from: labeling compound, UV blocker, an antibacterial compound, a magnetite, an antioxidant, a filler, biologically active agent, said one or more agents being attached to and/or encapsulated within said hollowsphere.

17. A method of monitoring the presence and metastases of cancer in a body of an individual, the method comprising administering to the individual the composition-of-matter of claim 14, the composition further comprises a labeling agent, and employing an imaging technique for monitoring a distribution of the composition-of-matter within the body or within a portion thereof, thereby monitoring the presence and metastases of cancer in a body of an individual.

18. A process of synthesizing a proteinoid compound characterized by molecular weight (Mw) of at least 15,000 Da, the process comprising:
a) heating one or more types of amino acid to a temperature that ranges from 100° C. to 200° C., under an inert gas, thereby forming a molten content or a mixture of said one or more amino acids;
b) stirring said molten content or a mixture at a temperature that ranges from 100° C., to 200° C., for at least 30 min, thereby polymerizing a plurality of monomeric units and polyester, each of said monomeric units being derived from said one or more amino acids in said mixture;
c) bringing the content or mixture to room temperature;

d) adding water to said content or a mixture, thereby obtaining a proteinoid compound solution; and e) cleaning (e.g., dialyzing) said solution to thereby obtain the proteinoid compound.

19. The process of claim 18, wherein said amino acid is selected from the group consisting of: Glu, Lys, Asp, Arg, Tyr, His, Ala, Phe, Cys, Ile, and p-amino benzoic acid.

* * * * *